US007157490B2

(12) United States Patent
Colandrea et al.

(10) Patent No.: US 7,157,490 B2
(45) Date of Patent: Jan. 2, 2007

(54) PHENYLALANINE DERIVATIVES AS DIPEPTIDYL PEPTIDASE INHIBITORS FOR THE TREATMENT OR PREVENTION OF DIABETES

(75) Inventors: Vincent J. Colandrea, North Brunswick, NJ (US); Scott D. Edmondson, New York, NY (US); Robert J. Mathvink, Red Bank, NJ (US); Anthony Mastracchio, Edison, NJ (US); Ann E. Weber, Scotch Plains, NJ (US); Jinyou Xu, Scotch Plains, NJ (US)

(73) Assignee: Merck & Co., Inc., Rahway, NJ (US)

( * ) Notice: Subject to any disclaimer, the term of this patent is extended or adjusted under 35 U.S.C. 154(b) by 306 days.

(21) Appl. No.: 10/481,352

(22) PCT Filed: Nov. 3, 2003

(86) PCT No.: PCT/US03/34924

§ 371 (c)(1),
(2), (4) Date: Dec. 19, 2003

(87) PCT Pub. No.: WO2004/043940

PCT Pub. Date: May 27, 2004

(65) Prior Publication Data

US 2005/0222140 A1 Oct. 6, 2005

Related U.S. Application Data

(60) Provisional application No. 60/501,232, filed on Jun. 19, 2003, provisional application No. 60/424,483, filed on Nov. 7, 2002.

(51) Int. Cl.
*C07D 277/04* (2006.01)
*C07D 207/04* (2006.01)
*A61K 31/40* (2006.01)
*A61K 31/426* (2006.01)

(52) U.S. Cl. ............... 514/423; 514/369; 548/200; 548/541

(58) Field of Classification Search ............... 548/200, 548/541; 514/369, 423
See application file for complete search history.

(56) References Cited

U.S. PATENT DOCUMENTS

| 4,386,090 | A | | 5/1983 | Moinet et al. |
| 5,556,941 | A | * | 9/1996 | Kolar et al. ............... 530/322 |
| 5,939,560 | A | | 8/1999 | Jenkins et al. |
| 6,015,812 | A | * | 1/2000 | Ferrari et al. ............ 514/235.8 |
| 2004/0121965 | A1 | * | 6/2004 | Greenberger et al. ......... 514/19 |
| 2004/0176428 | A1 | * | 9/2004 | Edmondson et al. ....... 514/365 |

FOREIGN PATENT DOCUMENTS

| WO | WO 97/40832 A1 | 11/1997 |
| WO | WO 98/19998 A2 | 5/1998 |
| WO | WO 98/19998 A3 | 5/1998 |
| WO | WO 00/34241 A1 | 6/2000 |
| WO | WO 01/34594 A1 | 5/2001 |
| WO | WO 01/42262 | 6/2001 |
| WO | WO 01/96295 A2 | 12/2001 |
| WO | WO 01/96295 A3 | 12/2001 |
| WO | WO 02/02560 A2 | 1/2002 |
| WO | WO 02/02560 A3 | 1/2002 |
| WO | WO 03/000180 A2 | 1/2003 |
| WO | WO 03/000180 A3 | 1/2003 |
| WO | WO 03/000181 A2 | 1/2003 |
| WO | WO 03/000181 A3 | 1/2003 |
| WO | WO 03/004498 A1 | 1/2003 |
| WO | WO 02/076450 A1 | 10/2003 |
| WO | WO 03/082817 A2 | 10/2003 |

OTHER PUBLICATIONS

STN results.*
STN results.*
CAS registry No. 676637-07-3 in Document No. 140:304081.*
McIntosh et al., Dipeptidyl Peptidase IV Inhibitors: How do they Work as new Antidiabetic Agens?, Regulatory Peptides, 128:159-165 (2005).*
Deacon & Holst, Dipeptidyl Peptidase IV Inhibitors: A Promising New Therapeutic Approach for the Management of Type 2 Diabetes, INT. J. Biochem. & Cell Bio., 38:831-844 (2006).*
Expert Opinion onTherapeutic Patents, "Novel N-substituted-2-cyanopyrrolidines as potent inhibitors of dipeptidyl peptidase IV in the treatment of non-insulin-dependent diabetes mellitus", vol. 10 (#12) p. 1937-1942 (2000).
Expert Opinion on Investig. Drugs, "Gut peptides in the treatment of diabetes mellitus", (2004) 13 (3) 177-188.
Expert Opinion on Investig. Drugs, "Therapeutic potential of dipeptidyl peptidase IV inhibitors for the treatment of type 2 diabetes", (2003) 12:87-100.
Expert Opinion on Therapeutic Patents, "Dipeptidyl peptidase IV inhibitors as new therapeutic agents for the treatment of Type 2 diabetes", (2003) 13: 499-510.

* cited by examiner

*Primary Examiner*—Celia Chang
*Assistant Examiner*—R. James Balls
(74) *Attorney, Agent, or Firm*—Philippe L. Durette; Melvin Winokur

(57) ABSTRACT

The present invention is directed to phenylalanine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

23 Claims, No Drawings

PHENYLALANINE DERIVATIVES AS DIPEPTIDYL PEPTIDASE INHIBITORS FOR THE TREATMENT OR PREVENTION OF DIABETES

CROSS REFERENCE TO RELATED APPLICATIONS

This application is the National Stage of International Application No. PCT/US03/34924 filed 03 Nov. 2003, which claims the benefit under 35 U.S.C. 119(e) of U.S. Provisional Application No. 60/424,483, filed 07 Nov. 2002 and No. 60/501,232, filed 19 Jun. 2003.

BACKGROUND OF THE INVENTION

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In type 1 diabetes, or insulin-dependent diabetes mellitus (IDDM), patients produce little or no insulin, the hormone which regulates glucose utilization. In type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β-cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) are a more recently described class of compounds with potential for ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensititization that is observed with the glitazones. Newer PPAR agonists that are being tested for treatment of Type 2 diabetes are agonists of the alpha, gamma or delta subtype, or a combination of these, and in many cases are chemically different from the glitazones (i.e., they are not thiazolidinediones). Serious side effects (e.g. liver toxicity) have occurred with some of the glitazones, such as troglitazone.

Additional methods of treating the disease are still under investigation. New biochemical approaches that have been recently introduced or are still under development include treatment with alpha-glucosidase inhibitors (e.g. acarbose) and protein tyrosine phosphatase-1B (PTP-1B) inhibitors.

Compounds that are inhibitors of the dipeptidyl peptidase-IV ("DP-IV" or "DPP-IV") enzyme are also under investigation as drugs that may be useful in the treatment of diabetes, and particularly type 2 diabetes. See for example WO 97/40832, WO 98/19998, U.S. Pat. No. 5,939,560, Bioorg. Med. Chem. Lett., 6: 1163–1166 (1996); and Bioorg. Med. Chem. Lett., 6: 2745–2748 (1996). The usefulness of DP-IV inhibitors in the treatment of type 2 diabetes is based on the fact that DP-IV in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DP-IV leads to decreased inactivation of the incretins, and this in turn results in increased effectiveness of the incretins in stimulating production of insulin by the pancreas. DP-IV inhibition therefore results in an increased level of serum insulin. Advantageously, since the incretins are produced by the body only when food is consumed, DP-IV inhibition is not expected to increase the level of insulin at inappropriate times, such as between meals, which can lead to excessively low blood sugar (hypoglycemia). Inhibition of DP-IV is therefore expected to increase insulin without increasing the risk of hypoglycemia, which is a dangerous side effect associated with the use of insulin secretagogues.

DP-IV inhibitors also have other therapeutic utilities, as discussed herein. DP-IV inhibitors have not been studied extensively to date, especially for utilities other than diabetes. New compounds are needed so that improved DP-IV inhibitors can be found for the treatment of diabetes and potentially other diseases and conditions.

SUMMARY OF THE INVENTION

The present invention is directed to phenylalanine derivatives which are inhibitors of the dipeptidyl peptidase-IV enzyme ("DP-IV inhibitors") and which are useful in the treatment or prevention of diseases in which the dipeptidyl peptidase-IV enzyme is involved, such as diabetes and particularly type 2 diabetes. The invention is also directed to pharmaceutical compositions comprising these compounds and the use of these compounds and compositions in the prevention or treatment of such diseases in which the dipeptidyl peptidase-IV enzyme is involved.

DETAILED DESCRIPTION OF THE INVENTION

The present invention relates to phenylalanine derivatives useful as inhibitors of dipeptidyl peptidase-IV. Compounds of the present invention are described by structural formula I:

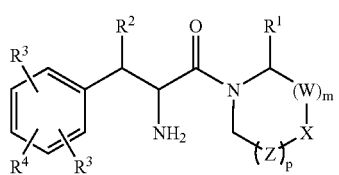

or a pharmaceutically acceptable salt thereof; wherein
each n is independently 0, 1, or 2;
m and p are each independently 0 or 1;
X is $CH_2$, S, CHF, or $CF_2$;
W and Z are each independently $CH_2$, CHF, or $CF_2$;
$R^1$ is hydrogen or cyano;
each $R^3$ is independently selected from the group consisting of hydrogen, halogen, $C_{1-4}$ alkyl, $C_{1-4}$ alkoxy, cyano, trifluoromethyl, trifluoromethoxy, and hydroxy;
$R^4$ is aryl, heteroaryl, or heterocyclyl, wherein aryl, heteroaryl, and heterocyclyl are unsubstituted or substituted with one to five $R^5$ substituents;
$R^2$ is selected from the group consisting of hydrogen,
  $C_{1-10}$ alkyl, wherein alkyl is unsubstituted or substituted with one to five substituents independently selected from halogen or hydroxy,
  $C_{2-10}$ alkenyl, wherein alkenyl is unsubstituted or substituted with one to five substituents independently selected from halogen or hydroxy,
  $(CH_2)_n$-aryl, wherein aryl is unsubstituted or substituted with one to five substituents independently selected hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$-heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$-heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$—$C_{3-6}$ cycloalkyl, wherein cycloalkyl is unsubstituted or substituted with one to three substituents independently selected from halogen, hydroxy, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$COOH,
  $(CH_2)_n$COO$C_{1-6}$ alkyl,
  $(CH_2)_n$CONR$^6$R$^7$, wherein $R^6$ and $R^7$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
  or wherein $R^6$ and $R^7$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens; and
  wherein any methylene ($CH_2$) carbon atom in $R^2$ is unsubstituted or substituted with one to two groups independently selected from halogen, hydroxy, and $C_{1-4}$ alkyl unsubstituted or substituted with one to five halogens;
each $R^5$ is independently selected from the group consisting of
halogen,
cyano,
oxo,
hydroxy,
$C_{1-6}$ alkyl, wherein alkyl is unsubstituted or substituted with one to five halogens,
$C_{1-6}$ alkoxy, wherein alkoxy is unsubstituted or substituted with one to five halogens,
$(CH_2)_n$—NR$^6$R$^7$,
$(CH_2)_n$—CONR$^6$R$^7$,
$(CH_2)_n$—OCONR$^6$R$^7$,
$(CH_2)_n$—SO$_2$NR$^6$R$^7$,
$(CH_2)_n$—SO$_2$R$^9$,
$(CH_2)_n$—NR$^8$SO$_2$R$^9$,
$(CH_2)_n$—NR$^8$CONR$^6$R$^7$,
$(CH_2)_n$—NR$^8$COR$^8$,
$(CH_2)_n$—NR$^8$CO$_2$R$^9$,
$(CH_2)_n$—COOH,
$(CH_2)_n$—COO$C_{1-6}$ alkyl,
$(CH_2)_n$-aryl, wherein aryl is unsubstituted or substituted with one to five substituents independently selected from halogen, hydroxy, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens, (CH$_2$)$_n$-heterocyclyl, wherein heterocyclyl is unsubstituted or substituted with one to three substituents independently selected from oxo, hydroxy, halogen, CO$_2$H, C$_{1-6}$ alkyloxycarbonyl, C$_{1-6}$ alkyl, C$_{3-6}$ cycloalkyl, and C$_{1-6}$ alkoxy, wherein alkyl and alkoxy are unsubstituted or substituted with one to five halogens, (CH$_2$)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens, wherein any methylene (CH$_2$) carbon atom in R$^5$ is unsubstituted or substituted with one to two groups independently selected from halogen, hydroxy, and C$_{1-4}$ alkyl unsubstituted or substituted with one to five halogens;

each R$^9$ is independently selected from the group consisting of tetrazolyl, thiazolyl, (CH$_2$)$_n$-phenyl, (CH$_2$)$_n$—C$_{3-6}$ cycloalkyl, and C$_{1-6}$ alkyl, wherein alkyl is unsubstituted or substituted with one to five halogens and wherein phenyl and cycloalkyl are unsubstituted or substituted with one to five substituents independently selected from halogen, hydroxy, C$_{1-6}$ alkyl, and C$_{1-6}$ alkoxy, wherein alkyl and alkoxy are unsubstituted or substituted with one to five halogens, and wherein any methylene (CH$_2$) carbon atom in R$^8$ is unsubstituted or substituted with one to two groups independently selected from halogen, hydroxy, and C$_{1-4}$ alkyl unsubstituted or substituted with one to five halogens; and each R$^8$ is hydrogen or R$^9$.

In one embodiment of the compounds of the present invention, the carbon atom marked with an * has the stereochemical configuration as depicted in formula Ia:

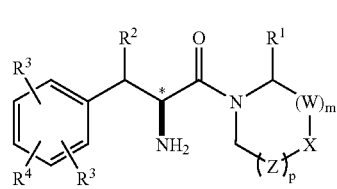

(Ia)

wherein R$^3$ is hydrogen or fluorine; and
W, X, Z, m, p, R$^1$, R$^2$, and R$^4$ are as defined above.

In a class of this embodiment of the compounds of the present invention, the carbon atom attached to R$^1$ marked with an ** has the stereochemical configuration as depicted in the formula Ib:

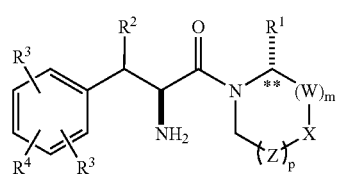

(Ib)

wherein R$^3$ is hydrogen or fluorine, and
W, X, Z, m, p, R$^1$, R$^2$, and R$^4$ are as defined above.

In a second embodiment of the compounds of the present invention, m is 1 and p is 0 as depicted in formula Ic:

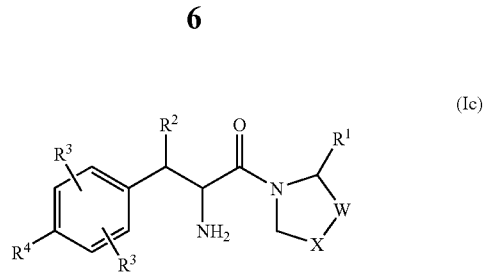

(Ic)

wherein R$^3$ is hydrogen or fluorine, and
W, X, R$^1$, R$^2$, and R$^4$ are as defined above.

A class of this embodiment encompasses compounds wherein the carbon atom marked with an * and the carbon atom marked with an ** have the stereochemical configurations as depicted in the formula Id:

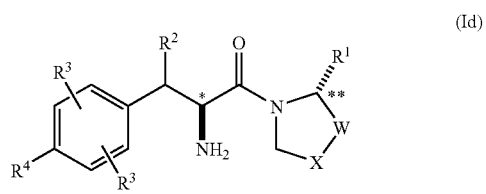

(Id)

wherein R$^3$ is hydrogen or fluorine, and W, X, R$^1$, R$^2$, and R$^4$ are as defined above.

In a subclass of this class of the compounds of the present invention, R$^1$ is hydrogen, W is CH$_2$, and X is CH$_2$, CHF or CF$_2$.

In a third embodiment of the compounds of the present invention, R$^1$ is hydrogen, X is CHF, and m and p are 0 as depicted in the formula Ie:

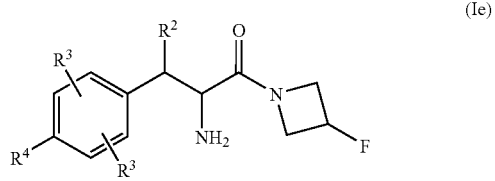

(Ie)

wherein R$^3$ is hydrogen or fluorine, and R$^2$ and R$^4$ are as defined above.

A class of this embodiment encompasses compounds wherein the carbon atom marked with an * has the stereochemical configuration as depicted in the formula If:

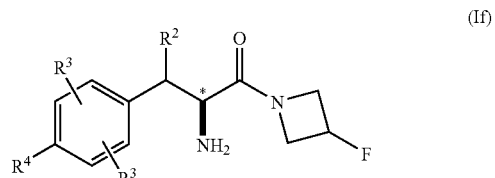

(If)

wherein R$^3$ is hydrogen or fluorine, and R$^2$ and R$^4$ are as defined above.

In a fourth embodiment of the compounds of the present invention, R$^1$ is hydrogen, and m and p are 1 as depicted in formula Ig:

(Ig)

wherein $R^3$ is hydrogen or fluorine; and
W, X, Z, $R^2$ and $R^4$ are as defined above.

A class of this embodiment encompasses compounds wherein the carbon atom marked with an * has the stereochemical configuration as depicted in the formula Ih:

(Ih)

wherein $R^3$ is hydrogen or fluorine, and W, X, Z, $R^2$, and $R^4$ are as defined above.

In a subclass of this class, W and Z are $CH_2$ and X is CHF or $CF_2$.

In a fifth embodiment of the compounds of the present invention, $R^2$ is selected from the group consisting of
- $C_{1-6}$ alkyl, wherein alkyl is unsubstituted or substituted with one to five substituents independently selected from halogen or hydroxy,
- $C_{2-6}$ alkenyl, wherein alkenyl is unsubstituted or substituted with one to five substituents independently selected from halogen or hydroxy,
- $(CH_2)_n$—$C_{3-6}$ cycloalkyl, wherein cycloalkyl is unsubstituted or substituted with one to three substituents independently selected from halogen, hydroxy, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
- $(CH_2)_n$COOH,
- $(CH_2)_n$COO$C_{1-6}$ alkyl,
- $(CH_2)_n$CONR$^6$R$^7$, wherein $R^6$ and $R^7$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
- or wherein $R^6$ and $R^7$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and wherein any methylene ($CH_2$) carbon atom in $R^2$ is unsubstituted or substituted with one to two groups independently selected from halogen, hydroxy, and $C_{1-4}$ alkyl unsubstituted or substituted with one to five halogens.

In a class of this embodiment of the compounds of the present invention, $R^2$ is selected from the group consisting of
- $C_{1-3}$ alkyl, wherein alkyl is unsubstituted or substituted with one to five substituents independently selected from halogen or hydroxy,
- $CH_2$—$C_{3-6}$ cycloalkyl,
- COOH,
- COO$C_{1-6}$ alkyl,
- CONR$^6$R$^7$, wherein $R^6$ and $R^7$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
- or wherein $R^6$ and $R^7$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

A sixth embodiment of the present invention encompasses compounds of structural formula Ii:

(Ii)

wherein X is $CH_2$, S, CHF, or $CF_2$;
W and Z are each independently $CH_2$, CHF, or $CF_2$;
$R^4$ is phenyl, heteroaryl, or heterocyclyl, wherein phenyl, heteroaryl, and heterocyclyl are unsubstituted or substituted with one to three $R^5$ substituents;
$R^2$ is selected from the group consisting of:
- methyl,
- ethyl,
- $CH_2$-cyclopropyl,
- COOH,
- COOMe,
- COOEt,
- CONHMe,
- CONMe$_2$,
- CONH$_2$,
- CONHEt,
- CONMeCH$_2$Ph,
- pyrrolidin-1-ylcarbonyl,
- azetidin-1-ylcarbonyl,
- 3-fluoroazetidin-1-ylcarbonyl,
- morpholin-4-ylcarbonyl, and

[(tetrazol-5-yl)amino]carbonyl; and
each $R^5$ is independently selected from the group consisting of:
halogen,
cyano,
oxo,
hydroxy,
$C_{1-6}$ alkyl, wherein alkyl is unsubstituted or substituted with one to five halogens,
$C_{1-6}$ alkoxy, wherein alkoxy is unsubstituted or substituted with one to five halogens,
$NR^6R^7$,
$CONR^6R^7$,
$OCONR^6R^7$,
$SO_2NR^6R^7$,
$SO_2R^9$,
$NR^8SO_2R^9$,
$NR^8CONR^6R^7$,
$NR^8COR^8$,
$NR^8CO_2R^9$,
COOH,
$COOC_{1-6}$ alkyl,
  aryl, wherein aryl is unsubstituted or substituted with one to five substituents independently selected from halogen, hydroxy, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, and
  $(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens.

In a class of this embodiment, each $R^5$ is independently selected from the group consisting of:
halogen,
cyano,
oxo,
$C_{1-6}$ alkyl, wherein alkyl is unsubstituted or substituted with one to five halogens,
$C_{1-6}$ alkoxy, wherein alkoxy is unsubstituted or substituted with one to five halogens,
$CONR^6R^7$,
$NR^8COR^8$,
$SO_2R^9$,
$NR^8SO_2R^9$,
COOH,
$COOC_{1-6}$ alkyl,
heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens, and
heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens.

In a subclass of this class, $R^4$ is selected from the group consisting of:
4-fluorophenyl,
2,4-difluorophenyl,
3,4-difluorophenyl,
2-chlorophenyl,
2-fluorophenyl,
3-(methylsulfonyl)phenyl,
3-(ethoxycarbonyl)phenyl,
3-carboxyphenyl,
3-(aminocarbonyl)phenyl,
3-[(tert-butylamino)carbonyl]phenyl,
3-[(phenylamino)carbonyl]phenyl,
3-[(thiazol-2-ylamino)carbonyl]phenyl,
3-[(tetrazol-5-ylamino)carbonyl]phenyl,
3-[[(trifluoromethyl)sulfonyl]amino]phenyl,
3-(tetrazol-5-yl)phenyl,
4-fluoro-3-(tetrazol-5-yl)phenyl,
2-fluoro-5-(tetrazol-5-yl)phenyl,
3-(5-oxo-4,5-dihydro-1,2,4-oxadiazol-3-yl)phenyl,
4-fluoro-3-(5-oxo-4,5-dihydro-1,2,4-oxadiazol-3-yl)phenyl,
3-(5-oxo-4,5-dihydro-1,3,4-oxadiazol-2-yl)phenyl,
3-(5-oxo-4,5-dihydro-1H-1,2,4-triazol-3-yl)phenyl,
3-(1,3,4-oxadiazol-2-yl)phenyl,
3-(1,2,4-triazol-3-yl)phenyl,
3-[5-(trifluoromethyl)-1,2,4-triazol-3-yl]phenyl,
3-(5-ethoxy-1,2,4-triazol-3-yl)phenyl,
pyridin-3-yl,
6-fluoro-pyridin-3-yl,
6-methoxypyridin-3-yl,
6-oxo-1,6-dihydropyridin-3-yl,
1-methyl-6-oxo-1,6-dihydropyridin-3-yl,
1-ethyl-6-oxo-1,6-dihydropyridin-3-yl,
5-bromo-1-methyl-6-oxo-1,6-dihydropyridin-3-yl,
imidazo[1,2-α]pyridin-6-yl,
[1,2,4]triazolo[4,3-α]pyridin-6-yl,
3-(trifluoromethyl)[1,2,4]triazolo[4,3-α]pyridin-6-yl,
3-oxo-2,3-dihydro[1,2,4]triazolo[4,3-α]pyridin-6-yl,
2-methyl-3-oxo-2,3-dihydro[1,2,4]triazolo[4,3-α]pyridin-6-yl,
4-aminoquinazolin-6-yl,
2-(acetylamino)imidazo[1,2-α]pyridin-6-yl,
3-aminoimidazo[1,2-α]pyridin-6-yl,
3-carboxypyrazolo[1,5-α]pyridin-5-yl,
5-bromo-6-oxo-1,6-dihydropyridin-3-yl,
[1,2,4]triazolo[1,5-α]pyridin-6-yl,
[1,2,4]triazolo[1,5-α]pyridin-7-yl, and
pyrazolo[1,5-α]pyrimidin-5-yl.

Another class of this embodiment encompasses compounds of the structural Ij:

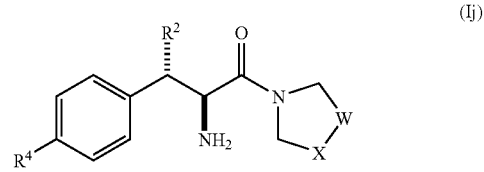

(Ij)

$R^2$ is selected from the group consisting of:
  methyl,
  ethyl,
  $CH_2$-cyclopropyl,
  COOH,
  COOMe,
  COOEt,
  CONHMe,
  $CONMe_2$,
  $CONH_2$,
  CONHEt,
  $CONMeCH_2Ph$,
  pyrrolidin-1-ylcarbonyl,
  azetidin-1-ylcarbonyl,
  3-fluoroazetidin-1-ylcarbonyl,
  morpholin-4-ylcarbonyl, and
  [(tetrazol-5-yl)amino]carbonyl; and
$R^4$ is selected from the group consisting of
  4-fluorophenyl,
  2,4-difluorophenyl,
  3,4-difluorophenyl,
  2-chlorophenyl,
  2-fluorophenyl,
  3-(methylsulfonyl)phenyl,
  3-(ethoxycarbonyl)phenyl,
  3-carboxyphenyl,
  3-(aminocarbonyl)phenyl,
  3-[(tert-butylamino)carbonyl]phenyl,
  3-[(phenylamino)carbonyl]phenyl,
  3-[(thiazol-2-ylamino)carbonyl]phenyl,
  3-[(tetrazol-5-ylamino)carbonyl]phenyl,
  3-[[(trifluoromethyl)sulfonyl]amino]phenyl,
  3-(tetrazol-5-yl)phenyl,
  4-fluoro-3-(tetrazol-5-yl)phenyl,
  2-fluoro-5-(tetrazol-5-yl)phenyl,
  3-(5-oxo-4,5-dihydro-1,2,4-oxadiazol-3-yl)phenyl,
  4-fluoro-3-(5-oxo-4,5-di hydro-1,2,4-oxadiazol-3-yl)phenyl,
  3-(5-oxo-4,5-dihydro-1,3,4-oxadiazol-2-yl)phenyl,
  3-(5-oxo-4,5-dihydro-1H-1,2,4-triazol-3-yl)phenyl,
  3-(1,3,4-oxadiazol-2-yl)phenyl,
  3-(1,2,4-triazol-3-yl)phenyl,
  3-[5-(trifluoromethyl)-1,2,4-triazol-3-yl]phenyl,
  3-(5-ethoxy-1,2,4-triazol-3-yl)phenyl,
  pyridin-3-yl,
  6-fluoro-pyridin-3-yl,
  6-methoxypyridin-3-yl,
  6-oxo-1,6-dihydropyridin-3-yl,
  1-methyl-6-oxo-1,6-dihydropyridin-3-yl,
  1-ethyl-6-oxo-1,6-dihydropyridin-3-yl,
  5-bromo-1-methyl-6-oxo-1,6-dihydropyridin-3-yl,
  imidazo[1,2-α]pyridin-6-yl,
  [1,2,4]triazolo[4,3-α]pyridin-6-yl,
  3-(trifluoromethyl)[1,2,4]triazolo[4,3-α]pyridin-6-yl,
  3-oxo-2,3-dihydro[1,2,4]triazolo[4,3-α]pyridin-6-yl,
  2-methyl-3-oxo-2,3-dihydro[1,2,4]triazolo[4,3-α]pyridin-6-yl,
  4-aminoquinazolin-6-yl,
  2-(acetylamino)imidazo[1,2-α]pyridin-6-yl,
  3-aminoimidazo[1,2-α]pyridin-6-yl,
  3-carboxypyrazolo[1,5-α]pyridin-5-yl,
  5-bromo-6-oxo-1,6-dihydropyridin-3-yl,
  [1,2,4]triazolo[1,5-α]pyridin-6-yl,
  [1,2,4]triazolo[1,5-α]pyridin-7-yl, and
  pyrazolo[1,5-α]pyrimidin-5-yl.
In a subclass of this class, W is $CH_2$ and X is CHF or $CF_2$.

Illustrative, but nonlimiting examples, of compounds of the present invention that are useful as dipeptidyl peptidase-IV inhibitors are the following:

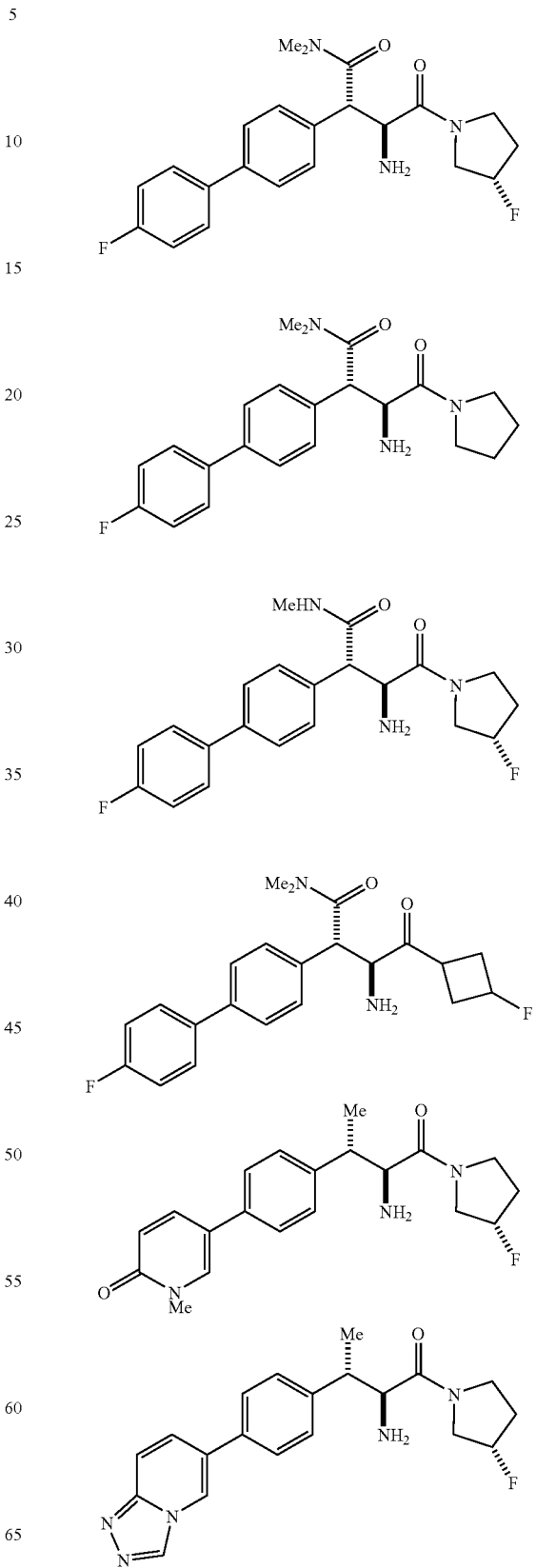

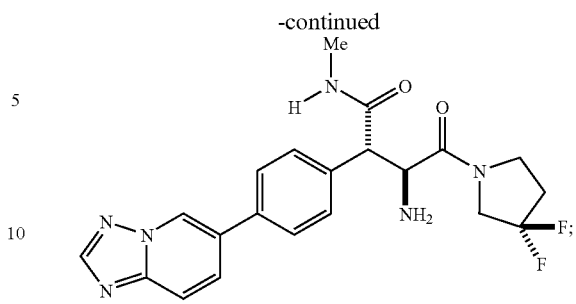
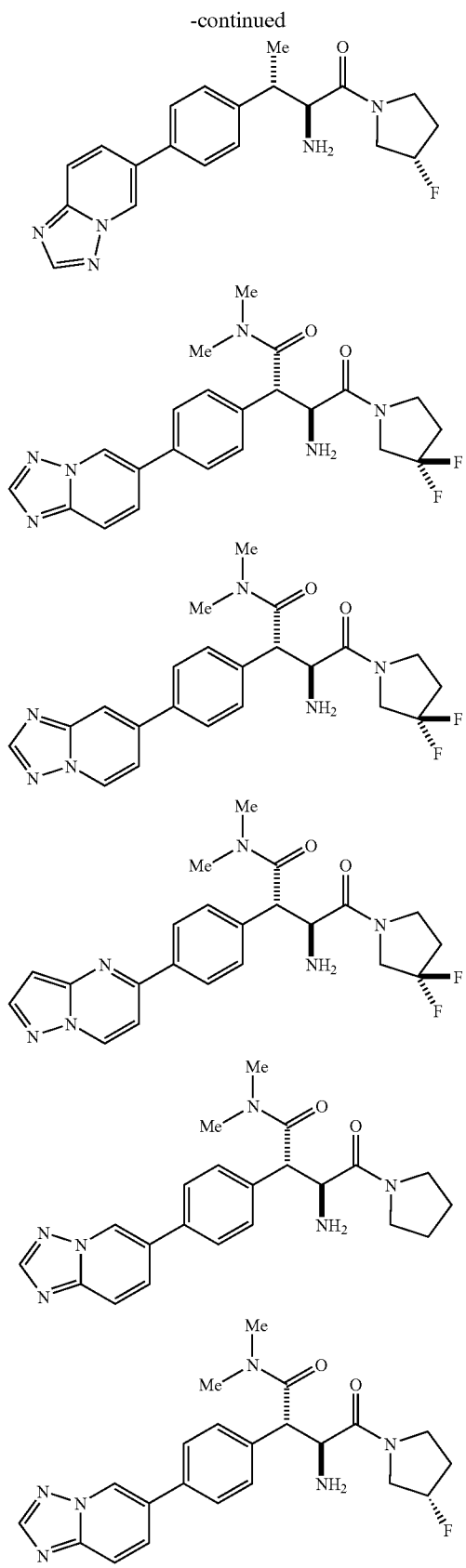

or a pharmaceutically acceptable salt thereof.

As used herein the following definitions are applicable.

"Alkyl", as well as other groups having the prefix "alk", such as alkoxy and alkanoyl, means carbon chains which may be linear or branched, and combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like. Where the specified number of carbon atoms permits, e.g., from $C_{3-10}$, the term alkyl also includes cycloalkyl groups, and combinations of linear or branched alkyl chains combined with cycloalkyl structures. When no number of carbon atoms is specified, $C_{1-6}$ is intended.

"Cycloalkyl" is a subset of alkyl and means a saturated carbocyclic ring having a specified number of carbon atoms. Examples of cycloalkyl include cyclopropyl, cyclobutyl, cyclopentyl, cyclohexyl, cycloheptyl, cyclooctyl, and the like. A cycloalkyl group generally is monocyclic unless stated otherwise. Cycloalkyl groups are saturated unless otherwise defined.

The term "alkoxy" refers to straight or branched chain alkoxides of the number of carbon atoms specified (e.g., $C_{1-6}$ alkoxy), or any number within this range [i.e., methoxy (MeO—), ethoxy, isopropoxy, etc.].

The term "alkylthio" refers to straight or branched chain alkylsulfides of the number of carbon atoms specified (e.g., $C_{1-6}$ alkylthio), or any number within this range [i.e., methylthio (MeS—), ethylthio, isopropylthio, etc.].

The term "alkylamino" refers to straight or branched alkylamines of the number of carbon atoms specified (e.g., $C_{1-6}$ alkylamino), or any number within this range [i.e., methylamino, ethylamino, isopropylamino, t-butylamino, etc.].

The term "alkylsulfonyl" refers to straight or branched chain alkylsulfones of the number of carbon atoms specified (e.g., $C_{1-6}$ alkylsulfonyl), or any number within this range [i.e., methylsulfonyl (MeSO$_2$—), ethylsulfonyl, isopropylsulfonyl, etc.].

The term "alkyloxycarbonyl" refers to straight or branched chain esters of a carboxylic acid derivative of the present invention of the number of carbon atoms specified (e.g., $C_{1-6}$ alkyloxycarbonyl), or any number within this range [i.e., methyloxycarbonyl (MeOCO—), ethyloxycarbonyl, or butyloxycarbonyl].

"Aryl" means a mono- or polycyclic aromatic ring system containing carbon ring atoms. The preferred aryls are monocyclic or bicyclic 6–10 membered aromatic ring systems. Phenyl and naphthyl are preferred aryls. The most preferred aryl is phenyl.

"Heterocycle" and "heterocyclyl" refer to saturated or unsaturated non-aromatic rings or ring systems containing at least one heteroatom selected from O, S and N, further and including the oxidized forms of sulfur, namely SO and $SO_2$. Examples of heterocycles include tetrahydrofuran (THF), dihydrofuran, 1,4-dioxane, morpholine, 1,4-dithiane, piperazine, piperidine, 1,3-dioxolane, imidazolidine, imidazoline, pyrroline, pyrrolidine, tetrahydropyran, dihydropyran, oxathiolane, dithiolane, 1,3-dioxane, 1,3-dithiane, oxathiane, thiomorpholine, and the like.

"Heteroaryl" means an aromatic or partially aromatic heterocycle that contains at least one ring heteroatom selected from O, S and N. Heteroaryls also include heteroaryls fused to other kinds of rings, such as aryls, cycloalkyls and heterocycles that are not aromatic. Examples of heteroaryl groups include pyrrolyl, isoxazolyl, isothiazolyl, pyrazolyl, pyridinyl, 2-oxo-(1H)-pyridinyl (2-hydroxy-pyridinyl), oxazolyl, 1,2,4-oxadiazolyl, 1,3,4-oxadiazolyl, thiadiazolyl, thiazolyl, imidazolyl, triazolyl, tetrazolyl, furyl, triazinyl, thienyl, pyrimidinyl, pyrazinyl, benzisoxazolyl, benzoxazolyl, benzothiazolyl, benzothiadiazolyl, dihydrobenzofuranyl, indolinyl, pyridazinyl, indazolyl, isoindolyl, dihydrobenzothienyl, indolizinyl, cinnolinyl, phthalazinyl, quinazolinyl, naphthyridinyl, carbazolyl, benzodioxolyl, quinoxalinyl, purinyl, furazanyl, isobenzylfuranyl, benzimidazolyl, benzofuranyl, benzothienyl, quinolyl, indolyl, isoquinolyl, dibenzofuranyl, imidazo[1,2-α]pyridinyl, [1,2,4-triazolo][4,3-α]pyridinyl, pyrazolo[1,5-α]pyridinyl, [1,2,4-triazolo][1,5-α]pyridinyl, 2-oxo-1,3-benzoxazolyl, 4-oxo-3H-quinazolinyl, 3-oxo-[1,2,4]-triazolo[4,3-α]-2H-pyridinyl, 5-oxo-[1,2,4]-4H-oxadiazolyl, 2-oxo-[1,3,4]-3H -oxadiazolyl, 2-oxo-1,3-dihydro-2H-imidazolyl, 3-oxo-2,4-dihydro-3H-1,2,4-triazolyl, and the like. For heterocyclyl and heteroaryl groups, rings and ring systems containing from 3–15 atoms are included, forming 1–3 rings.

"Halogen" refers to fluorine, chlorine, bromine and iodine. Chlorine and fluorine are generally preferred. Fluorine is most preferred when the halogens are substituted on an alkyl or alkoxy group (e.g. $CF_{3O}$ and $CF_3CH_2O$).

The compounds of the present invention may contain one or more asymmetric centers and can thus occur as racemates and racemic mixtures, single enantiomers, diastereomeric mixtures and individual diastereomers. The compounds of the present invention have one asymmetric center at the carbon atom marked with an * in formula Ia. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

Formula I shows the structure of the class of compounds without preferred stereochemistry. Formula Ia shows the preferred sterochemistry at the carbon atom to which is attached the amino group of the beta amino acid from which these compounds are prepared.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

It will be understood that, as used herein, references to the compounds of structural formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, the following: acetate, benzenesulfonate, benzoate, bicarbonate, bisulfate, bitartrate, borate, bromide, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, oleate, oxalate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as acetate or maleate, can be employed. Included are those esters and acyl groups known in the art for modifying the solubility or hydrolysis characteristics for use as sustained-release or prodrug formulations.

Solvates, and in particular, the hydrates of the compounds of structural formula I are included in the present invention as well.

Exemplifying the invention is the use of the compounds disclosed in the Examples and herein.

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens):

The present invention is further directed to a method for the manufacture of a medicament for inhibiting dipeptidyl peptidase-IV enzyme activity in humans and animals comprising combining a compound of the present invention with a pharmaceutically acceptable carrier or diluent.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

The utility of the compounds in accordance with the present invention as inhibitors of dipeptidyl peptidase-IV enzyme activity may be demonstrated by methodology known in the art. Inhibition constants are determined as follows. A continuous fluorometric assay is employed with the substrate Gly-Pro-AMC, which is cleaved by DP-IV to release the fluorescent AMC leaving group. The kinetic parameters that describe this reaction are as follows: $K_m$=50 µM; $k_{cat}$=75 s$^{-1}$; $k_{cat}/K_m$=1.5×10$^6$ M$^{-1}$s$^{-1}$. A typical reaction contains approximately 50 pM enzyme, 50 µM Gly-Pro-AMC, and buffer (100 mM HEPES, pH 7.5, 0.1 mg/ml BSA) in a total reaction volume of 100 µl. Liberation of AMC is monitored continuously in a 96-well plate fluorometer using an excitation wavelength of 360 nm and an emission wavelength of 460 nm. Under these conditions, approximately 0.8 µM AMC is produced in 30 minutes at 25 degrees C. The enzyme used in these studies was soluble (transmembrane domain and cytoplasmic extension excluded) human protein produced in a baculovirus expression system (Bac-To-Bac, Gibco BRL). The kinetic constants for hydrolysis of Gly-Pro-AMC and GLP-1 were found to be in accord with literature values for the native enzyme. To measure the dissociation constants for compounds, solutions of inhibitor in DMSO were added to reactions containing enzyme and substrate (final DMSO concentration is 1%). All experiments were conducted at room temperature using the standard reaction conditions described above. To determine the dissociation constants ($K_i$), reaction rates were fit by non-linear regression to the Michaelis-Menton equation for competitive inhibition. The errors in reproducing the dissociation constants are typically less than two-fold.

In particular, the compounds of the following examples had activity in inhibiting the dipeptidyl peptidase-IV enzyme in the aforementioned assays, generally with an $IC_{50}$ of less than about 1 µM. Such a result is indicative of the intrinsic activity of the compounds in use as inhibitors the dipeptidyl peptidase-IV enzyme activity.

Dipeptidyl peptidase-IV enzyme (DP-IV) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DP-IV is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions.

Type 2 Diabetes and Related Disorders: It is well established that the incretins GLP-1 and GIP are rapidly inactivated in vivo by DP-IV. Studies with DP-IV$^{(-/-)}$-deficient mice and preliminary clinical trials indicate that DP-IV inhibition increases the steady state concentrations of GLP-1 and GIP, resulting in improved glucose tolerance. By analogy to GLP-1 and GIP, it is likely that other glucagon family peptides involved in glucose regulation are also inactivated by DP-IV (eg. PACAP). Inactivation of these peptides by DP-IV may also play a role in glucose homeostasis.

The DP-IV inhibitors of the present invention therefore have utility in the treatment of Type 2 diabetes and in the treatment and prevention of the numerous conditions that often accompany Type 2 diabetes, including metabolic syndrome X, reactive hypoglycemia, and diabetic dyslipidemia. Obesity, discussed below, is another condition that is often found with Type 2 diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) hypertension (24) Syndrome X, (25) ovarian hyperandrogenism (polycystic ovarian syndrome), and other disorders where insulin resistance is a component.

Obesity: DP-IV inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910–R916 (1999)). ICV administration of GLP-1 in rats and mice also has profound effects on food intake (*Nature Medicine*, 2: 1254–1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DP-IV. ICV administration of GLP-2 also inhibits food intake, analogous to the effects observed with GLP-1 (*Nature Medicine*, 6: 802–807 (2000)). In addition, studies with DP-IV deficient mice suggest that these animals are resistant to diet-induced obesity and associated pathology (e.g. hyperinsulinonemia).

Growth Hormone Deficiency: DP-IV inhibition may be useful for the treatment of growth hormone deficiency, based on the hypothesis that growth-hormone releasing factor (GRF), a peptide that stimulates release of growth hormone from the anterior pituitary, is cleaved by the DP-IV enzyme in vivo (WO 00/56297). The following data provide evidence that GRF is an endogenous substrate: (1) GRF is efficiently cleaved in vitro to generate the inactive product GRF[3–44] (*BBA* 1122: 147–153 (1992)); (2) GRF is rapidly degraded in plasma to GRF[3–44]; this is prevented by the DP-IV inhibitor diprotin A; and (3) GRF[3–44] is found in the plasma of a human GRF transgenic pig (*J. Clin. Invest.*, 83: 1533–1540 (1989)). Thus DP-IV inhibitors may be useful for the same spectrum of indications which have been considered for growth hormone secretagogues.

Intestinal Injury: The potential for using DP-IV inhibitors for the treatment of intestinal injury is suggested by the results of studies indicating that glucagon-like peptide-2 (GLP-2), a likely endogenous substrate for DP-IV, may exhibit trophic effects on the intestinal epithelium (*Regulatory Peptides*, 90: 27–32 (2000)). Administration of GLP-2 results in increased small bowel mass in rodents and attenuates intestinal injury in rodent models of colitis and enteritis.

Immunosuppression: DP-IV inhibition may be useful for modulation of the immune response, based upon studies implicating the DP-IV enzyme in T cell activation and in chemokine processing, and efficacy of DP-IV inhibitors in in vivo models of disease. DP-IV has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DP-IV. In several cases (RANTES, LD78-beta, MDC, eotaxin, SD-1 alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DP-IV hydrolysis.

DP-IV inhibitors have been shown to be efficacious immunosupressants in animal models of transplantation and arthritis. Prodipine (Pro-Pro-diphenyl-phosphonate), an irreversible inhibitor of DP-IV, was shown to double cardiac allograft survival in rats from day 7 to day 14 (*Transplantation*, 63: 1495–1500 (1997)). DP-IV inhibitors have been tested in collagen and alkyldiamine-induced arthritis in rats and showed a statistically significant attenuation of hind paw swelling in this model [*Int. J. Immunopharmacology*, 19:15–24 (1997) and *Immunopharmacology*, 40: 21–26 (1998)]. DP-IV is upregulated in a number of autoimmune diseases including rheumatoid arthritis, multiple sclerosis, Graves' disease, and Hashimoto's thyroiditis (*Immunology Today*, 20: 367–375 (1999)).

HIV Infection: DP-IV inhibition may be useful for the treatment or prevention of HIV infection or AIDS because a number of chemokines which inhibit HIV cell entry are potential substrates for DP-IV (*Immunology Today* 20: 367–375 (1999)). In the case of SDF-1alpha, cleavage decreases antiviral activity (*PNAS*, 95: 6331–6 (1998)). Thus, stabilization of SDF-1alpha through inhibition of DP-IV would be expected to decrease HIV-infectivity.

Hematopolesis: DP-IV inhibition may be useful for the treatment or prevention of hematopiesis because DP-IV may be involved in hematopoiesis. A DP-IV inhibitor, Val-Boro-Pro, stimulated hematopoiesis in a mouse model of cyclophosphamide-induced neutropenia (WO 99/56753).

Neuronal Disorders: DP-IV inhibition may be useful for the treatment or prevention of various neuronal or psychiatric disorders because a number of peptides implicated in a variety of neuronal processes are cleaved in vitro by DP-IV. A DP-IV inhibitor thus may have a therapeutic benefit in the treatment of neuronal disorders. Endomorphin-2, beta-casomorphin, and substance P have all been shown to be in vitro substrates for DP-IV. In all cases, in vitro cleavage is highly efficient, with $k_{cat}/K_m \sim 10^6 M^{-1} s^{-1}$ or greater. In an electric shock jump test model of analgesia in rats, a DP-IV inhibitor showed a significant effect that was independent of the presence of exogenous endomorphin-2 (*Brain Research*, 815: 278–286 (1999)). Neuroprotective and neuroregenerative effects of DP-IV inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl Peptidase-IV In Vitro and In Vivo," *Int. Conf. On Dipeptidyl Aminopeptidases: Basic Science and Clinical Applications*, Sep. 26–29, 2002 (Berlin, Germany)].

Anxiety

Rats naturally deficient in DP-IV have an anxiolytic phenotype (WO 02/34243; Karl et al., *Physiol. Behav.* 2003). DP-UV deficient mice also have an anxiolytic phenotype using the porsolt and light/dark models. Thus DP-IV inhibitors may prove useful for treating anxiety and related disorders.

Memory and Cognition

GLP-1 agonists are active in models of learning (passive avoidance, Morris water maze) and neuronal injury (kainate-induced neuronal apoptosis) as demonstrated by During et al. (*Nature Med.* 9: 1173–1179 (2003)). The results suggest a physiological role for GLP-1 in learning and neuroprotection. Stabilization of GLP-1 by DP-IV inhibitors are expected to show similar effects.

Tumor Invasion and Metastasis: DP-IV inhibition may be useful for the treatment or prevention of tumor invasion and metastasis because an increase or decrease in expression of several ectopeptidases including DP-IV has been observed during the transformation of normal cells to a malignant phenotype (*J. Exp. Med.*, 190: 301–305 (1999)). Up- or down-regulation of these proteins appears to be tissue and cell-type specific. For example, increased CD26/DP-IV expression has been observed on T cell lymphoma, T cell acute lymphoblastic leukemia, cell-derived thyroid carcinomas, basal cell carcinomas, and breast carcinomas. Thus, DP-IV inhibitors may have utility in the treatment of such carcinomas.

Benign Prostatic Hypertrophy: DP-IV inhibition may be useful for the treatment of benign prostatic hypertrophy because increased DP-UV activity was noted in prostate tissue from patients with BPH (*Eur. J. Clin. Chem. Clin. Biochem.*, 30: 333–338 (1992)).

Sperm motility/male contraception: DP-IV inhibition may be useful for the altering sperm motility and for male contraception because in seminal fluid, prostatosomes, prostate derived organelles important for sperm motility, possess very high levels of DP-IV activity (*Eur. J. Clin. Chem. Clin. Biochem.*, 30: 333–338 (1992)).

Gingivitis: DP-IV inhibition may be useful for the treatment of gingivitis because DP-IV activity was found in gingival crevicular fluid and in some studies correlated with periodontal disease severity (*Arch. Oral Biol.* 37: 167–173 (1992)).

Osteoporosis: DP-IV inhibition may be useful for the treatment or prevention of osteoporosis because GIP receptors are present in osteoblasts.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type 2 diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, and other conditions that may be treated or prevented by inhibition of DP-IV.

The subject compounds are further useful in a method for the prevention or treatment of the aforementioned diseases, disorders and conditions in combination with other agents.

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also includes therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of Formula I, and either administered separately or in the same pharmaceutical composition, include, but are not limited to:

(a) other dipeptidyl peptidase IV (DP-IV) inhibitors;

(b) insulin sensitizers including (i) PPARγ agonists such as the glitazones (e.g. troglitazone, pioglitazone, englitazone, MCC-555, rosiglitazone, and the like) and other PPAR ligands, including PPARα/γ dual agonists, such as KRP-297, and PPARα agonists such as fenofibric acid derivatives (gemfibrozil, clofibrate, fenofibrate and bezafibrate), (ii) biguanides such as metformin and phenformin, and (iii) protein tyrosine phosphatase-1B (PTP-1B) inhibitors;

(c) insulin or insulin mimetics;

(d) sulfonylureas and other insulin secretagogues, such as tolbutamide glyburide, glipizide, glimepiride, and meglitinides, such as repaglinide;

(e) α-glucosidase inhibitors (such as acarbose and miglitol);

(f) glucagon receptor antagonists such as those disclosed in WO 98/04528, WO 99/01423, WO 00/39088, and WO 00/69810;

(g) GLP-1, GLP-1 mimetics, and GLP-1 receptor agonists such as those disclosed in WO00/42026 and WO00/59887;

(h) GIP and GIP mimetics such as those disclosed in WO00/58360, and GIP receptor agonists;

(i) PACAP, PACAP mimetics, and PACAP receptor agonists such as those disclosed in WO 01/23420;

(j) cholesterol lowering agents such as (i) HMG-CoA reductase inhibitors (lovastatin, simvastatin, pravastatin, cerivastatin, fluvastatin, atorvastatin, itavastatin, and rosuvastatin, and other statins), (ii) sequestrants (cholestyramine, colestipol, and dialkylaminoalkyl derivatives of a cross-linked dextran), (iii) nicotinyl alcohol, nicotinic acid or a salt thereof, (iv) PPARα agonists such as fenofibric acid derivatives (gemfibrozil, clofibrate, fenofibrate and bezafibrate), (v) PPARα/γ dual agonists, such as KRP-297, (vi) inhibitors of cholesterol absorption, such as beta-sitosterol and ezetimibe, (vii) acyl CoA:cholesterol acyltransferase inhibitors, such as avasimibe, and (viii) antioxidants, such as probucol;

(k) PPARδ agonists, such as those disclosed in WO97/28149;

(l) antiobesity compounds such as fenfluramine, dexfenfluramine, phentermine, sibutramine, orlistat, neuropeptide $Y_1$ or $Y_5$ antagonists, CB1 receptor inverse agonists and antagonists, $\beta_3$ adrenergic receptor agonists, melanocortin-receptor agonists, in particular melanocortin-4 receptor agonists, ghrelin antagonists, and melanin-concentrating hormone (MCH) receptor antagonists;

(m) ileal bile acid transporter inhibitors;

(n) agents intended for use in inflammatory conditions such as aspirin, non-steroidal anti-inflammatory drugs, glucocorticoids, azulfidine, and selective cyclooxygenase-2 inhibitors; and (o) antihypertensive agents such as ACE inhibitors (enalapril, lisinopril, captopril, quinapril, tandolapril), A-II receptor blockers (losartan, candesartan, irbesartan, valsartan, telmisartan, eprosartan), beta blockers and calcium channel blockers.

Dipeptidyl peptidase-IV inhibitors that can be combined with compounds of structural formula I include those disclosed in WO 03/004498 (16 Jan. 2003); WO 03/004496 (16 Jan. 2003); EP 1 258 476 (20 Nov. 2002); WO 02/083128 (24 Oct. 2002); WO 02/062764 (15 Aug. 2002); WO 03/000250 (3 Jan. 2003); WO 03/002530 (9 Jan. 2003); WO 03/002531 (9 Jan. 2003); WO 03/002553 (9 Jan. 2003); WO 03/002593 (9 Jan. 2003); WO 03/000180 (3 Jan. 2003); and WO 03/000181 (3 Jan. 2003). Specific DP-IV inhibitor compounds include isoleucine thiazolidide; NVP-DPP728; P32/98; and LAF 237.

Antiobesity compounds that can be combined with compounds of structural formula I include fenfluramine, dexfenfluramine, phentermine, sibutramine, orlistat, neuropeptide $Y_1$ or $Y_5$ antagonists, cannabinoid CB1 receptor antagonists or inverse agonists, melanocortin receptor agonists, in particular, melanocortin-4 receptor agonists, ghrelin antagonists, and melanin-concentrating hormone (MCH) receptor antagonists. For a review of anti-obesity compounds that can be combined with compounds of structural formula I, see S. Chaki et al., "Recent advances in feeding suppressing agents: potential therapeutic strategy for the treatment of obesity," Expert Opin. Ther. Patents, 11: 1677–1692 (2001) and D. Spanswick and K. Lee, "Emerging antiobesity drugs," Expert Opin. Emerging Drugs, 8: 217–237 (2003).

Neuropeptide $Y_5$ antagonists that can be combined with compounds of structural formula I include those disclosed in U.S. Pat. No. 6,335,345 (1 Jan. 2002) and WO 01/14376 (1 Mar. 2001); and specific compounds identified as GW 59884A; GW 569180A; LY366377; and CGP-71683A.

Cannabinoid CB1 receptor antagonists that can be combined with compounds of formula I include those disclosed in PCT Publication WO 03/007887; U.S. Pat. No. 5,624,941, such as rimonabant; PCT Publication WO 02/076949, such as SLV-319; U.S. Pat. No. 6,028,084; PCT Publication WO 98/41519; PCT Publication WO 00/10968; PCT Publication WO 99/02499; U.S. Pat. Nos. 5,532,237; and 5,292,736.

Melanocortin receptor agonists that can be combined with compounds of structural formula I include those disclosed in WO 03/009.847 (6 Feb. 2003); WO 02/068388 (6 Sep. 2002); WO 99/64002 (16 Dec. 1999); WO 00/74679 (14 Dec. 2000); WO 01/70708 (27 Sep. 2001); and WO 01/70337 (27 Sep. 2001) as well as those disclosed in J. D. Speake et al., "Recent advances in the development of melanocortin-4 receptor agonists," Expert Opin. Ther. Patents, 12: 1631–1638 (2002).

The above combinations include combinations of a compound of the present invention not only with one other active compound, but also with two or more other active compounds. Non-limiting examples include combinations of compounds having Formula I with two or more active compounds selected from biguanides, sulfonylureas, HMG-CoA reductase inhibitors, PPAR agonists, PTP-1B inhibitors, other DP-IV inhibitors, and antiobesity compounds.

Likewise, compounds of the present invention may be used in combination with other drugs that are used in the treatment/prevention/suppression or amelioration of the diseases or conditions for which compounds of the present invention are useful. Such other drugs may be administered, by a route and in an amount commonly used therefor, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouth washes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the following Schemes and Examples. Starting materials are made according to procedures known in the art or as illustrated herein.

The compounds of the present invention can be prepared from alpha-amino acid intermediates such as those of formula II and substituted heterocyclic intermediates such as those of formula III, using standard peptide coupling conditions followed by deprotection,

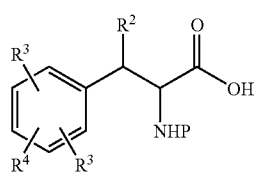

II

-continued

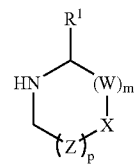

III where m, p, W, X, Z, $R^1$, $R^2$, $R^3$ and $R^4$ are as defined above and P is a suitable nitrogen protecting group such as tert-butoxycarbonyl (BOC), benzyloxycarbonyl (Cbz), or 9-fluorenylmethoxycarbonyl (Fmoc).

The preparation of these intermediates is described in the following Schemes.

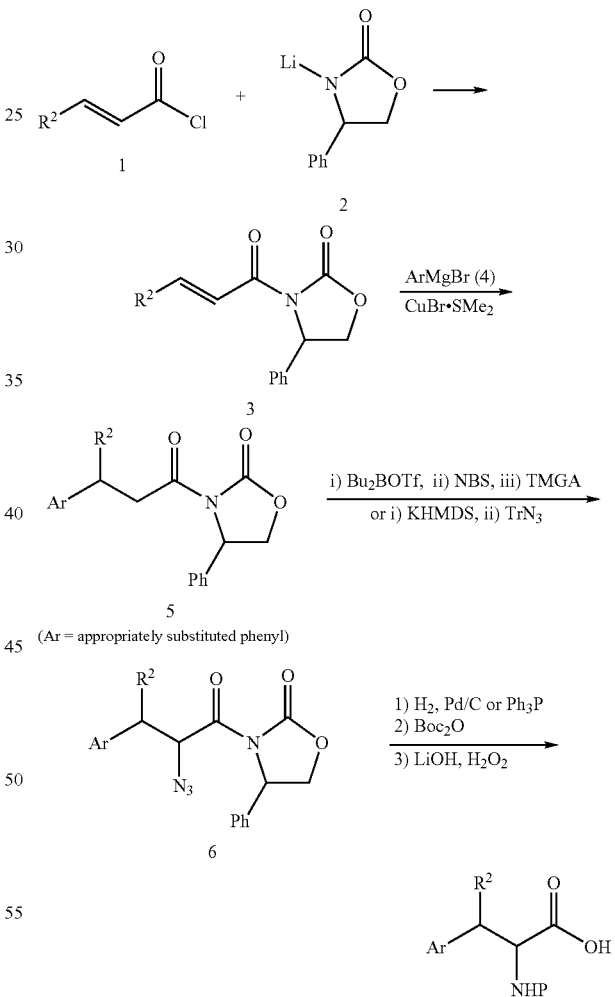

(Ar = appropriately substituted phenyl)

II

Compounds of formula II are commercially available, known in the literature or may be conveniently prepared by a variety of methods familiar to those skilled in the art. One convenient route described in the literature (X. Qian et al., *Tetrahedron* 1995, 51, 1033–1054) is illustrated in Scheme 1. An activated acid derivative, such as acid chloride 1, which may be commercially available or readily prepared from the corresponding acid, for example, by treatment with thionyl chloride or oxalyl chloride, is treated the lithium anion of phenyloxazolidinone 2 to provide acyl oxazolidinone 3. Conjugate addition of the appropriate aryl Grignard reagent 4 to oxazolidinone 3 provides intermediate 5. An alpha-azido moiety may be introduced in one of two convenient ways. First, the boron enolate generated from acyl oxazolidinone 5 by treatment with boron triflate and a base such as triethylamine or N,N-diisopropylethylamine is brominated by reaction with N-bromosuccinimide. The resultant bromide is displaced with azide, for example, by treatment with tetramethylguanidinium azide to provide azide 6. Alternatively, the potassium enolate of acyl oxazolidinone 5, generated for example with potassium hexamethyldisilazane, may be reacted with 2,4,6-triisopropylbenzenesulfonyl azide (trisyl azide) to provide azide 6 directly. The azide is reduced by catalytic hydrogenation or by treatment with triphenylphosphine and the resultant amine protected with an appropriate group, for example, as its N-tert-butyloxycarbonyl(Boc) derivative by treatment with di-tert-butyldicarbonate. The oxazolidinone is hydrolyzed, conveniently by treatment with lithium hydroperoxide, to provide the desired acid intermediate II. As will be readily apparent to those skilled in the art, all four diastereomers of acid II are available in enantiomerically pure form via this route, through the appropriate selection of either the (R) or (S) enantiomer of oxazolidinone 2 and employing the appropriate method for conversion of acyl oxazolidinone 5 to azide 6.

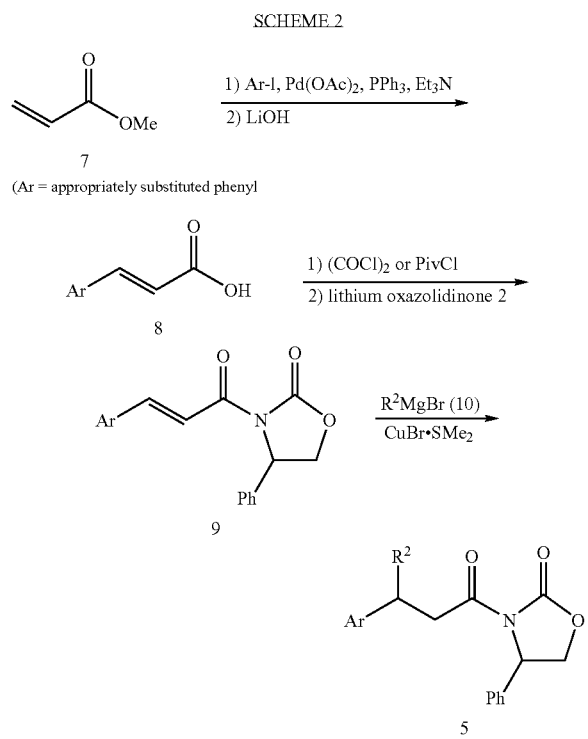

The aryl and R² substituent in intermediate 5 may be introduced in the reverse order, as illustrated in Scheme 2. Acid 8 is commercially available or readily prepared by a variety of methods known to those skilled in the art. In one such method, methyl acrylate (7) is treated with an appropriately substituted iodobenzene (ArI) under Stille coupling conditions to provide acid 8 after hydrolysis of the ester. Activation of the acid, for example as its acid chloride by treatment with oxalyl chloride or as a mixed anhydride by reaction with pivaloyl chloride (PivCl), followed by treatment with lithium oxazolidinone 2 gives acyl oxazolidinone 9. Copper catalyzed addition of the appropriate Grignard reagent 10 gives the desired intermediate 5. Conversion to intermediate II may be carried out as described in Scheme 1.

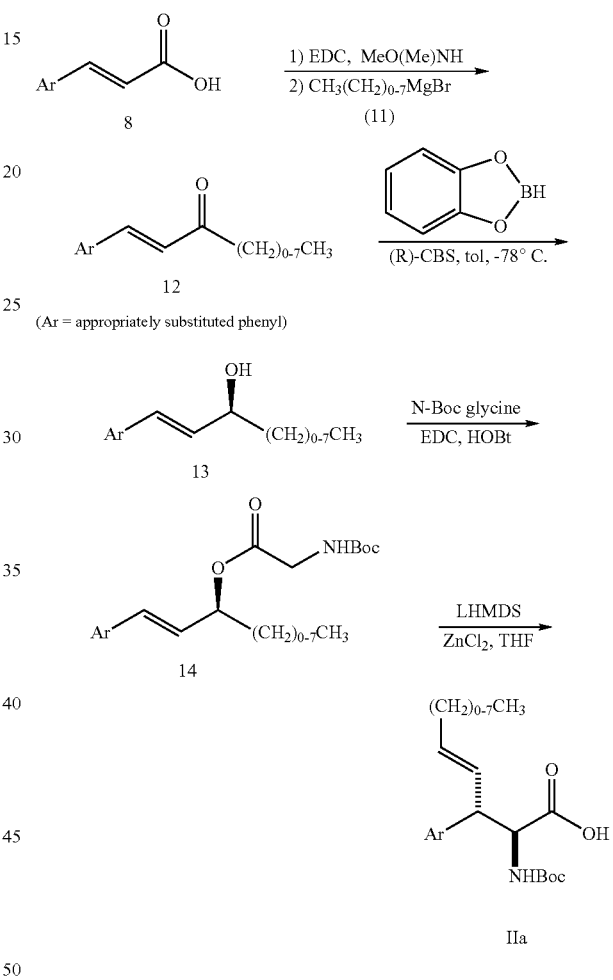

An alternate method for the preparation of intermediate II wherein R² contains an optionally substituted alkenyl group, and R² and the protected amine are anti to each other is shown in Scheme 3. Acid 8 may undergo EDC-mediated coupling to N,O-dimethylhydroxylamine followed by treatment with the appropriate Grignard reagent 11 to provide ketone 12. Reduction to alcohol 13 may be achieved in an asymmetric fashion by treatment with catecholborane in the presence of, for example, the (R) isomer of the CBS catalyst as described by E. J. Corey in *Tetrahedron Lett.* 36: 9153–9156 (1995). The alcohol is coupled to N-Boc glycine to provide ester 14. [3,3]-Sigmatropic rearrangement of the enolate of ester 14 may be achieved as described by U. Kazmaier in *Angew. Chem. Int. Ed. Eng.*, 33: 998–999 (1994) to provide intermediate IIa.

SCHEME 4

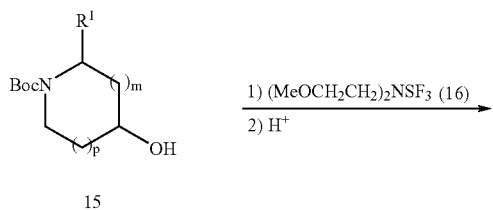

15

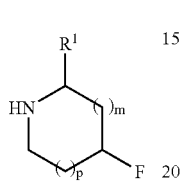

IIIa

Compounds of formula III are commercially available, known in the literature or may be conveniently prepared by a variety of methods familiar to those skilled in the art. One convenient method for the preparation of intermediate III wherein X is CHF and W and Z are CH$_2$ is shown in Scheme 4. An appropriately protected alcohol 15, which itself is known in the literature or may be conveniently prepared by a variety of methods familiar to those skilled in the art, is treated with a fluorinating reagent such as (diethylamino) sulfur trifluoride (DAST) or [bis(2-methoxyethyl)amino] sulfur trifluoride (16) to provide, after deprotection, the fluoro intermediate IIIa.

SCHEME 5

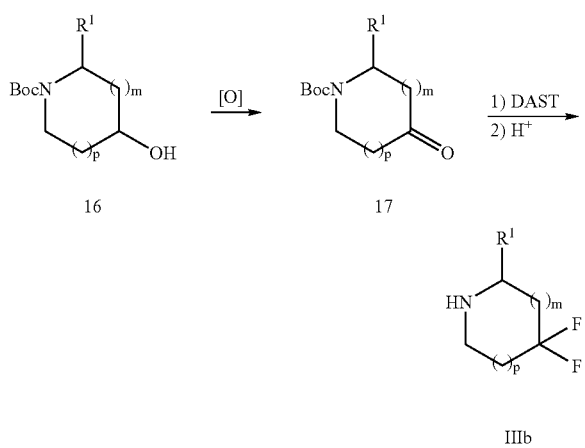

A method for the preparation of intermediate III wherein X is CF$_2$ and W and Z are CH$_2$ is shown in Scheme 5. An appropriately protected alcohol 16 is oxidized to the corresponding ketone 17 by a variety of methods known to those skilled in the art. Ketone 17 is treated with a fluorinating reagent, such as DAST, to provide, after deprotection, the fluoro intermediate IIIb.

SCHEME 6

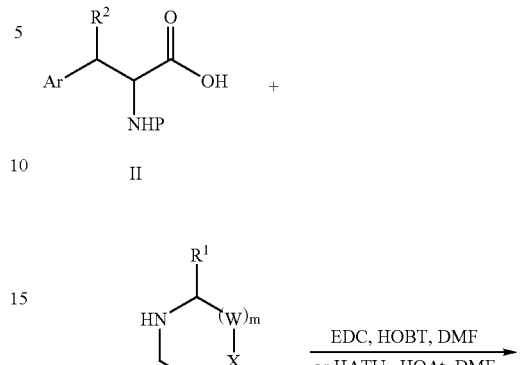

(Ar = appropriately substituted phenyl)

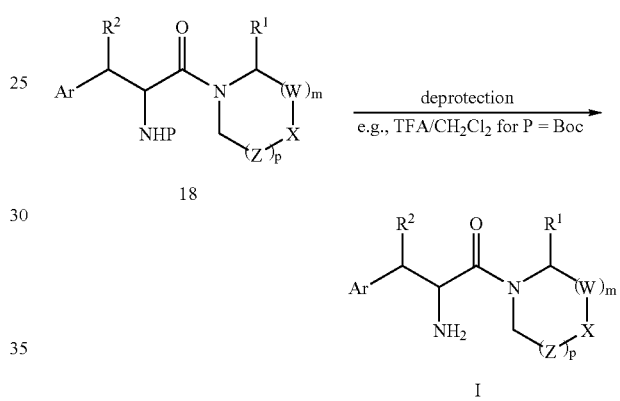

Intermediates II and III are coupled under standard peptide coupling conditions, for example, using 1-ethyl-3-(3-dimethylaminopropyl)carbodiimide and 1-hydroxybenzotriazole (EDC/HOBT) or O-(7-azabenzotriazol-1-yl)-N,N,N',N'-tetramethyluronium hexafluorophosphate and 1-hydroxy-7-azabenzotriazole (HATU/HOAT) in a solvent such as N,N-dimethylformamide (DMF) or dichloromethane for 3 to 48 hours at ambient temperature to provide Intermediate 18 as shown in Scheme 6. In some cases, Intermediate III may be a salt, such as a hydrochloride or trifluoroacetic acid salt, and in these cases it is convenient to add a base, generally N,N-diisopropylethylamine, to the coupling reaction. The protecting group is then removed with, for example, trifluoroacetic acid or methanolic hydrogen chloride in the case of Boc to give the desired amine I. The product is purified from unwanted side products, if necessary, by recrystallization, trituration, preparative thin layer chromatography, flash chromatography on silica gel, such as with a Biotage® apparatus, or HPLC. Compounds that are purified by HPLC may be isolated as the corresponding salt. Purification of intermediates is achieved in the same manner.

In some cases the product I, prepared as described in Scheme 6, may be further modified, for example, by manipulation of substituents on Ar or R$^2$. These manipulations may include, but are not limited to, reduction, oxidation, alkylation, acylation, and hydrolysis reactions which are commonly known to those skilled in the art.

SCHEME 7

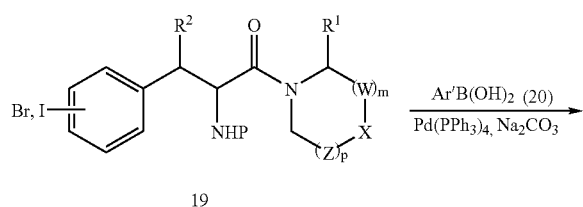

(Ar' = appropriately aryl, heteroaryl, or heterocyclyl)

One such example is illustrated in Scheme 7. Intermediate 19, wherein the phenyl substituent is a halogen such as bromide and iodide, is available following the route described above for the synthesis of intermediate 18. Coupling of bromide or iodide 19 and a boronic acid 20 in the presence of a palladium catalyst under Suzuki conditions provides intermediate 18. This is converted to product I as described in Scheme 6.

SCHEME 8

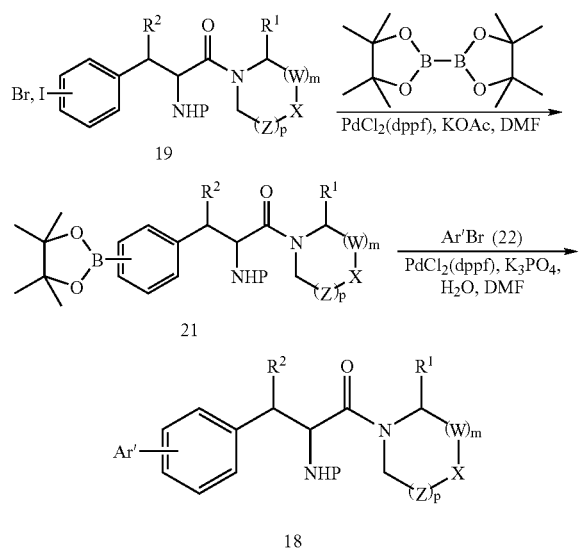

(Ar' = appropriately substituted aryl, heteroaryl, or heterocyclyl)

Another such example is illustrated in Scheme 8. Intermediate 19 is converted to the corresponding boronate ester 21. Boronate 21 may undergo Suzuki coupling with an appropriate halide, such as Ar'Br 22, in the presence of a palladium catalyst to provide the biaryl derivative 18. This is converted to product I as described in Scheme 6.

SCHEME 9

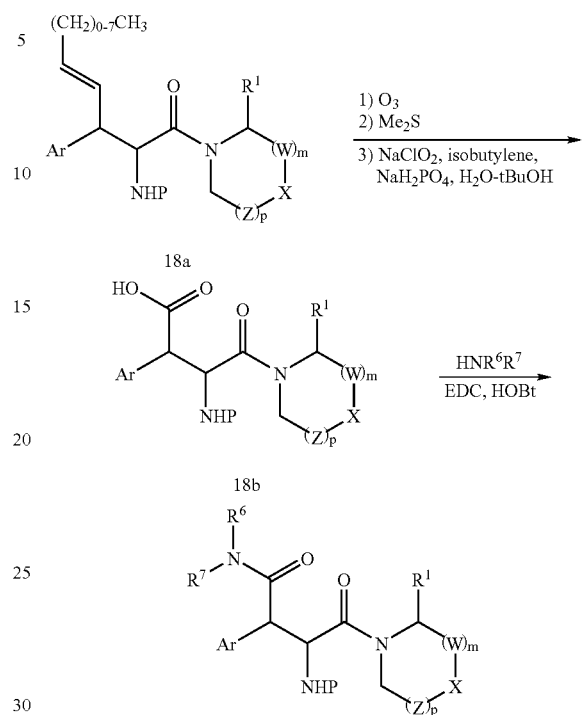

(Ar = appropriately substituted phenyl)

Scheme 9 illustrates an example in which the $R^2$ substituent undergoes further reaction. Ozonolysis of intermediate 18a followed by oxidation provides acid 18b. The acid may be coupled with an amine to give amide 18c. Intermediates 18b and 18c may be converted to product I as illustrated in Scheme 6.

In some cases the order of carrying out the foregoing reaction schemes may be varied to facilitate the reaction or to avoid unwanted reaction products. The following examples are provided so that the invention might be more fully understood. These examples are illustrative only and should not be construed as limiting the invention in any way.

INTERMEDIATE 1

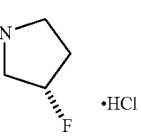

(3S)-3-Fluoropyrrolidine hydrochloride

Step A: Benzyl (3R)-3-hydroxypyrrolidine-1-carboxylate

A 22-L, 3-neck, round bottom flask equipped with mechanical stirrer, thermocouple, addition funnel and nitrogen bubbler was charged with 425 g (4.88 mol) of (3R)-3-hydroxypyrrolidine, 8 L of dichloromethane, and 1 L (7.17 mol) of triethylamine. The solution was cooled to 5–10° C.

with an ice bath and then 1000 g (5.86 mol) of benzyl chloroformate was added dropwise over a period of about 1.5 h keeping the reaction temperature <20° C. The reaction mixture was stirred for an additional hour in the ice bath, then the bath was removed and the reaction mixture was allowed to warm to ambient temperature overnight. The mixture was poured into a large extractor containing ~15 L of saturated aqueous sodium bicarbonate solution. The aqueous phase was back-extracted with two 2-L portions of dichloromethane. The combined organics were dried over magnesium sulfate and concentrated to give an orange oil. The crude material was taken up in dichloromethane, applied to a 5-kg column of silica gel prepacked in 50% ethyl acetate/hexane, and eluted sequentially with 8 L of 50%, 16 L of 75%, then 100% ethyl acetate/hexane to provide the title compound as a yellow oil which crystallized upon standing.

Step B: Benzyl (3S)-3-fluoropyrrolidine-1-carboxylate

A 5-L, 3-neck, round bottom flask equipped with mechanical stirrer, thermocouple, addition funnel and nitrogen bubbler was charged with 375 mL (2.84 mol) of (diethylamino)sulfur trifluoride and 400 mL of dichloromethane. The solution was cooled to −78° C. To this was added via addition funnel a solution of 304 g (1.37 mol) of benzyl(3R)-3-hydroxypyrrolidine-1-carboxylate in 400 mL of dichloromethane over a 2-h period keeping the reaction temperature <−70° C. The reaction mixture was allowed to stir and warm slowly to ambient temperature overnight. The reaction mixture was added portion-wise with caution to a large extractor containing ice, water, and saturated aqueous sodium bicarbonate solution. The mixture was extracted with 8 L of ethyl acetate. The organic layer was washed with saturated aqueous brine, dried over magnesium sulfate, and concentrated to give a brown oil. Purification by flash chromatography (silica gel, eluting with a 10 to 30% ethyl acetate/hexane gradient) gave the title compound as a brown oil.

Step C: (3S)-3-Fluoropyrrolidine hydrochloride salt

Benzyl (3S)-3-fluoropyrrolidine-1-carboxylate (249 g, 1.11 mmol) was dissolved in 2.3 L of ethanol and then 115 mL of water was added, followed by 30 g of 10% palladium on carbon. The mixture was shaken under 40 psi hydrogen for about 24 h. An additional 10 g and then 5 g of catalyst were added. The mixture was stirred under 40 psi hydrogen until complete. The mixture was filtered and the filter cake washed with ethanol. The combined filtrate and washings were treated with 185 mL of concentrated hydrochloric acid and concentrated to a colorless oil. The residue was azeotroped with toluene, then 2 L of diethyl ether was added. Isopropyl alcohol was added until the the oil crystallized. The mixture was allowed to age at ambient temperature over the weekend. The crystals were collected, washed with diethyl ether, and dried in vacuo to give the title compound. $[\alpha]_D$=+8.64 (c=4, methanol).

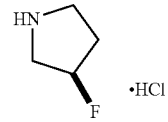

INTERMEDIATE 2

(3R)-3-Fluoropyrrolidine hydrochloride

Step A: Benzyl (3S)-3-acetoxypyrrolidine-1-carboxylate

A 22-L, 3 neck round bottom flask equipped with a mechanical stirrer, thermocouple, addition funnel and nitrogen bubbler was charged with 422 g (1.91 mol) of benzyl (3R)-3-hydroxypyrrolidine-1-carboxylate (Intermediate 1, Step A), 12 L of toluene, 751 g (2.86 mol) of triphenylphosphine, and 164 mL (2.86 mol) of glacial acetic acid. The resultant mixture was stirred at ambient temperature and then 500 g (2.87 mol) of diethyl azodicarboxylate was added via the addition funnel over a period of about 30 min, keeping the internal temperature <28° C. with a cold water bath. The reaction was stirred at ambient temperature overnight. The solvent was removed in vacuo and the residue was triturated with 6 L of diethyl ether. The solid was filtered off and washed well with diethyl ether. The filtrate and ether washings were combined and concentrated to a thick yellow oil with solids. Purification by flash chromatography (silica gel, eluting sequentially with 5% and a gradient of 10% to 30% ethyl acetate/hexane) gave the title compound as a pale yellow oil.

Step B: Benzyl (3S)-3-hydroxyppyrrolidine-1-carboxylate

To a 20-L, three neck round bottom flask containing 427 g (1.62 mol) of benzyl (3S)-3-acetoxypyrrolidine-1-carboxylate was added 4 L of absolute ethanol followed by 101 g (1.57 mol) of potassium hydroxide in about 400 mL of water. After about 15 min, the reaction mixture was poured into 8 L of water and extracted with 8 L of ethyl acetate. The aqueous layer was then extracted with an additional 4 L of ethyl acetate. The combined organics were washed with saturated aqueous brine, dried over magnesium sulfate and concentrated to a thick oil and solids.

Step C: Benzyl (3R)-3-fluoropyrrolidine-1-carboxylate

A 366 g (1.62 mol) portion of benzyl (3S)-3-hydroxypyrrolidine-1-carboxylate was converted to the title compound essentially following the procedure outlined in Intermediate 1, Step B.

Step D: (3R)-3-Fluoropyrrolidine hydrochloride salt

A 222 g (1.0 mol) portion of benzyl(3R)-3-fluoropyrrolidine-1-carboxylate was converted to the title compound essentially following the procedure outlined in Intermediate 1, Step C. $[\alpha]_D$=−8.61 (c=4, methanol).

INTERMEDIATE 3

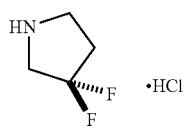

3,3-Difluoropyrrolidine hydrochloride

Step A: Benzyl 3-oxopyrrolidine-1-carboxylate

A 12-L, 3 neck round bottom flask equipped with a mechanical stirrer, thermocouple, condenser, and nitrogen bubbler was charged with 351 g (1.61 mol) of benzyl (3R)-3-hydroxypyrrolidine-1-carboxylate (Intermediate 1, Step A), 6 L of dichloromethane, 500 g of powdered molecular sieves, and 400 g (3.41 mol) of N-methylmorpholine-N-oxide. The resultant suspension was stirred at ambient temperature and to this was added 12.9 g (0.0367 mol) of tetrapropylammonium perruthenate. The reaction temperature was kept at ≦30° C. with a cold water bath. The mixture was stirred at ambient temperature for 2 h. The mixture was poured onto a plug of 5 kg of silica gel and eluted with 10% ethyl acetate/dichloromethane to give the title compound as an orange oil.

Step B: Benzyl 3,3-difluoropyrrolidine-1-carboxylate

A 12-L, 3 neck round bottom flask equipped with a mechanical stirrer, thermocouple, addition funnel and nitrogen bubbler was charged with 292 g (1.33 mol) of benzyl 3-oxopyrrolidine-1-carboxylate and 3 L of dichloromethane. To the stirring solution at ambient temperature was added dropwise 530 mL (4.0 mol) of (diethylamino)sulfur trifluoride over a period of about 3 h, keeping the internal temperature less than 25° C. using a cold water bath. The mixture was stirred at ambient temperature overnight. The mixture was poured into a large extractor containing ice and solid sodium bicarbonate. Eight liters of ethyl acetate were then added and the mixture was made basic with sodium bicarbonate. The organic layer was dried over magnesium sulfate and concentrated to 309 g of a brown oil. Purification by flash chromatography (silica gel, 10 to 20% ethyl acetate/hexane gradient) gave the title compound.

Step C: 3,3-Difluoropyrrolidine hydrochloride

A 242 g (1.00 mol) portion of benzyl 3,3-difluoropyrrolidine-1-carboxylate was converted to the title compound essentially following the procedure outlined in Intermediate 1, Step C. $^1$H NMR (500 MHz, CD$_3$OD): δ 3.7 (t, 2H), 3.6 (t, 2H), 2.55 (m, 2H).

INTERMEDIATE 4

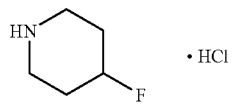

4-Fluoropiperidine hydrochloride

Step A: Benzyl 4-fluoro-1-piperidinecarboxylate

A 1-L, round bottom flask was charged with 12.64 g (51.4 mmol) of benzyl 4-oxo-1-piperidinecarboxylate and 300 mL of dichloromethane. To the stirring solution at −78° C. was added 19 mL (102.8 mmol) of [bis(2-methoxyethyl)amino]sulfur trifluoride via addition funnel over a period of about 1 h. The reaction mixture was allowed to warm slowly to ambient temperature overnight. The reaction mixture was added portionwise with caution to a large extractor containing water and saturated aqueous sodium bicarbonate solution. The mixture was extracted with dichloromethane (3×300 mL). The combined organic layers were washed once with saturated aqueous sodium bicarbonate solution, twice with 10% aqueous hydrochloric acid solution and saturated aqueous brine, dried over sodium sulfate, and concentrated in vacuo. Purification by flash chromatography on a Biotage® system (gradient, hexane to 65% ethyl acetate/hexane) afforded the desired product. LC/MS 242.1 (M+1).

Step B: 4-Fluoropiperidine hydrochloride

Benzyl 4-fluoro-1-piperidinecarboxylate (5.5 g, 23.2 mmol) was dissolved in 80 mL of ethanol and 1.0 g of 20% palladium hydroxide (dry basis) on carbon was added to the mixture. The mixture was shaken under 40 psi hydrogen for about 12 h then filtered through a celite pad and washed with 100 mL of methanol. The combined filtrate and washings were treated with 60 mL of 1 M hydrochloric acid in diethyl ether and concentrated to a white waxy solid. The solid was dried in vacuo to give the title compound as a solid. The material was used without further purification. $^1$H NMR (CDCl$_3$): δ 4.95 (d, J=47.4 Hz, 1H), 3.70 (br s, 1H), 3.34–3.27 (m, 4H), 2.29 (dt, J=37.1, 12.3 Hz, 2H), 2.16 (br s, 2H).

INTERMEDIATE 5

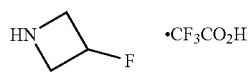

3-Fluoroazetidine trifluoroacetic acid salt

Step A: 1-Benzhydryl-3-fluoroazetidine

A 250 mL, round bottom flask was charged with 3.0 g (12.5 mmol) of 1-benzhydryl-3-fluoroazetidine and 80 mL of dichloromethane. To the stirring solution at −78° C. was added 4.6 mL (25 mmol) of [bis(2-methoxyethyl)amino]sulfur trifluoride via addition funnel over a period of about 3 h. The reaction mixture was allowed to warm slowly to ambient temperature overnight. The reaction mixture was added portionwise (with caution) to a large extractor containing water and saturated aqueous sodium bicarbonate solution. The mixture was extracted three times with 80 mL of dichloromethane. The combined organic layers were washed sequentially with saturated aqueous sodium bicarbonate solution, water and saturated aqueous brine, dried over sodium sulfate, and concentrated in vacuo. Purification by flash chromatography using a Biotage® system (gradient, hexane to 80% ethyl acetate/hexane) afforded the desired product. LC/MS 242.1 (M+1).

Step B: 3-Fluoroazetidine trifluoroacetic acid salt

1-Benzhydryl-3-fluoroazetidine (1.7 g, 7.04 mmol) was dissolved in 60 mL of ethanol and 500 mg of 20% palladium hydroxide (dry basis) on carbon. The mixture was shaken under 40 psi hydrogen for about 12 h. The mixture was filtered through a celite pad and the filter cake washed with 100 mL of methanol. The combined washings were treated with 10 mL of trifluoroacetic acid and concentrated to give two oils, the more dense of which is the desired fluoroazetidine salt. The mixture was not purified further. $^1$H NMR (CDCl$_3$) δ 5.45–4.30 (dm, J=56.7 Hz, 1H), 4.46–4.38 (m, 2H), 4.24–2.17 (m, 2H).

EXAMPLE 1

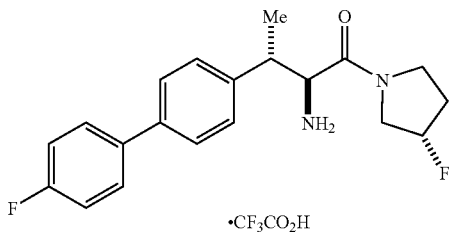

(3S)-1-[(2S,3S)-2-Amino-3-(4'-fluoro-1,1'-biphenyl-4-yl)-1-oxobutanyl]-3-fluoropyrrolidine, trifluoroacetic acid salt

Step A: (4R)-3-[(2E)-3-(4-Bromophenyl)prop-2-enoyl]-4-phenyl-1,3-oxazolidin-2-one To a stirred solution of 4-bromocinnamic acid (5.79 g, 22.5 mmol) in anhydrous THF (250 mL) was added triethylamine (4.60 mL, 34.6 mmol) followed by trimethylacetyl chloride (3.54 mL, 24.7 mmol) at −78° C. The resultant suspension was stirred at −78° C. for 15 min, 0° C. for 1 h, at then −78° C. for 15 min before being transferred via cannula into a slurry of lithium 4(R)-4-phenyl-2-oxazolidinone at 0° C., which was prepared 15 min in advance at −78° C. by addition of n-butyllithium (19.1 mL, 30.5 mmol) to a solution of 4(R)-4-phenyl-2-oxazolidinone (5.0 g, 30.6 mmol) in anhydrous THF (150 mL) at −78° C. The resultant slurry was stirred at −78° C. for 1 h and room temperature for 12 h. The reaction was quenched with saturated aqueous ammonium chloride solution. The organic phase was separated, concentrated in vacuo, and the crude product was used directly for the next step. LC/MS 372.0 (M+1).

Step B: (4R)-3-[(3R)-3-(4-Bromophenyl)butanoyl]-4-phenyl-1,3-oxazolidin-2-one To a stirred solution of copper(II) bromide dimethylsulfide complex (8.78 g, 42.7 mmol) in THF (60 mL) and dimethylsulfide (30 mL) was added methylmagnesium bromide (12.7 mL, 3.0M in diethyl ether, 38.1 mmol) at −40° C. The resultant mixture was stirred at −40° C. for 30 min, then warmed to −20° C. The product from Step A (3.53 g, 9.48 mmol) in THF (30 mL) was added to the above reaction mixture over 1 h at −20° C. The resultant mixture was stirred at −20° C. for 2 h, then slowly warmed to room temperature and stirred at room temperature for 12 h. The reaction was quenched by slow addition of saturated aqueous ammonium chloride solution. The organic phase was separated and the aqueous phase was extracted with two portions of ethyl acetate. The combined organic layers were washed with saturated aqueous brine and concentrated in vacuo. Purification by flash chromatography (silica gel, 83:17 hexanes/ethyl acetate) afforded the desired product.

Step C: (4R)-3-[(2R,3S)-2-Bromo-3-(4-bromophenyl)butanoyl]-4-phenyl-1,3-oxazolidin-2-one To a stirred solution of the product from Step B (2.87 g, 7.39 mmol) in dichloromethane (40 mL) was added diisopropylethylamine (1.93 mL, 11.1 mmol) and dibutylborontriflate (9.6 mL, 1M solution in dichloromethane, 9.60 mmol) at −78° C. The light yellow solution was stirred at −78° C. for 15 min, 0° C. for 1 h and recooled to −78° C. for 15 min. The above solution was transferred to a precooled suspension of N-bromosuccinimide (3.93 g, 22.2 mmol) in dichloromethane (40 mL) via cannula. The resultant mixture was stirred at −78° C. for 1 h and 0° C. for 3 h. The reaction was quenched by addition of 0.5N aqueous sodium bisulfite solution. The organic phase was separated and the aqueous phase was extracted with two portions of ethyl acetate. The combined organic layers were washed with saturated aqueous brine and concentrated in vacuo. Purification by flash chromatography (silica gel, 83:17 hexanes/ethyl acetate) afforded the desired product.

Step D: (4R)-3-[(2S,3S)-2-Azido-3-(4-bromophenyl)butanoyl]-4-phenyl-1,3-oxazolidin-2-one To a stirred solution of the product from Step C (2.71 g, 6.39 mmol) in acetonitrile (40 mL) was added tetramethylguanidinium azide (3.51 g, 22.2 mmol). The reaction was stirred at room temperature for 12 h. The solid was filtered off, and the filtrate was evaporated. The crude product was purified by flash chromatography (83:17 hexanes/ethyl acetate) to give the desired product.

Step E: (2S,3S)-2-Azido-3-(4-bromophenyl)butanoic acid

To a stirred solution of the product from Step D (2.77 g, 6.23 mmol) in THF (60 mL) was added water (20 mL). The solution was stirred at 0° C. for 15 min, and then 30% hydrogen peroxide (6.0 mL, 52.9 mmol) was added followed by slow addition of lithium hydroxide (0.50 g, 21.2 mmol). The resultant mixture was stirred at 0° C. for 4 h. The reaction was quenched by addition of saturated aqueous sodium sulfite solution and stirred at room temperature for 30 min. The aqueous phase was separated and washed with three portions of dichloromethane. The aqueous phase was then acidified to pH 1 with 3N hydrochloric acid and extracted with three portions of ethyl acetate. The ethyl acetate extracts were combined, dried over sodium sulfate, and evaporated in vacuo to give the product, which was used in the next step directly.

Step F: (3S)-1-[(2S,3S)-2-[(tert-Butoxycarbonyl)amino]-3-(4-bromophenyl)-1-oxobutanyl]-3-fluoropyrrolidine To 1.20 g (4.22 mmol) of acid dissolved in anhydrous DMF (10 mL) was added EDC (2.29 g, 11.9 mmol), HOBT (1.62 g, 11.9 mmol), (3S)-3-fluoropyrrolidine hydrochloride (1.50 g, 11.9 mmol) and N,N'-diisopropylethylamine (4.2 mL, 23.6 mmol). After stirring at room temperature for 12 h, the reaction was diluted with ethyl acetate. The organic phase was washed with saturated aqueous brine, 1N hydrochloride acid and 1N aqueous sodium hydroxide solution, dried over sodium sulfate, and evaporated in vacuo to yield a yellow colored foam. To this foam was added 40 mL of dioxane, 4 mL of water and triphenylphosphine (4.70 g, 17.9 mmol). The reaction was heated at 90° C. for 12 h before it was cooled to room temperature. The solvent was removed in vacuo, and the residue was dissolved in 20 mL of dioxane and 20 mL of saturated aqueous sodium bicarbonate solution. To the resultant mixture was added 7.8 g of di-tert-butyldicarbonate (35.8 mmol). The reaction was stirred at room temperature for 12 h. The reaction mixture was diluted with ethyl acetate and acidified to pH 1 with 1N hydrochloric acid. The layers were separated, and the aqueous layer was extracted with two portions of ethyl acetate. The organic extracts were combined, washed with saturated aqueous brine, dried over sodium sulfate, and concentrated in vacuo. Purification by flash chromatography (silica gel, 66:34 hexanes/ethyl acetate) afforded the desired product. LC/MS 429.1 (M+1).

Step G: (3S)-1-[(2S,3S)-2-[(tert-Butoxycarbonyl)amino]-3-(4'-fluoro-1,1'-biphenyl-4-yl)-1-oxobutanyl]-3-fluoropyrrolidine To a stirred solution of the product from Step F (51.0 mg, 0.12 mmol) in 2 mL of toluene and 2 mL of ethanol was added 4-fluorophenylboronic acid (49.0 mg, 0.29 mmol), 1,1'-bis(diphenylphosphino)ferrocene palladium(II) chloride (19.5 mg, 0.024 mmol), and aqueous sodium carbonate solution (0.30 mL, 2 M, 0.60 mmol). The reaction was heated at 90° C. for 12 h before it was cooled to room temperature. The reaction mixture was filtered through a pad of silica gel. The solvent was removed in vacuo and the residue was purified by preparative TLC (silica, 50% ethyl acetate/hexanes) to afford the desired coupled product.

Step H: (3S)-1-[(2S,3S)-2-Amino-3-(4'-fluoro-1,1'-biphenyl-4-yl)-1-oxobutanyl]-3-fluoropyrrolidine, trifluoroacetic acid salt To a stirred solution of 61.0 mg of the coupled product from Step G in dichloromethane (5 mL) was added trifluoroacetic acid (1 mL) at room temperature. After stirring at room temperature for 1 h, the solvent was removed in vacuo and the residue was purified by HPLC (YMC Pro-C18 column, gradient elution, 10–90% acetonitrile/water with 0.1% TFA) to give the title compound. LC/MS 345.0 (M+1).

EXAMPLE 2

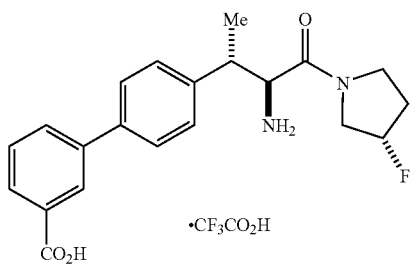

(3S)-1-[(2S,3S)-2-Amino-3-(3'-carboxy-1,1'-biphenyl-4-yl)-1-oxobutanyl]-3-fluoropyrrolidine, trifluoroacetic acid salt Step A: (3S)-1-[(2S,3S)-2-(tert-Butoxycarbonylamino)-3-(3'-benzyloxycarbonyl-1,1'-biphenyl-4-yl)-1-oxobutanyl]-3-fluoropyrrolidine To a stirred solution of the product from Example 1, Step F (214.9 mg, 0.50 mmol) in 5 mL of toluene and 5 mL of ethanol was added 3-benzyloxycarbonylphenyl boronic acid (512.4 mg, 2.00 mmol), 1,1'-bis(diphenylphosphino)ferrocene palladium(II) chloride (81.7 mg, 0.100 mmol), and 2M aqueous sodium carbonate solution (1.25 mL, 2.50 mmol). The reaction was heated at 90° C. for 12 h before it was cooled to room temperature. The reaction mixture was filtered through a pad of silica gel. The solvent was removed in vacuo and the residue was purified by preparative TLC (silica, 50% ethyl acetate/hexanes) to afford the desired coupled product.

Step B: (3S)-1-[(2S,3S)-2-(tert-Butoxycarbonylamino)-3-(3'-carboxy-1'-biphenyl-4-yl)-1-oxobutanyl]-3-fluoropyrrolidine To a stirred solution of the product from Step A in 3 mL of ethyl acetate was added 50 mg of 10% Pd—C. The reaction flask was flushed with nitrogen and then stirred under a hydrogen atmosphere (1 atm) for 12 h. Upon the completion of the reaction, the solution was passed through a pad of Celite. The solvent was removed in vacuo to give the title compound.

Step C: (3S)-1-[(2S,3S)-2-Amino-3-(3'-carboxy-1,1'-biphenyl-4-yl)-1-oxobutanyl]-3-fluoropmmolidine, trifluoroacetic acid salt The product from Step B was dissolved in 5 mL of dichloromethane and 1 mL of trifluoroacetic acid. The reaction was stirred at room temperature for 1 h. The solvent was removed in vacuo, and the residue was purified by HPLC (YMC Pro-C18 column, gradient elution, 10–90% acetonitrile/water with 0.1% TFA) to afford the title compound. LC/MS 371.1 (M+1).

EXAMPLE 3

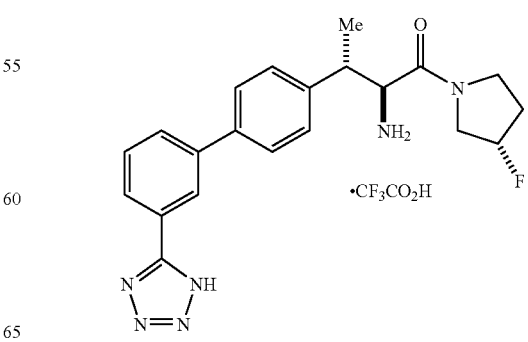

(3S)-1-[(2S,3S)-2-Amino-3-[3'-(tetrazol-5-yl)-1,1'-biphenyl-4-yl]-1-oxobutanyl]-3-fluoropyrrolidine, trifluoroacetic acid salt

Step A: (3S)-1-[(2S,3S)-2-(tert-Butoxycarbonylamino)-3-(3'-cyano-1,1'-biphenyl-4-yl)-1-oxobutanyl]-3-fluoroppyrrolidine To a stirred solution of the product from the Example 1, Step F (210.0 mg, 0.49 mmol) in 4 mL of toluene and 4 mL of ethanol was added 3-cyanophenyl boronic acid (275.6 mg, 1.87 mmol), 1,1'-bis(diphenylphosphino)ferrocene palladium(II) chloride (76.0 mg, 93.1 mmol), and 2M aqueous sodium carbonate solution (1.2 mL, 24.0 mmol). The reaction was heated at 90° C. for 12 h before it was cooled to room temperature. The reaction mixture was filtered through a pad of silica gel. The solvent was removed in vacuo and the residue was purified by preparative TLC (silica, 50% ethyl acetate/hexanes) to afford the desired coupled product.

Step B: (3S)-1-[(2S,3S)-2-[(tert-Butoxyl carbonyl)amino]-3-[3'-(tetrazol-5-yl)-1,1'-biphenyl-4-yl]-1-oxobutanyl]-3-fluoroppyrrolidine To a stirred solution of the product from Step A (101.0 mg, 0.22 mmol) in 5 mL of toluene was added trimethyltin azide (0.586 mg, 2.85 mmol). The reaction was heated at 100° C. for 12 h before it was cooled to room temperature. The solvent was removed, and the residue was purified by preparative TLC (silica, hexanes/ethyl acetate) to provide the desired product.

Step C: (3S)-1-[(2S,3S)-2-Amino-3-[3'-(tetrazol-5-yl)-1,1'-biphenyl-4-yl]-1-oxobutanyl]-3-fluoropyrrolidine, trifluoroacetic acid salt The product from Step B (56.2 mg) was dissolved in 5 mL of dichloromethane and 1 mL of trifluoroacetic acid and stirred at room temperature for 1 h. The solvent was removed in vacuo, and the residue was purified by HPLC (YMC Pro-C18 column, gradient elution, 10–90% acetonitrile/water with 0.1% TFA) to afford the title compound. LC/MS 395.2 (M+1).

EXAMPLE 4

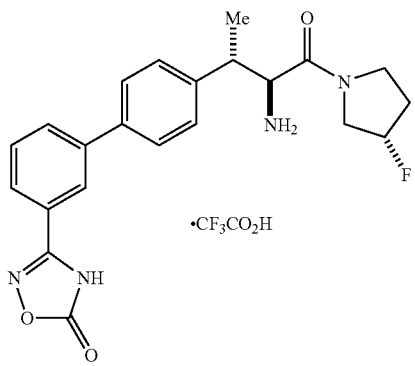

·CF$_3$CO$_2$H

(3S)-1-[(2S,3S)-2-Amino-3-[3'-(5-oxo-4,5-dihydro-1,2,4-oxadiazol-3-yl)-1,1'-biphenyl-4yl]-1-oxobutanyl]-3-fluoropyrrolidine, trifluoroacetic acid salt

Step A: (3S)-1-[(2S,3S)-2-(tert-Butoxycarbonylamino)-3-[3'-(5-oxo-4,5-dihydro-1,2,4-oxadiazol-3-yl)-1,1'-biphenyl-4-yl]-1-oxobutanyl]-3-fluoropyrrolidine To a stirred solution of the product from the Example 3, Step A (140 mg, 0.31 mmol) in 3 mL of ethanol was added 3 mL of hydroxylamine (50% in water). The reaction was heated at 90° C. for 12 h before it was cooled to room temperature. The solvent was removed in vacuo and and the residue azeotropically dried with toluene. To a stirred solution of the above residue in 5 mL of dichloromethane was added triethylamine (0.31 mL, 2.22 mmol) followed by ethyl chloroformate (0.155 mL, 1.48 mmol). The reaction was stirred at room temperature for 2 h before it was quenched by saturated aqueous ammonium chloride solution. The aqueous solution was extracted with ethyl acetate. The combined organic layers were washed with saturated aqueous brine, dried over sodium sulfate and concentrated in vacuo. The residue was dissolved in 5 mL of toluene and heated at 120° C. overnight. The solvent was removed in vacuo and the residue was purified by preparative TLC (silica, 25% ethyl acetate/hexanes) to afford the product. LC/MS 511.0 (M+1).

Step B: (3S)-1-[(2S,3S)-2-Amino-3-[3'-(5-oxo-4,5-dihydro-1,2,4-oxadiazol-3-yl)-1,1'-biphenyl-4-yl]-1-oxobutanyl]-3-fluoropyrrolidine, trifluoroacetic acid salt To a stirred solution of the product from Step A in 5 mL of dichloromethane was added 1 mL of trifluoroacetic acid. The reaction mixture was stirred at room temperature for 1 h. The solvent was removed in vacuo, and the residue was purified by HPLC (YMC Pro-C 18 column, gradient elution, 10–90% acetonitrile/water with 0.1% TFA) to afford the title compound. LC/MS 411.1 (M+1).

EXAMPLE 5

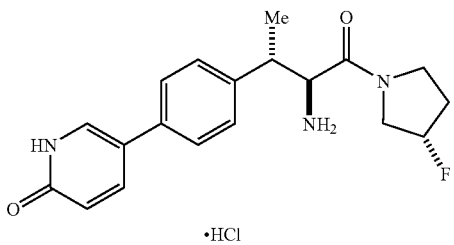

·HCl

(3S)-1-[(2S,3S)-2-Amino-3-[4-(6-oxo-1,6-dihydropyridin-3-yl)phenyl]-1-oxobutanyl]-3-fluoropyrrolidine, hydrochloride

Step A: (3S)-1-[(2S,3S)-2-(tert-Butoxycarbonylamino)-3-[4-(6-methoxypyridin-3-yl)phenyl]-1-oxobutanyl]-3-fluoropyrrolidine To a stirred solution of the product from Example 1, Step F (51.0 mg, 0.12 mmol) in 2 mL of toluene and 2 mL of ethanol was added 2-methoxy-5-pyridineboronic acid (71.3 mg, 0.466 mmol), 1,1'-bis(diphenylphosphino)ferrocene palladium(II) chloride (19.5 mg, 0.238 mmol), and 2M aqueous sodium carbonate solution (0.30 mL, 0.60 mmol). The reaction was heated at 90° C. for 12 h before it was cooled to room temperature. The reaction mixture was filtered through a pad of silica gel. The solvent was removed in vacuo and the residue was purified by preparative TLC (silica, 50% ethyl acetate/hexanes) to afford the desired coupled product.

Step B: (3S)-1-[(2S,3S)-2-Amino-3-[4-(6-oxo-1,6-dihydropyridin-3-yl)phenyl]-1- -oxobutanyl]-3-fluoropyrrolidine, hydrochloride The product from Step A was dissolved in 3 mL of concentrated hydrochloric acid (37%). The reaction mixture was heated at 100° C. for 48 h before it was cooled to room temperature. The water was removed azeotropically with toluene. Purification by HPLC (YMC Pro-C18 column, gradient elution, 10–90% acetonitrile/water with 0.1% concentrated hydrochloric acid) afforded the title compound. LC/MS 344.1 (M+1).

EXAMPLE 6

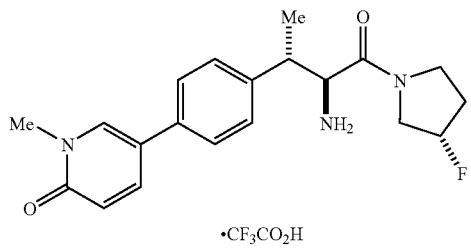

·CF₃CO₂H (3S)-1-[(2S,3S)-2-Amino-3-[4-(1-methyl-6-oxo-1,6-dihydropyridin-3-yl)phenyl]-1-oxobutanyl]-3-fluoropyrrolidine, trifluoroacetic acid salt Step A: (3S)-1-[(2S,3S)-2-(tert-Butoxycarbonylamino)-3-[4-(6-oxo-1,6-dihydropyridin-3-yl)phenyl]-1-oxobutanyl]-3-fluoropyrrolidine (3S)-1-[(2S,3S)-2-(tert-Butoxycarbonylamino)-3-[4-(6-methoxypyridin-3-yl)phenyl]-1-oxobutanyl]-3-fluoropyrrolidine from Example 5, Step A (0.65 g, 1.42 mmol) was mixed with pyridine hydrochloride (2.25 g, 19.5 mmol) neat and placed in a preheated oil bath (160° C.). After stirring at 160° C. for 20 min, the reaction was cooled to room temperature and neutralized to pH 7 with saturated sodium bicarbonate solution. To this was added 15 mL of 1,4-dioxane followed by di-tert-butyldicarbonate (2.14 g, 9.82 mmol). After stirring at room temperature for 12 h, the reaction was partitioned between ethyl acetate and saturated aqueous brine. The organic layer was separated, and the aqueous layer was extracted with two portions of ethyl acetate. The combined organic layers were dried over sodium sulfate and the solvents removed by evaporation under diminished pressure. Purification by preparative TLC (silica, 50% ethyl acetate/hexanes) afforded the desired product.

Step B: (3S)-1-[(2S,3S)-2-(tert-Butoxycarbonylamino)-3-[4-(1-methyl-6-oxo-1,6-dihydropyridin-3-yl)phenyl]-1-oxobutanyl]-3-fluoroppyrrolidine To a stirred solution of the product Step A (430.0 mg, 0.97 mmol) in 3 mL of DMF was added cesium carbonate (0.57 mmol, 1.74 mmol) followed by iodomethane (0.4 mL, 6.4 mmol) at room temperature. After 30 min the reaction mixture was diluted with ethyl acetate, washed with saturated aqueous brine, concentrated in vacuo and the residue was purified by preparative TLC (silica, 6% methanol in dichloromethane) to give the product.

Step C: (3S)-1-[(2S,3S)-2-Amino-3-[4-(1-methyl-6-oxo-1,6-dihydropyridin-3-yl)phenyl]-1-oxobutanyl]-3-fluoropyrrolidine, trifluoroacetic acid salt The product from Step B was dissolved in 5 mL of dichloromethane and 1 mL of trifluoroacetic acid. After 1 hour at room temperature, the solvent was remove in vacuo and the residue was purified by HPLC (YMC Pro-C18 column, gradient elution, 10–90% acetonitrile/water with 0.1% TFA) to provide the desired product. LC/MS 358.2 (M+1).

EXAMPLE 7

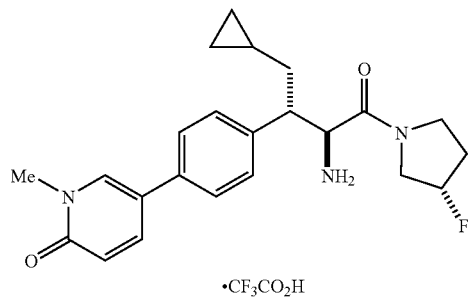

·CF₃CO₂H (3S)-1-[(2S,3S)-2-Amino-4-cyclopropyl-3-[4-(1-methyl-6-oxo-1,6-dihydropyridin-3-yl)phenyl]-1-oxobutanyl]-3-fluoroppyrrolidine, trifluoroacetic acid salt Step A: (4R)-3-[(3R)-3-(4-Bromophenyl)hex-5-enoyl]-4-phenyl-1,3-oxazolidin-2-one A 4.5 g portion of the product from Example 1, Step A was converted to the title compound essentially following the procedure outlined in Example 1, Step B using allylmagnesium bromide.

Step B: (4R)-3-[(3R)-3-(4-Bromophenyl)-4-cyclopropylbutanoyl]-4-phenyl-1,3-oxazolidin-2-one To a stirred solution of the product from Step A (1.32 g, 3.18 mmol) in 20 mL of diethyl ether was added excess of diazomethane solution in diethyl ether at 0° C. followed by palladium(II)acetate (0.215 g, 0.957 mmol) and the reaction was stirred at 0° C. for 2 h. The excess diazomethane was then quenched with acetic acid. The reaction mixture was filtered through a pad of silica gel and the solvent was removed in vacuo. NMR indicated a 1:1 mixture of the desired product and the starting material. The same reaction sequence was repeated one more time and the desired product was isolated by flash chromatography (silica gel, 25% ethyl acetate in hexanes). LC/MS 430.0 (M+1).

Step C: (4R)-3-[(2R,3S)-2-Bromo-3-(4-bromophenyl)-4-cyclopropylbutanoyl]-4-phenyl-1,3-oxazolidin-2-one A 1.16 g portion of the product from Step B was converted to the title compound essentially following the procedure outlined in Example 1, Step C.

Step D: (4R)-3-[(2S,3S)-2-Azido-3-(4-bromophenyl)-4-cyclopropylbutanoyl]-4-phenyl-1,3-oxazolidin-2-one A 0.61 g portion of the product from Step C was converted to the title compound essentially following the procedure outlined in Example 1, Step D.

Step E: (2S,3S)-2-Azido-3-(4-bromophenyl)4-cyclopropylbutanoic acid

A 0.51 g portion of the product from Step D was converted to the title compound essentially following the procedure outlined in Example 1, Step E.

Step F: (3S)-1-[(2S,3S)-2-Azido-3-(4-bromophenyl)-4-cyclopropylbutanoyl]-3-fluoropyrrolidine A 0.267 g portion of the product from Step E was converted to the title compound essentially following the procedure outlined in Example 1, Step F.

Step G: (3S)-1-[(2S,3S)-3-(4-Bromophenyl)-2-(tert-butoxycarbonylamino)-4-cyclopropylbutanoyl]-3-fluoropyrrolidine A 0.31 g portion of the product from Step F was converted to the title compound essentially following the procedure outlined in Example 1, Step G.

Step H: (3S)-1-[(2S,3S)-2-(tert-Butoxycarbonylamino)-4-cyclopropyl-3-[4-(6-methoxypyridin-3-yl)phenyl]butanoyl]-3-fluoropyrrolidine A 0.17 g portion of the product from Step G was converted to the title compound essentially following the procedure outlined in Example 5, Step A. LC/MS 498.1 (M+1).

Step I: (3S)-1-[(2S,3S)-2-(tert-Butoxycarbonylamino)-4-cyclopropyl-3-[4-(6-oxo-1,6-dihydropyridin-3-yl)phenyl]butanoyl]-3-fluoroppyrrolidine The product from Step H (0.18 g, 0.361 mmol) was mixed with pyridine hydrochloride (0.83 g, 7.21 mmol) neat and placed into a preheated oil bath (160° C.). After stirring at 160° C. for 20 min, the reaction was cooled to room temperature and neutralized to pH 7 with saturated aqueous sodium bicarbonate solution. Ten mL of 1,4-dioxane was then added followed by di-tert-butyldicarbonate (0.473 g, 2.17 mmol). After stirring at room temperature for 12 h, the reaction was partitioned between ethyl acetate and saturated aqueous brine. The organic layer was separated, and the aqueous layer was extracted with two portions of ethyl acetate. The combined organic layers were dried over sodium sulfate and the solvent removed by evaporation under diminished pressure. Purification by preparative TLC (silica, 50% ethyl acetate in hexanes) afforded the desired product.

Step J: (3S)-1-[(2S,3S)-2-Amino-4-cyclopropyl-3-[4-(1-methyl-6-oxo-1,6-dihydropyridin-3-yl)phenyl]-1-oxobutanyl]-3-fluoropmmolidine, trifluoroacetic acid salt A 0.056 g portion of the product from Step I was converted to the title compound essentially following the procedure outlined in Example 6, Steps B and C. LC/MS 398.3 (M+1).

EXAMPLE 8

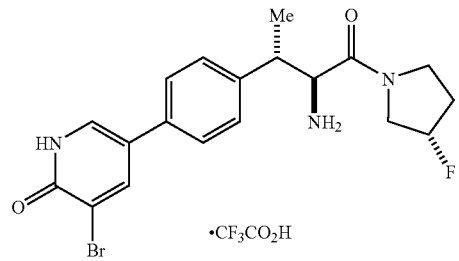

(3S)-1-[(2S,3S)-2-Amino-3-[4-(5-bromo-6-oxo-1,6-dihydropyridin-3-yl)phenyl]-1-oxobutanyl]-3-fluoropyrrolidine, trifluoroacetic acid salt To a stirred solution of (3S)-1-[(2S,3S)-2-(tert-butoxycarbonylamino)-3-[4-(6-oxo-1,6-dihydropyridin-3-yl)phenyl]-1-oxobutanyl]-3-fluoropyrrolidine (Example 6, Step A, 111.4 mg, 0.251 mmol) in 3 mL of dichloromethane was added pyridinium tribromide (0.098, 0.306 mmol). After 2 hour at room temperature, the solvent was removed in vacuo and the residue was purified by preparative TLC (silica, 9% methanol/dichloromethane) to give 47 mg of product, which was dissolved in 5 mL of dichloromethane and 1 mL of trifluoroacetic acid. After 1 hour at room temperature, the solvent was removed in vacuo and the residue was purified by HPLC (YMC Pro-C18 column, gradient elution, 10–90% acetonitrile/water with 0.1% TFA) to provide the title compound. LC/MS 424.0 (M+1).

EXAMPLE 9

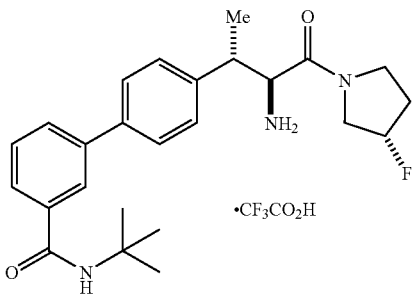

(3S)-1-[(2S,3S)-2-Amino-3-[3'-[(tert-butylamino) carbonyl]-1,1'-biphenyl-4-yl]-1-oxobutanyl]-3-fluoropyrrolidine, trifluoroacetic acid salt To a stirred solution of (3S)-1-[(2S,3S)-2-(tert-butoxycarbonylamino)-3-(3'-carboxy-1,1'-biphenyl-4-yl)-1-oxobutanyl]-3-fluoropyrrolidine (Example 2, Step B) (37.6 mg, 0.08 mmol) in anhydrous N,N-dimethylformamide (1.0 mL) was added 1-(3-dimethylaminopropyl)-3-ethylcarbodiimide hydrochloride (EDC, 23 mg, 0.12 mmol), hydroxybenzotriazole (HOBT, 16.2 mg, 0.12 mmol), and tert-butylamine (0.32 mL, 0.16 mmol). After stirring at room temperature for 16 hours, the reaction was diluted with ethyl acetate. The organic phase was washed sequentially with 0.5N hydrochloric acid, saturated aqueous sodium bicarbonate solution, water and saturated aqueous brine, dried (magnesium sulfate) and concentrated under reduced pressure to afford the crude coupled product, which was purified by preparative thin layer chromatography (silica gel, 50% ethyl acetate/ hexanes eluant). The resultant product was dissolved in 1 mL of dichloromethane and was treated with 1 mL of trifluoroacetic acid. The reaction was stirred at room temperature for one hour and was then concentrated under reduced pressure to afford the title compound. LC/MS 426.3 (M+1)

EXAMPLE 10

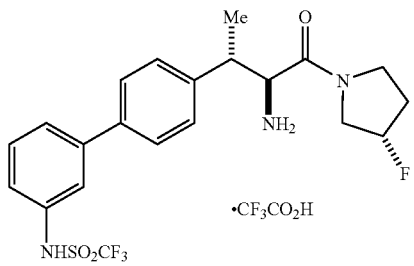

(3S)-1-[(2S,3S)-2-Amino-3-[3'-[[(trifluoromethyl) sulfonyl]amino]-1,1'-biphenyl-4-yl]-1-oxobutanyl]- 3-fluoropyrrolidine, trifluoroacetic acid salt Step A: 3-Iodo-phenyl-trifluoromethylsulfonamide To a solution of 3-iodoaniline (0.36 mL, 3.0 mmol) in 15 mL of dichloromethane was added trifluoroacetic anhydride (1.00 mL, 6.0 mmol) dropwise. Pyridine (1.21 mL, 15.0 mmol) was added, and the resultant clear solution was stirred at room temperature for 16 h. The reaction mixture was filtered, and the filtrate was concentrated under reduced pressure. The residue was dissolved in ethyl acetate (10 mL), then 1N aqueous sodium hydroxide solution (10 mL) was added. After stirring at room temperature for 30 min, the two layers were separated. The organic phase was washed with saturated aqueous brine, dried (magnesium sulfate) and concentrated. The crude product was purified by flash chromatography (silica gel, 30% ethyl acetate-hexanes eluant) to afford the desired product as a colorless oil.

Step B: (3S)-1-[(2S,3S)-2-[(tert-Butoxycarbonyl) amino]-3-[4-(4,4,5,5-tetramethyl-1,3,2-dioxaborolan-2-yl)phenyl]-1-oxobutanyl]-3-fluoropyrrolidine A thick-walled, resealable test-tube was charged with (3S)-1-[(2S,3S)-2-[(tert-butoxycarbonyl)amino]-3-(4-bromophenyl)-1-oxobutanyl]-3-fluoropyrrolidine (1.0 g, 2.33 mmol) from Example 1, step F, bis(pinacolato)diboron (1.78 g, 6.99 mmol), potassium acetate (1.14 g, 11.66 mmol) and 1,1'-bis(diphenylphosphino)ferrocene palladium(II) chloride (0.38 g, 0.466 mmol). Dimethyl sulfoxide (15 mL) was added, and the tube was then flushed with nitrogen and sealed. The reaction mixture was warmed at 80° C. overnight, cooled to room temperature and partitioned between water and ethyl acetate. The mixture was extracted with two additional portions of ethyl acetate. The combined ethyl acetate extracts were washed with saturated brine, dried (magnesium sulfate) and concentrated under reduced pressure to afford a brown oil. Purification by flash chromatography (silica gel, 5 to 25% ethyl acetate/hexane gradient elution) afforded the desired product as a foam. LC/MS 477.2 (M+1)

Step C: (3S)-1-[(2S,3S)-2-Amino-3-[3'-[[(trifluoromethyl)sulfonyl]amino]-1,1'-biphenyl-4-yl]-1- oxobutanyl]-3-fluoropyrrolidine, trifluoroacetic acid salt To a stirred solution of the product (70.2 mg, 0.2 mmol) from Step A in 0.75 mL of ethylene glycol dimethyl ether and 0.75 mL of water was added 47.6 mg (0.10 mmol) of the product from Step B, 1,1'-bis(diphenylphosphino)ferrocene palladium(II) chloride (16.4 mg, 0.02 mmol) and potassium phosphate (63.6 mg, 0.3 mmol). The reaction mixture was heated at 90° C. for 16 h. After cooling to room temperature, the mixture was diluted with ethyl acetate, washed sequentially with saturated aqueous sodium bicarbonate solution, water, and saturated aqueous brine, dried (magnesium sulfate) and concentrated under reduced pressure to yield the crude coupled product, which was purified by preparative thin layer chromatography (silica, ethyl acetate eluant). The resultant coupled product was further purified by HPLC (YMC Pro-C18 column, gradient elution, 10–90% acetonitrile/water with 0.1% TFA). The purified product was dissolved in 0.5 mL of dichloromethane and was treated with 0.5 mL of trifluoroacetic acid. After stirring at room temperature for one hour, the solvent was removed in vacuo and the residue was purified by preparative HPLC (YMC Pro-C18 column, gradient elution, 10 to 90% acetonitrile/water with 0.1% TFA) to afford the title compound. LC/MS 474.2 (M+1).

EXAMPLE 11

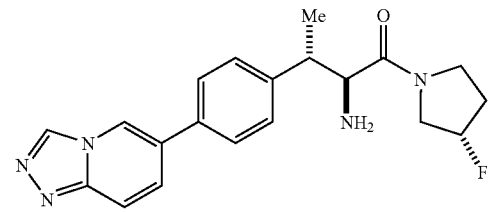

(3S)-1-[(2S,3S)-2-Amino-3-[4-([1,2,4]triazolo[4,3-α]pyridin-6-yl)phenyl]-1-oxobutanyl]-3-fluoropyrrolidine

Step A: 5-Iodo-2-hydrazinopyridine

A mixture of 2-chloro-5-iodopyridine (1.918 g, 8.01 mmol), anhydrous hydrazine (1.26 mL, 40.05 mmol) and pyridine (30 mL) was warmed at reflux for 18 h. After cooling to room temperature, the reaction mixture was concentrated under reduced pressure. The residue was partitioned between dichloromethane and 1N aqueous sodium hydroxide solution. The organic layer was separated, dried (magnesium sulfate) and concentrated under reduced pressure. The residue was triturated with hexanes, and the resultant precipitate was collected and dried in vacuo to afford the title compound as off-white crystals. LC/MS 235.8 (M+1).

Step B: 6-Iodo-[1,2,4]triazolo[4,3-α]pyridine

A mixture of the product (2.0 g, 8.51 mmol) from Step A above in triethyl orthoformate (100 mL) was warmed at reflux for 18 h. After cooling to room temperature, the reaction mixture was concentrated under reduced pressure. The residue was dissolved in 250 mL of dichloromethane and was filtered through a pad of silica gel. The pad was washed with 20% methanol/dichloromethane to elute the compound from the silica gel, and this filtrate was concentrated to dryness and then redissolved in dichloromethane. Addition of hexanes afforded a precipitate, which was collected. The filtrate was concentrated to half volume, and was then diluted with additional hexanes to yield a second crop of product. The combined solids were dried in vacuo to afford the title compound as a pale yellow solid. LC/MS 246.0 (M+1)

Step C: (3S)-1-[(2S,3S)-2-Amino-3-[4-([1,2,4]triazolo[4,3-α]pyridin-6-yl)phenyl]-1-oxobutanyl]-3-fluoropyrrolidine To a stirred solution of the product (48.0 mg, 0.195 mmol) from Step B in 0.75 mL of ethylene glycol dimethyl ether and 0.75 mL of water was added 62.0 mg (0.13 mmol) of (3S)-1-[(2S,3S)-2-[(tert-butoxycarbonyl)amino]-3-[4-(4,4,5,5-tetramethyl-1,3,2-dioxaborolan-2-yl)phenyl]-1-oxobutanyl]-3-fluoropyrrolidine from Example 10, Step B, 1,1'-bis(diphenylphosphino)ferrocene palladium(II) chloride (21.0 mg, 0.26 mmol) and potassium phosphate (83 mg, 0.39 mmol). The reaction mixture was heated at 90° C. for 16 h, and then allowed to cool to room temperature. The mixture was diluted with ethyl acetate, and the solution was washed sequentially with water and saturated aqueous brine, dried (magnesium sulfate), and concentrated under reduced pressure in vacuo to yield the crude coupled product, which was purified by preparative thin layer chromatography (silica gel, 5% methanol/dichloromethane eluant). The resultant product was dissolved in 1 mL of dichloromethane and was treated with 1 mL of trifluoroacetic acid. The reaction was stirred at room temperature for 1 h, and was then concentrated under reduced pressure. The residue was purified by preparative thin layer chromatography (silica gel, 10% methanol/1% ammonium hydroxide/dichloromethane eluant) to afford the title compound. LC/MS 368.2 (M+1).

EXAMPLE 12

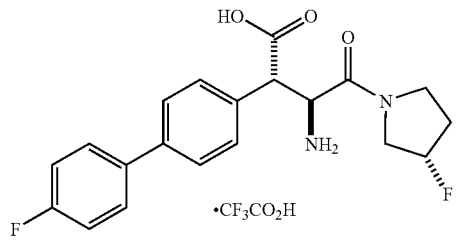

(3S)-1-[(2S,3S)-2-Amino-3-carboxy-3-(4'-fluoro-1,1'-biphenyl-4-yl)-1-oxopropanyl]-3-fluoropyrrolidine, trifluoroacetic acid salt

Step A: trans-4-(4-Bromophenyl)-3-buten-2-one

To 25.0 g (110 mmol) of 4-bromocinnamic acid dissolved in anhydrous dichloromethane (500 mL) was added EDC (28.8 g, 150 mmol), HOBT (20.3 g, 150 mmol), N,O-dimethylhydroxylamine hydrochloride (14.6 g, 150 mmol) and N,N'-diisopropylethylamine (23 mL, 150 mmol). After stirring at room temperature for 24 h, the reaction was concentrated then diluted with 400 mL of 10% aqueous hydrochloric acid. The resultant mixture was then extracted with three 300-mL portions of diethyl ether, the organic phases combined and washed sequentially with 10% hydrochloric acid, saturated aqueous sodium bicarbonate solution, and saturated aqueous brine (100 mL each). The organic phase was then dried over magnesium sulfate, filtered, and evaporated in vacuo to yield the Weinreb amide as a viscous oil that was used without further purification. To this oil was added 300 mL of anhydrous tetrahydrofuran and the resultant solution was cooled to −78° C. To this solution was added 60 mL of methylmagnesium bromide (180 mmol, 3N in diethyl ether). The stirred mixture was allowed to warm slowly to 0° C. over 1 h. The mixture was then quenched carefully with water and 5% aqueous hydrochloric acid (100 mL each) then concentrated to remove the tetrahydrofuran. The resultant mixture was extracted with three 300-mL portions of diethyl ether, the organic phases combined and washed sequentially with 5% hydrochloric acid, saturated aqueous sodium bicarbonate solution, and saturated aqueous brine (100 mL each). The organic phase was then dried over magnesium sulfate, filtered, and evaporated in vacuo to yield a viscous oil. The crude material was then purified by flash chromatography on a Biotage® system (silica gel, 0 to 15% ethyl acetate/hexanes gradient) to give the title compound as pale yellow crystalline solid. LC/MS 225.0 (M+1), 227.0 (M+3).

Step B: (2S,3E)-4-(4-Bromophenyl)-3-buten-2-ol

To 5.55 g (24.7 mmol) of the ketone from Step A dissolved in 100 mL of toluene was added 3.7 mL (3.7 mmol, 1M in toluene) of (R)-2-methyl-CBS-oxazaborolidine catalyst and the resultant mixture was stirred at ambient temperature for 15 min. The mixture was cooled to −78° C. and 4.0 mL (37.1 mmol) of catecholborane in 30 mL of toluene was added dropwise over 30 minutes. After the addition, the slurry was stirred at −78° C. for 60 min while slowly turning homogeneous. The solution was then stirred at −78° C. an additional 4 hours (reaction time varies from 4–24 hours) until TLC revealed complete disappearance of starting material. Next, the reaction mixture was diluted with 100 mL of water and the resultant mixture was extracted with three 100-mL portions of diethyl ether. The organic phases were then combined and washed with two 100-mL portions of 1 N NaOH aqueous solution, two 100 mL portions of 5% hydrochloric acid solution, 100-mL portions of saturated aqueous brine, dried over magnesium sulfate, filtered, and evaporated in vacuo to yield the crude waxy solid. The crude material was then purified by flash chromatography on a Biotage® system (silica gel, 0 to 20% ethyl acetate/hexanes gradient) to give the alcohol as a colorless crystalline solid. This compound was recrystallized in hexanes to yield the alcohol as colorless crystals (96% ee by Mosher ester analysis). LC/MS 209.0 (M–$H_2O$+1), 211.0 (M–$H_2O$+3).

Step C: (1S,2E)-3-(4-Bromophenyl)-1-methylprop-2-enyl N-(tert-butoxycarbonyl)glycinate To 12.6 g (55 mmol) of the alcohol from Step B dissolved in anhydrous dichloromethane (300 mL) was added EDC (23 g, 120 mmol), HOBT (16 g, 120 mmol), N-(tert-butoxycarbonyl)glycine (21 g, 120 mmol) and N,N'-diisopropylethylamine (19 mL, 120 mmol). After 5 h, the mixture was concentrated and diluted with 200 mL of 10% aqueous hydrochloric acid. The resultant mixture was then extracted with three 300-mL portions of diethyl ether, the organic phases combined and washed sequentially with 5% hydrochloric acid, saturated aqueous sodium bicarbonate solution, and saturated aqueous brine (100 mL each). The organic phase was then dried over magnesium sulfate, filtered, and evaporated in vacuo to yield the crude material as a viscous oil. The crude material was purified by flash chromatography on a Biotage® system (silica gel, 0 to 20% ethyl acetate/hexanes gradient) to give the title compound as a colorless crystalline solid. LC/MS 328.1 (M-tBu+1), 330.1 (M-tBu+3).

Step D: Methyl(βS)-4-Bromo-N-(tert-butoxycarbonyl)-β-[(1E)-prop-1-enyl]-L-phenylalaninate The ester from Step C (18.1 g, 47 mmol) in anhydrous tetrahydrofuran (50 mL) was added via cannula to 105 mL (105 mmol, 1M in tetrahydrofuran) of lithium hexamethyldisilazide solution precooled to –78° C. After stirring for 10 min at that temperature, 55 mL of zinc chloride solution (55 mmol, 1M in diethyl ether) was added at –78° C. The resultant mixture was stirred at –78° C. for 5 h then allowed to warm slowly to room temperature over 3 h. After stirring an additional 2 h at room temperature, the mixture was quenched with water and 5% hydrochloric acid (100 mL each). The resultant mixture was then extracted with three 300-mL portions of ethyl acetate, the organic phases combined and washed sequentially with 5% hydrochloric acid, saturated aqueous sodium bicarbonate solution, and saturated aqueous brine (200 mL each). The organic phase was then dried over magnesium sulfate, filtered, and evaporated in vacuo to yield the crude material as a yellow foam. LC/MS 384.1 (M+1), 386.1 (M+3). This crude material was dissolved in 500 mL of 1:1 diethyl ether/methanol and cooled to 0° C. Trimethylsilyldiazomethane solution (75 mL, 150 mmol, 2M in hexanes) was added in portions until a yellow color persisted. After warming to room temperature, the solution was stirred an additional 8 h, then concentrated in vacuo. The crude material was purified by flash chromatography on a Biotage® system (silica gel, 0 to 15% ethyl acetate/hexanes gradient) to give the title compound as a colorless oil. LC/MS 298.0 (M–Boc+1), 300.0 (M–Boc+3).

Step E: Methyl(2S,3S,4E)-2-[(tert-butoxycarbonyl)amino]-3-(4'-fluoro-1,1'-biphenyl-4-yl)-4-hexenoate To a stirred solution of the product from Step D (5.5 g, 13.8 mmol) in 40 mL of toluene and 7 mL of 2M aqueous sodium carbonate solution (14 mmol) was added 4-fluorophenylboronic acid (2.52 g, 18 mmol) and tetrakis(triphenylphosphine)palladium(0) (2 g, 1.7 mmol). The reaction was heated at 140° C. for 20 h before it was cooled to room temperature and diluted with 100 mL of water. The resultant mixture was then extracted with three 150-mL portions of diethyl ether, the organic phases combined and washed sequentially with 5% hydrochloric acid, saturated aqueous sodium bicarbonate solution, and saturated aqueous brine (100 mL each). The organic phase was then dried over magnesium sulfate, filtered, and evaporated in vacuo to yield the crude material as a viscous oil. The crude material was purified by flash chromatography on a Biotage® system (silica gel, 0 to 15% ethyl acetate/hexanes gradient) to give the title compound as a colorless waxy solid. LC/MS 414.3 (M+1).

Step F: (2S,3S,4E)-2-[(tert-Butoxycarbonyl)amino]-3-(4'-fluoro-1,1'-biphenyl-4-yl)-4-hexenoic acid A solution of the product from Step E (3.55 g, 8.9 mmol) in 250 mL of 3:1:1 tetrahydrofuran/methanol/1N aqueous lithium hydroxide solution (50 mL, 50 mmol) was stirred at room temperature for 15 h then concentrated and acidified with 200 mL of 10% aqueous hydrochloric acid. The resultant mixture was then extracted with three 150-mL portions of ethyl acetate, the organic phases combined and washed sequentially with 5% hydrochloric acid and saturated aqueous brine (100 mL each). The organic phase was dried over magnesium sulfate, filtered, and evaporated in vacuo to yield the acid as a colorless foamy solid that was used without further purification. LC/MS 385.2 (M+1).

Step G: (3S)-1-[(2S,3S)-2-[(tert-Butoxycarbonyl)amino]-3-(4'-fluoro-1,1'-biphenyl-4-yl)-1-oxohex-4-enyl]-3-fluoropyrrolidine To 2.11 g (5.49 mmol) of the acid from Step F dissolved in anhydrous dichloromethane (100 mL) was added EDC (1.34 g, 7.0 mmol), HOBT (0.95 g, 7.0 mmol), (3S)-3-fluoropyrrolidine hydrochloride (880 mg, 7.0 mmol) and N,N'-diisopropylethylamine (1.1 mL, 7.0 mmol). After stirring for 48 h at room temperature, the reaction mixture was concentrated and diluted with 100 mL of 10% aqueous hydrochloric acid. The resultant mixture was then extracted with three 150-mL portions of ethyl acetate, the organic phases combined and washed sequentially with 5% hydrochloric acid, saturated aqueous sodium bicarbonate solution, and saturated aqueous brine (100 mL each). The organic phase was then dried over magnesium sulfate, filtered, and evaporated in vacuo to yield the crude material as a viscous oil. The crude material was purified by flash chromatography on a Biotage® system (silica gel, 0 to 40% ethyl acetate/hexanes gradient) to give the title compound as a colorless solid. LC/MS 471.3 (M+1).

Step H: (3S)-1-[(2S,3S)-2-[(tert-Butoxycarbonyl) amino]-3-carboxy-3-(4'-fluoro-1,1'-biphenyl-4-yl)-1-oxopropanyl]-3-fluoropyrrolidine A solution of 1.0 g (2.12 mmol) of the olefin from Step G dissolved in 1:1 methanol/dichloromethane (150 mL) was purged with oxygen for 2 min then cooled to −78° C. Ozone was bubbled through the solution until a pale blue color persisted (about 5 min) then oxygen was bubbled through until the blue color disappeared again. Dimethyl sulfide (2 mL, excess) was added, and the resultant mixture was allowed to warm to room temperature and stirred an additional 20 min. The reaction mixture was concentrated and diluted with 200 mL of ethyl acetate then washed sequentially with 5% hydrochloric acid, saturated aqueous sodium bicarbonate solution, and saturated aqueous brine (50 mL each). The organic phase was dried over magnesium sulfate, filtered, and evaporated in vacuo to yield the crude aldehyde. The crude aldehyde, sodium dihydrogen phosphate (439 mg, 3.18 mmol), sodium chlorite (580 mg, 6.4 mmol), and isobutylene (4.25 mL, 8.5 mmol, 2M in THF) were stirred at room temperature for 8 h in 50 mL of 4:1 tert-butanol/water then concentrated. The crude mixture was diluted with 50 mL of 5% aqueous hydrochloric acid and extracted with three 150-mL portions of ethyl acetate. The organic phases were combined and washed sequentially with 5% hydrochloric acid and saturated aqueous brine (50 mL each), dried over magnesium sulfate, filtered, and evaporated in vacuo to yield the crude material as a colorless crystalline solid. The crude material was purified by HPLC (YMC Pro-C18 column, gradient elution, 30 to 95% acetonitrile/water with 0.1% TFA) to afford the title compound as a colorless crystalline solid. LC/MS 475.2 (M+1).

Step I: (3S)-1-[(2S,3S)-2-Amino-3-carboxy-3-(4'-fluoro-1,1'-biphenyl-4-yl)-1-oxopropanyl]-3-fluoropyrrolidine, trifluoroacetic acid salt The acid from Step H (55 mg, 0.12 mmol) was dissolved into 20 mL of 1:1 trifluoroacetic acid/dichloromethane and stirred for 60 min then concentrated. The crude material was purified by reverse phase HPLC (YMC Pro-C18 column, gradient elution, 10 to 90% acetonitrile/water with 0.1% TFA) to afford the title compound as a colorless crystalline solid. LC/MS 375.2 (M+1).

EXAMPLE 13

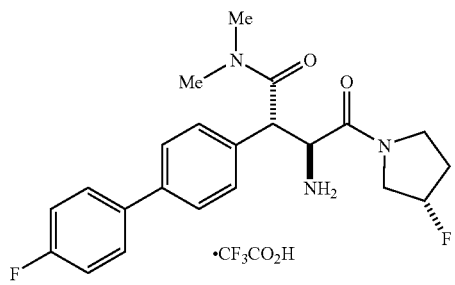

(3S)-1-[(2S,3S)-2-Amino-3-(dimethylaminocarbonyl)-3-(4'-fluoro-1,1'-biphenyl-4-yl)-1-oxopropanyl]-3-fluoropyrrolidine, trifluoroacetic acid salt To 200 mg (0.42 mmol) of (3S)-1-[(2S,3S)-2-[(tert-butoxycarbonyl)amino]-3-carboxy-3-(4'-fluoro-1,1'-biphenyl-4-yl)-1-oxopropanyl]-3-fluoropyrrolidine from Example 12, Step H dissolved in anhydrous dichloromethane (10 mL) was added EDC (116 mg, 0.6 mmol), HOBT (81 mg, 0.6 mmol), dimethylamine (0.4 mL, 0.8 mmol, 2.0 M in tetrahydrofuran) and N,N'-diisopropylethylamine (0.091 mL, 0.6 mmol). After stirring at room temperature for 48 h, the reaction was diluted with 200 mL of ethyl acetate then washed sequentially with 5% hydrochloric acid, saturated aqueous sodium bicarbonate solution, and saturated aqueous brine (50 mL each). The organic phase was dried over magnesium sulfate, filtered, and evaporated in vacuo to yield the amide as a yellow foam. This material was dissolved into 50 mL of 1:1 trifluoroacetic acid/dichloromethane and stirred for 60 min and then concentrated. The crude material was purified by HPLC (YMC Pro-C18 column, gradient elution, 10 to 90% acetonitrile/water with 0.1% TFA) to afford the title compound as a pale yellow crystalline solid. LC/MS 402.3 (M+1).

EXAMPLE 14

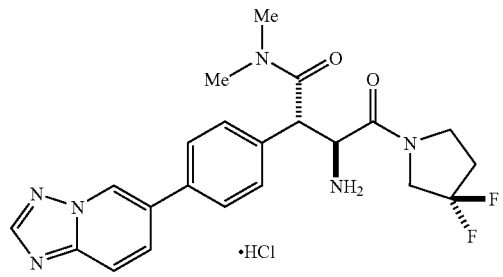

1-[(2S,3S)-2-Amino-3-(dimethylaminocarbonyl)-3-(4-[1,2,4]triazolo[1,5-α]pyridin-6-ylphenyl)-1-oxopropanyl]-3,3-difluoropyrrolidine, hydrochloride Step A: 1-[(2S,3S,4E)-3-(4-Bromophenyl)-2-(tert-butoxycarbonylamino)hex-4-enoyl]-3,3-difluoropyrrolidine To a solution of 25 g (62.8 mmol) of methyl(βS)-4-bromo-N-(tert-butoxycarbonyl)-β-[(1E)-prop-1-enyl]-L-phenylalaninate (Example 12, Step D) in 600 mL of tetrahydrofuran (THF) was added in succession 200 mL of methanol and 200 mL (200 mmol) of 1N aqueous sodium hydroxide solution. The reaction mixture was stirred at ambient temperature for 3 h, and then the methanol and THF were removed under reduced pressure. To the aqueous mixture was added 250 mL of 1N hydrochloric acid and the mixture was extracted with ethyl acetate (3×300 mL). The combined organic extracts were washed with brine (300 mL) then dried over sodium sulfate, filtered, and concentrated in vacuo to afford the carboxylic acid, which was used without further purification.

The above acid was mixed with 18.6 g (130 mmol) of 3,3-difluoropyrrolidine, 17.5 g (130 mmol) of HOBt, 22.8 mL (130 mmol) of N,N-diisopropylethylamine and 300 mL of DMF. 25 g (130 mmol) of EDC was then added, and the solution was stirred at ambient temperature under nitrogen for 12 h. Ethyl acetate (1.5 L) was added and the mixture was washed with 0.5N aqueous sodium bicarbonate solution (3×400 mL), 1N hydrochloric acid (2×400 mL) and brine (400 mL), dried over sodium sulfate, filtered and concentrated in vacuo to afford the title compound, which was sufficiently pure for use in the subsequent steps. MS 375.1 (M+1-Boc).

Step B: 1-[(2S,3S)-3-(4-Bromophenyl)-2-(tert-butoxycarbonylamino)-3-(dimethylaminocarbonyl)-1-oxopropanyl]-3,3-difluoropyrrolidine A round bottom flask was charged with 1.5 L of water, and 80 g (374 mmol) of sodium periodate was added. The mixture was stirred until homogeneous then 1.2 g (7.5 mmol) of potassium permanganate was added to the mixture. To this dark purple solution was added 5.7 g (41.1 mmol) of potassium carbonate powder (~325 mesh) and 17.7 g (37.4 mmol) of the product from Step A as a 500 mL tert-butanol solution. The reaction mixture was stirred at ambient temperature for 24 h, then treated with 50 mL of saturated aqueous sodium sulfite solution, acidified with 1N aqueous hydrochloric acid (400 mL), and then extracted with ethyl acetate (3×400 mL). The combined organic extracts were washed with brine (3×400 mL) and the resultant clear solution was dried over sodium sulfate, filtered and concentrated in vacuo to afford the crude acid which was used without further purification.

The above acid was mixed with 10.1 g (74.8 mmol) of HOBt and 300 mL of DMF. 13 mL (74.8 mmol) of N,N-diisopropylethylamine, 37.4 mL (74.8 mmol) of 2N dimethylamine in THF and 14.3 g (74.8 mmol) of EDC were then added sequentially to the solution. The reaction mixture was then stirred at ambient temperature for 12 h. Ethyl acetate (1.2 L) was then added and the mixture was washed with 0.5N aqueous sodium bicarbonate solution (3×400 mL), 1N aqueous hydrochloric acid (2×300 mL), and brine (400 mL), dried over sodium sulfate, filtered and concentrated in vacuo. Purification by flash chromatography using a Biotage Horizon® system (silica gel, 1:1 ethyl acetate/hexanes to 100% ethyl acetate to 10% methanol/ethyl acetate gradient) afforded the title compound. MS 450.0 (M+1-tert-butyl)

Step C: 1-[(2S,3S)-2-(tert-Butoxycarbonylamino)-3-(dimethylaminocarbonyl)-1-oxo-3-[4-(4,4,5,5-tetramethyl-1,3,2-dioxaborolan-2-yl)phenyl]propanyl]-3,3-difluoropyrrolidine To 11.5 g (22.8 mmol) of the bromide from Step B was added 11.5 (45.6 mmol) of bis(pinacolato)diboron, 3.7 g (4.6 mmol) of [1,1'-bis(diphenylphosphino)ferrocene]dichloropalladium(II) (complex with dichloromethane (1:1)), 11.2 g (114 mmol) of potassium acetate, and 70 mL of dimethyl sulfoxide (DMSO). Nitrogen was then bubbled through the mixture for 3 min, then the mixture was stirred at 80° C. under nitrogen for 4 h. The mixture was cooled to ambient temperature, then filtered through a silica gel pad and rinsed with excess ethyl acetate. The solution was washed with two portions of brine, dried over sodium sulfate, filtered and concentrated in vacuo. Purification by flash chromatography on a Biotage Horizon® system (silica gel, 40% ethyl acetate/hexanes to 100% ethyl acetate to 20% methanol/ethyl acetate gradient) afforded the title compound. MS 496.3 (M+1-tert-butyl).

Step D: 1-[(2S,3S)-2-Amino-3-(dimethylaminocarbonyl)-3-(4-[1,2,4]triazolo[1,5-α]pyridin-6-ylphenyl)-1-oxopropanyl]-3,3-difluoropyrrolidine, hydrochloride To 9.27 g (16.8 mmol) of the compound from Step C in 200 mL of ethanol/toluene (1:1) was added 6.7 g (33.6 mmol) of 6-bromo[1,2,4]triazolo[1,5-α]pyridine (Intermediate 18), 2.9 g (3.6 mmol) of [1,1'-bis(diphenylphosphino)ferrocene]dichloropalladium(II) (complex with dichloromethane, 1:1), and 42 mL (84 mmol) of 2N aqueous sodium carbonate solution. The reaction mixture was stirred at 90° C. under nitrogen for 12 h. After cooling to ambient temperature, 600 mL of ethyl acetate was added to the mixture and the organic phase was washed sequentially with 0.5N aqueous sodium bicarbonate solution and brine, dried over sodium sulfate, filtered and concentrated in vacuo. The crude material was purified by reverse phase HPLC on a Kiloprep® 100 G system (Kromasil $C_8$ 16 micron, isocratic elution, 40% acetonitrile/water with 0.1% TFA) to afford the coupled product.

The above intermediate was then dissolved in a 1:1 mixture of dichloromethane and TFA, stirred for 30 min at room temperature, then concentrated in vacuo. The product was purified by reverse phase HPLC on a Kiloprep® 100 G system (Kromasil $C_8$ 16 micron, gradient elution, 0% to 65% acetonitrile/water with 0.1% TFA) to afford the product as a TFA salt. This salt was then dissolved in water, and the aqueous solution adjusted to pH 2 via addition of 2N aqueous sodium carbonate solution. After extracting the aqueous mixture with 3:1 chloroform:isopropanol (5×300 mL), the combined organic layers were washed once with brine, then dried over sodium sulfate, filtered and concentrated in vacuo. The resultant amine was then dissolved in dichloromethane and 30 mL of 2N hydrogen chloride in ether was added to the solution. After stirring for 60 min, the solution was evaporated to afford the title compound as a white hydrochloride salt. The compound was further purified by recrystallization (ethanol/ether) then lyophilization from water/acetonitrile (40:60, 100 mL) to afford the title compound. MS 443.2 (M+1). 500 MHz $^1$H NMR (CD$_3$OD) δ 9.12 (s, 1H), 8.48 (s, 1H), 8.06 (dd, J=9.4, 1.6 Hz, 1H), 7.87 (d, J=9.3 Hz, 1H), 7.85 (d, J=8.0 Hz, 2H), 7.58 (dd, J=8.2, 1.6 Hz, 2 H), 4.69 (dd, J=57.4, 8.4 Hz, 1H), 4.58 (dd, J=13.8, 8.2 Hz, 1H), 4.52–3.74 (m, 6H), 2.96 (s, 3 H), 2.94 (d, J=1.1 Hz, 3H), 2.69–45 (m, 2H).

EXAMPLE 15

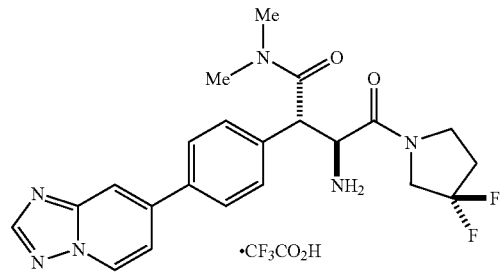

1-[(2S,3S)-2-Amino-3-(dimethylaminocarbonyl)-3-(4-[1,2,4]triazolo[1,5-α]pyridin-7-ylphenyl)-1-oxo-propanyl]-3,3-difluoropyrrolidine, trifluoroacetic acid salt A mixture of the intermediate from Example 14, Step C (48 mg, 0.090 mmol), Intermediate 19 (48 mg, 0.18 mmol) and tetrakis(triphenylphosphine)palladium(0) (12 mg) in 1.2 mL of dimethoxyethane, 0.30 mL of ethanol and 0.30 mL of 2M aqueous sodium carbonate solution was warmed at 84° C. under a nitrogen atmosphere for 18 h. The mixture was cooled to room temperature, diluted with 12 mL of ethyl acetate, and filtered through a plug of Celite. The filtrate was concentrated under reduced pressure, and the residue was purified by preparative thin layer chromatography (1 mm silica; 12:1 dichloromethane:10% ammonium hydroxide in methanol eluant) to afford 39 mg of protected intermediate, which was dissolved in 4 mL of dichloromethane and treated with 2 mL of trifluoroacetic acid. After one hour at room temperature, the volatiles were removed under a stream of nitrogen, and the residue was triturated with dry ether to afford the title compound as a white powder. MS 443.2 (M+1). 500 MHz $^1$H NMR (CD$_3$OD) δ 8.89 (d, J=7.1 Hz, 1H), 8.49 (s, 1H), 8.05 (s, 1H), 7.93 (d, J=8.2 Hz, 2H), 7.40 (m, 3H), 4.20–4.80 (m, 3H), 3.75–4.05 (m, 3H), 2.98 (s, 3H), 2.95 (s, 3H) 2.55 (m, 2H).

EXAMPLE 16

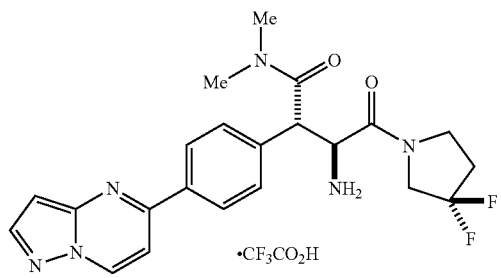

1-[(2S,3S)-2-Amino-3-(dimethylaminocarbonyl)-3-(4-pyrazolo[1,5-α]pyrimidin-5-ylphenyl)-1-oxopropanyl]-3,3-difluoroppyrrolidine, trifluoroacetic acid salt Reaction of the intermediate from Example 14, Step C (48 mg, 0.090 mmol) with Intermediate 20 (38 mg, 0.25 mmol) and tetrakis(triphenylphosphine)palladium(0) was carried out as described for the preparation of Example 15. The intermediate was purified by preparative thin layer chromatography (1 mm silica; 6% methanol in dichloromethane eluant), and deprotection with trifluoroacetic acid was performed as described in Example 15 to afford the title compound as a white solid. MS 443.2 (M+1).

EXAMPLE 17

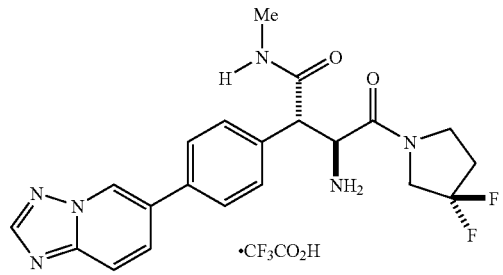

1-[(2S,3S)-2-Amino-3-(methylaminocarbonyl)-3-(4-[1,2,4]triazolo[1,5-α]pyridin-6-ylphenyl)-1-oxopropanyl]-3,3-difluoropyrrolidine, trifluoroacetic acid salt Step A: 1-[(2S,3R and 3S)-2-(tert-Butoxycarbonylamino)-3-carboxy-1-oxo-3-[4-(4,4,5,5-tetramethyl-1,3,2-dioxaborolan-2-yl)phenyl]propanyl]-3,3-difluoropyrrolidine A round bottom flask was charged with 1.5 L of water, and 80 g (374 mmol) of sodium periodate was added. The mixture was stirred until homogeneous, then 1.2 g (7.5 mmol) of potassium permanganate was added to the mixture. To this dark purple solution was added 5.7 g (41.1 mmol) of potassium carbonate powder (~325 mesh) and 17.7 g (37.4 mmol) of 1-[(2S,3S,4E)-3-(4-bromophenyl)-2-(tert-butoxycarbonylamino)hex-4-enoyl]-3,3-difluoropyrrolidine from Example 14, Step A as a 500 mL tert-butanol solution. The reaction mixture was stirred at ambient temperature for 24 h, then treated with 50 mL of saturated aqueous sodium sulfite solution, acidified with 1N aqueous hydrochloric acid (400 mL), and then extracted with ethyl acetate (3×400 mL). The combined organic extracts were washed with brine (3×400 mL) and the resultant clear solution was dried over sodium sulfate, filtered and concentrated in vacuo to afford the crude acid which was used without further purification.

A 6.0 g (12.6 mmol) portion of the above acid was mixed with 4.6 g (18.0 mmol) of bis(pinacolato)diboron, 400 mg (0.49 mmol) of [1,1'-bis(diphenylphosphino)ferrocene] dichloropalladium(II) (complex with dichloromethane (1:1)), 7.5 g (76 mmol) of potassium acetate, and 40 mL of dimethyl sulfoxide (DMSO). After purging with nitrogen, the mixture was stirred at 100° C. under nitrogen for 10 h. The mixture was cooled to ambient temperature, acidified with 1N aqueous hydrochloric acid (100 mL) then filtered through a Celite pad which was subsequently rinsed with ethyl acetate (200 mL). The layers were separated and the organic layer was extracted with ethyl acetate (2×200 mL). The organic layers were then combined and washed with two portions of brine, dried over magnesium sulfate, filtered and concentrated in vacuo. The resultant dark brown solid was sufficiently pure for use in the subsequent step. MS 425.4 (M+1-Boc).-

Step B: 1-[(2S,3R and 3S)-2-(tert-Butoxycarbony-lamino)-3-carboxy-3-(4-[1,2,4]triazolo[1,5-α]pyridin-6-ylphenyl)-1-oxopropanyl]-3,3-difluoropyrrolidine To the boronate from Step A in 80 mL of ethanol/toluene (1:1) was added 6.0 g (11.4 mmol) of 6-bromo[1,2,4]triazolo[1,5-α]pyridine (Intermediate 18), 400 mg (0.49 mmol) of [1,1'-bis(diphenylphosphino) ferrocene]dichloropalladium (II) (complex with dichloromethane, 1:1), and 37 mL (74 mmol) of 2N aqueous sodium carbonate solution. The reaction mixture was stirred at 100° C. under nitrogen for 18 h. After cooling to ambient temperature, 600 mL of ethyl acetate was added to the mixture and the organic phase was washed sequentially with 1N hydrochloric acid and brine, dried over magnesium sulfate, filtered and concentrated in vacuo. The crude material was purified by reverse phase HPLC (YMC Pro-C18 column, gradient elution, 10 to 90% acetonitrile/water with 0.1% TFA) to afford the pure coupled product as a mixture of diastereomers at the benzylic position. MS 516.4 (M+1).

Step C: 1-[(2S,3S)-2-Amino-3-(methylaminocarbonyl)-3-(4-[1,2,4]triazolo[1,5-α]pyridin-6-ylphenyl)-1-oxopropanyl]-3,3-difluoroppyrrolidine, trifluoroacetic acid salt To 150 mg (0.30 mmol) of acid from step B and 92 mg (0.80 mmol) of N-hydroxysuccinimide in 20 mL of dichloromethane was added 160 mg (0.80 mmol) of EDC, and the resultant solution was stirred at ambient temperature under nitrogen for 12 h. The reaction mixture was quenched with water then extracted with a solution of 3:1 chloroform/isopropyl alcohol (IPA). The combined organic layers were washed with saturated aqueous sodium bicarbonate solution (50 mL) and brine (50 mL), dried over magnesium sulfate, filtered and concentrated in vacuo to afford the N-hydroxysuccinimide ester. This crude material was dissolved into 10 mL of dioxane and 10 mL of methylamine (2N solution in THF, 20 mmol) and the mixture was stirred for 3 h at ambient temperature. The mixture was then concentrated and the residue was purified by reverse phase HPLC (YMC Pro-C18 column, gradient elution, 10 to 90% acetonitrile/water with 0.1% TFA) to afford the pure methyl amide as a mixture of diastereomers. MS 529.5 (M+1).

The above product was then dissolved in a 1:1 mixture of dichloromethane and TFA, stirred for 60 min at room temperature, then concentrated in vacuo. This material was then dissolved into 150 mL of 3:1 chloroform/IPA and washed with 50 mL of saturated aqueous sodium bicarbonate solution to form the free base. The organic layer was dried over magnesium sulfate, filtered, and concentrated in vacuo. The resultant diastereomeric mixture was separated by preparative TLC (10% methanol/dichloromethane) to afford the free base of the title compound as the less polar, faster eluting diastereomer. The free base was once again exposed to reverse phase HPLC (YMC Pro-C 18 column, gradient elution, 0% to 50% acetonitrile/water with 0.1% TFA) to afford the title compound. MS 429.4 (M+1). The following intermediates were used to prepare some of the compounds of the present invention listed in Tables 1–3.

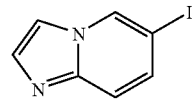

INTERMEDIATE 6

6-Iodoimidazo[1,2-α]pyridine

Step A: 2-Amino-5-iodopyridine

A mixture of 2-aminopyridine (941 mg, 10 mmol), iodine (980 mg, 3.86 mmol), and periodic acid (547 mg, 2.4 mmol) in 6.6 mL of acetic acid, 2.5 mL of water and 0.16 mL of concentrated sulfuric acid was heated at 80° C. for 2 h. The reaction was allowed to cool to room temperature and poured onto aqueous sodium thiosulfate solution. The aqueous solution was extracted several times with dichloromethane, and the combined extracts were dried (magnesium sulfate) and concentrated under reduced pressure to yield the crude product, which was purified by flash chromatography (silica gel, 25% ethyl acetate/hexanes) to afford the desired product. LC-MC 220.8 (M+1).

Step B: 6-Iodoimidazo[1,2-α]pyridine

To a solution of the product (480 mg, 2.18 mmol) from Step A in ethanol (12 mL) was added chloroacetaldehyde (50 wt. % in water, 0.336 mL) and the mixture was heated at 85° C. for 3 h. After cooling to room temperature, the solution was concentrated under reduced pressure. The residue was partitioned between saturated aqueous sodium bicarbonate solution and dichloromethane. The organic phase was separated, dried (magnesium sulfate) and concentrated in vacuo to yield the product as light-brown solid which was used without further purification. LC/MS 244.8 (M+1).

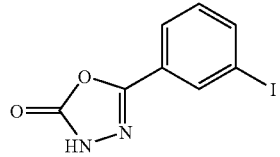

INTERMEDIATE 7

5-(3-Iodophenyl)-1,3,4-oxadiazol-2(3H)-one

Step A: 3-Iodobenzhydrazide

A suspension of 3-iodobenzoic acid (1.24 g, 5.0 mmol) in 15 mL of dichloromethane containing one drop of N,N-dimethylformamide was treated dropwise with oxalyl chloride (0.70 mL, 7.5 mmol). After stirring for 2.5 h at room temperature, the solution was concentrated under reduced pressure to afford a pale orange oil, which was dissolved in 10 mL of dry tetrahydrofuran (THF) and added dropwise to an ice-cold suspension of tert-butyl carbazate (793 mg, 6.0 mmol) and triethylamine (1.10 mL) in 15 mL of dry THF. The resultant mixture was allowed to warm to room temperature overnight, and was then concentrated under reduced pressure. The residue was partitioned between ethyl acetate and water, and the organic layer was washed sequentially with 5% aqueous hydrochloric acid, saturated aqueous sodium bicarbonate solution, and saturated aqueous brine, dried (magnesium sulfate), and concentrated under reduced pressure to afford an off-white solid. Trituration with hexanes afforded a white powder, which was suspended in 60 mL of dichloromethane and cooled in an ice-water bath. Trifluoroacetic acid (25 mL) was added dropwise, and the mixture was warmed to room temperature. After 1 h, the solution was concentrated under reduced pressure, and the residue was dissolved in 60 mL of water and was neutralized to pH 8 with 1N aqueous sodium hydroxide solution. The resultant precipitate was collected, washed with water, and dried in vacuo to afford 3-iodobenzhydrazide as a white powder.

Step B: 5-(3-Iodophenyl)-1,3,4-oxadiazol-2(3H)-one

A solution of N,N-carbonyldiimidazole (800 mg, 5.0 mmol) in 5 mL of dry THF was added dropwise to an ice-cold solution of the product from Step A (1.048 g, 4.0 mmol) and triethylamine (0.60 mL, 4.0 mmol) in 12 mL of dry THF. The resultant mixture was allowed to warm to room temperature overnight, and was then concentrated under reduced pressure. The residue was partitioned between diethyl ether and water, and the ether layer was washed sequentially with 5% aqueous hydrochloric acid, saturated aqueous sodium bicarbonate solution, and saturated aqueous brine, dried (magnesium sulfate), and concentrated under reduced pressure to afford a white powder. Recrystallization from ethyl acetate-hexanes afforded the title compound as a fluffy white solid. LC/MS 289.2 (M+1).

INTERMEDIATE 8

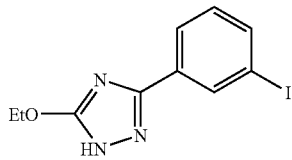

5-Ethoxy-3-(3-iodophenyl)-1H-1,2,4-triazole

Step A: 2-Amino-5-(3-iodophenyl)-1,2,4-oxadiazole

A solution of cyanogen bromide (1.06 g, 10.0 mmol) in 10 mL of methanol was added dropwise to an ice-cold suspension of 3-iodobenzhydrazide (2.62 g, 10.0 mmol, Intermediate 7, Step A) in 20 mL of methanol. After 30 min, the mixture was allowed to warm to room temperature and was then warmed at reflux for 1.5 h. The resultant solution was cooled to 0° C., and neutralized to pH 9 with concentrated aqueous ammonium hydroxide. The resultant precipitate was collected, washed with methanol, and dried in vacuo to afford the product as an off-white powder. LC/MS 288.0 (M+1).

Step B: 5-Ethoxy-3-(3-iodophenyl)-1H-1,2,4-triazole

The product (1.00 g, 3.48 mmol) from Step A was added to a solution of potassium hydroxide (1.0 g) in 30 mL of absolute ethanol. The mixture was warmed to reflux and, after 5 h, cooled to room temperature. The solution was then acidified with glacial acetic acid, and concentrated under reduced pressure. The product was extracted into ethyl acetate, and the combined ethyl acetate extracts were washed sequentially with water and saturated aqueous brine, dried (magnesium sulfate) and concentrated to give the crude product as an orange semisolid. Purification by flash chromatography (silica gel, 15% ethyl acetate-hexanes) afforded the product as an off-white, sticky foam. LC/MS 316.0 (M+1).

INTERMEDIATE 9

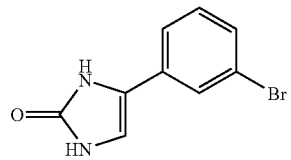

4-(3-Bromophenyl)-1,3-dihydro-2H-imidazol-2-one

To a mixture of 3-bromophenacyl bromide (0.5 g, 1.8 mmol), urea (0.32 g, 5.3 mmol), and ammonium acetate (0.40 g, 5.4 mmol) in water (10 mL) was added glacial acetic acid (0.32 g, 5.4 mmol). The reaction mixture was heated at reflux overnight. After cooling to room temperature, the mixture was extracted with three portions of ethyl acetate, and the combined extracts were dried (magnesium sulfate) and concentrated under reduced pressure to give a brown residue which was triturated with diethyl ether to afford the desired product. LC/MS 238.9 and 240.9 (M+1).

INTERMEDIATE 10

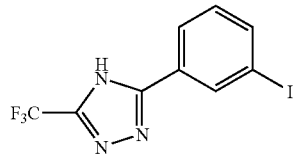

3-(3-Iodophenyl)-5-(trifluoromethyl)-4H-1,2,4-triazole

Step A: Ethyl 3-Iodobenzimidate hydrochloride

Hydrogen chloride gas was bubbled into a solution of 3-iodobenzonitrile (2.00 g, 8.73 mmol) in 20 mL of absolute ethanol for 30 min at room temperature. The resultant solution was kept at room temperature for 48 h, and was then concentrated under reduced pressure. The residue was triturated with diethyl ether, collected and dried in vacuo to afford the product as a white powder.

Step B: 3-Iodobenzamidine hydrochloride

Ammonia gas was bubbled into an ice-cold suspension of the product (1.00 g, 3.21 mmol) from Step A in 20 mL of absolute ethanol for 20 min. The resultant clear solution was allowed to warm to room temperature and stirred for 48 h. The reaction mixture was then concentrated under reduced pressure, and the residue was triturated with diethyl ether. The supernatant was decanted, and the residual gummy product was dried in vacuo to afford the title compound as white foam.

Step C: 3-(3-Iodophenyl)-5-(trifluoromethyl)4H-1,2,4-triazole

To a solution of ethyl trifluoroacetate (0.12 mL, 1.00 mmol) in 4.0 mL of dry tetrahydrofuran was added anhydrous hydrazine (25 mL, 0.80 mmol), and the resultant solution was heated to reflux. After one hour, the solution was cooled to room temperature and was added via syringe to a mixture of the amidine hydrochloride (283 mg, 1.00 mmol) from Step B and solid sodium hydroxide (50 mg) in 3.0 mL of dry tetrahydrofuran. The reaction mixture was warmed at reflux for 3 h, and was then allowed to cool to room temperature overnight. The precipitated solids were removed by filtration, and the filtrate was concentrated under reduced pressure to afford a yellow gum, which was partitioned between ethyl acetate and water. The organic layer was washed with saturated aqueous brine, dried (magnesium sulfate) and concentrated under reduced pressure to provide the crude product, which was purified by flash chromatography (silica gel, step gradient, 0 to 20% ethyl acetate/hexanes) to afford the product as a white solid. LC/MS 339.8 (M+1).

INTERMEDIATE 11

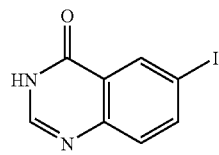

6-Iodoquinazolin-4(3H)-one

A mixture of 2-amino-5-iodobenzoic acid (2.0 g, 7.6 mmol) and formamidine acetate (0.99 g, 9.5 mmol) in absolute ethanol (80 mL) was heated at reflux for 2 h. The reaction was then cooled in an ice bath, and water (10 mL) was added with stirring. The resultant precipitate was collected by filtration to afford the desired product as pale crystals. LC/MS 272.7 (M+1).

INTERMEDIATE 12

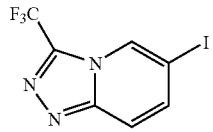

6-Iodo-3-(trifluoromethyl)[1,2,4]triazolo[4,3-α]pyridine

Step A: 2,2,2-Trifluoro-N'-(5-iodopyridin-2-yl)acetohydrazide

To a solution of 5-iodo-2-hydrazinopyridine (235 mg, 1 mmol) in trifluoroacetic acid (1.5 mL) in a thick-walled resealable tube was added trifluoroacetic anhydride (0.356 mL, 2.5 mmol). The mixture was warmed to 50° C. After 18 h, the mixture was concentrated to dryness under reduced pressure. The resultant residue was purified by preparative thin layer chromatography (silica, 5% methanol/dichloromethane) to afford the product. LC/MS 331.8 (M+1)

Step B: 6-Iodo-3-(trifluoromethyl)[1,2,4]triazolo[4,3-α]pyridine

The product (145 mg, 0.438 mmol) from Step A was suspended in superphosphoric acid (5 mL), and the mixture was heated at 140° C. for 6 h. The mixture was allowed to cool to room temperature, poured into ice, and neutralized with concentrated aqueous ammonium hydroxide solution. The mixture was extracted several times with ethyl acetate, and the combined extracts were washed with saturated aqueous brine, dried (magnesium sulfate), and concentrated under reduced pressure. The resultant residue was purified by preparative thin layer chromatography (silica, 8% methanol/dichloromethane) to afford the title compound. LC/MS 313.8 (M+1).

INTERMEDIATE 13

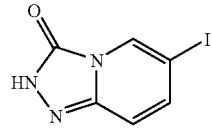

6-Iodo[1,2,4]triazolo[4.3-α]pyridin-3(2H)-one

To a solution of 5-iodo-2-hydrazinopyridine (470 mg, 2 mmol) in dichloromethane (30 mL) was added a solution of N,N-carbonyldiimidazole (389 mg, 2.4 mmol) in 20 mL of dichloromethane. After stirring at room temperature for 2 h, the mixture was washed sequentially with water, 0.5N aqueous hydrochloric acid and saturated aqueous sodium bicarbonate solution. The organic phase was dried (magnesium sulfate) and concentrated under reduced pressure to afford the product. The resultant yellow crystals that precipitated from the aqueous phase upon standing overnight were collected and dried in vacuo to afford additional product. LC/MS 261.8 (M+1).

INTERMEDIATE 14

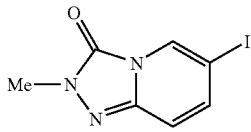

6-Iodo-2-methyl[1,2,4]triazolo[4,3-α]pyridin-3(2H)-one

To a solution of 6-iodo[1,2,4]triazolo[4,3-α]pyridin-3(2H)-one (Intermediate 13, 360 mg, 1.379 mmol) in anhydrous dimethylformamide (DMF, 4 mL) was added sequentially cesium carbonate (1.35 g, 4.14 mmol) and iodomethane (0.52 mL), and the reaction mixture was stirred at room temperature overnight. The reaction mixture was then diluted with ethyl acetate, and the precipitated solids were removed by filtration. The filtrate was washed with saturated aqueous brine, dried (magnesium sulfate), and concentrated to dryness under reduced pressure. The residue was purified by preparative thin layer chromatography (silica gel, 3% methanol/dichloromethane) to afford the title compound. LC/MS 257.8 (M+1).

INTERMEDIATE 15

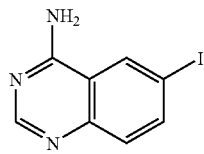

7-Iodoquinazolin-4(3H)-one

Step A: 4-Chloro-6-iodoquinazoline

A mixture of 6-iodoquinazolin-4(3H)-one (Intermediate 11, 100 mg, 0.37 mmol) and phenylphosphonic dichloride (1.5 mL) was heated at 150° C. for one h. After cooling the reaction mixture in an ice bath, isopropyl ether was added. The resultant crystalline precipitate was collected by filtration, and was then stirred with saturated aqueous sodium bicarbonate solution. The solution was extracted with three portions of ethyl acetate, and the combined extracts were dried (magnesium sulfate) and concentrated under reduced pressure to give the crude product. Purification by preparative thin layer chromatography (silica gel, 5% and 10% ethyl acetate/hexanes) afforded the desired product. LC/MS 291 (M+1).

Step B: 7-Iodoquinazolin-4(3H)-one

To the product (73.8 mg) from Step A was added a solution of 2M ammonia in ethanol (7 mL) and the resultant solution was stirred at room temperature for 2 h. The volatiles were removed under reduced pressure and the residue was triturated with diethyl ether to give the desired product as a white powder. LC/MS 271.8 (M+1).

INTERMEDIATE 16

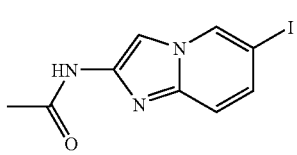

N-(6-Iodoimidazo[1,2-α]pyridin-2-yl)acetamide

Step A: 5-Iodo-2-p-toluenesulfonamidopyridine p-Toluenesulfonyl chloride (2.00 g, 10.4 mmol) was added to a solution of 5-iodo-2-aminopyridine (2.50 g, 11.4 mmol) in 6 mL of pyridine, and the resultant solution was warmed at 90° C. for 18 h. After cooling to room temperature, the solution was added portionwise to 75 mL of ice-water with stirring. The resultant precipitate was collected, washed with water, and dried in vacuo to afford a pale yellow powder, which was stirred with 20 mL of methanol for several minutes. The solid product was then collected, washed with methanol, and dried in vacuo to provide the title compound as an off-white powder. LC/MS 374.8 (M+1).

Step B: 1-(Carbamylmethyl)-5-iodo-2-(p-toluenesulfonamido)pyridine

To a solution of the product (1.60 g, 4.27 mmol) from Step A in 8.0 mL of dry N,N-dimethylformamide was added sodium hydride (188 mg of 60 weight % dispersion in mineral oil, 4.44 mmol). After 15 min, the solution was warmed to 60° C. for 10 min, and was then cooled to room temperature. Chloroacetamide (420 mg) was added in one portion, and the solution was then warmed to 100° C. After 2.5 h, the solution was cooled to room temperature and poured into 70 mL of ice-water. The resultant precipitate was collected, washed with water and air-dried overnight. The crude product was subsequently stirred with 20 mL of methanol for several minutes, and the product was collected by filtration to afford the title compound as a white powder. LC/MS 414.9 (M+1-$H_2O$).

Step C: N-(6-Iodoimidazo[1,2-α]pyridin-2-yl)acetamide

A mixture of the product from Step B (300 mg, 0.70 mmol) and 1.0 mL of acetic anhydride was warmed at reflux for 2.5 h. The solution was cooled to room temperature and concentrated under reduced pressure. The residue was partitioned between ethyl acetate and water, and the ethyl acetate layer was washed sequentially with saturated aqueous sodium bicarbonate solution and saturated aqueous brine, dried (magnesium sulfate) and concentrated under reduced pressure. The crude residue was purified by preparative thin-layer chromatography (silica gel, 7% methanol/dichloromethane) to afford the title compound as a pale yellow powder. LC/MS 301.9 (M+1).

INTERMEDIATE 17

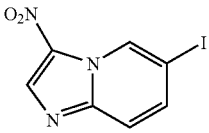

6-Iodo-3-nitroimidazo[1,2-α]pyridine

To a solution of 6-iodoimidazo[1,2-α]pyridine (Intermediate 6, 448 mg, 1.84 mmol) in concentrated sulfuric acid (1.8 mL) at 15° C. was added concentrated nitric acid (0.54 mL) dropwise. After the addition was complete, the reaction mixture was stirred at room temperature for one hour and was poured onto 10 g of ice. The pH of the mixture was adjusted to 4 with aqueous potassium hydroxide solution and the resultant solids were collected by filtration, washed with water and dried. The crude product was recrystallized from dichloromethane/hexanes to afford the title compound. LC/MS 289.8 (M+1).

INTERMEDIATE 18

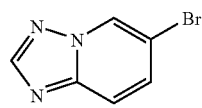

6-Bromo[1,2,4]triazolo[1,5-α]pyridine

Step A: N'-(5-Bromopyridin-2-yl)-N,N-dimethylimidoformamide

To a stirred solution of 5-bromo-2-aminopyridine (3.0 g, 17.3 mmol) in N,N-dimethylformamide (6 mL) was added N,N-dimethylformamide dimethyl acetal (5.37 g, 45.0 mmol). The reaction mixture was heated to 130° C. overnight. After cooling to room temperature, the volatiles were removed under reduced pressure to afford the desired product as a brown oil. LC/MS 227.8 (M+1)

Step B: 6-Bromo[1,2,4]triazolo[1,5-α]pyridine

To an ice-cooled, stirred solution of the crude product from Step A (3.94 g, 17.3 mmol) in methanol (30 mL) and pyridine (2.73 g, 35.6 mmol) was added hydroxylamine-O-sulfonic acid (2.54 g, 22.5 mmol). The reaction mixture was allowed to warm to room temperature and was stirred overnight. The volatiles were removed under reduced pressure, and the residue was partitioned between aqueous sodium bicarbonate solution and ethyl acetate. The aqueous layer was further extracted with ethyl acetate, and the combined organic layers were washed sequentially with water (100 mL) and saturated aqueous brine solution (100 mL), dried (magnesium sulfate) and concentrated in vacuo to yield a brown solid, which was recrystallized from dichloromethane to afford the title compound as an orange solid. LC/MS 197.9 and 199.9 (M+1).

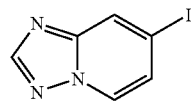

INTERMEDIATE 19

7-Iodo[1,2,4]triazolo[1,5-α]pyridine

Step A: 2-(tert-Butoxycarbonyl)amino-4-iodopyridine

To a stirred solution of 4-iodopicolinic acid hemi-hydroiodide hydrate (Lohse, O. *Synth. Commun.* 1996, 26, 2017; 24.5 g, 78.3 mmol) in 140 mL of tert-butanol, 130 mL of toluene and 35 mL of triethylamine was added diphenylphosphoryl azide (27 mL, 125 mmol) dropwise over 30 min. The resultant solution was then warmed to 65° C. and, after 1.5 h, the bath temperature was raised to 100° C. After 4 h, the solution was cooled and concentrated under reduced pressure, and the residue was partitioned between ethyl acetate (600 mL) and water (300 mL). The ethyl acetate layer was washed sequentially with saturated aqueous sodium bicarbonate solution (200 mL) and saturated aqueous brine (200 mL), dried over magnesium sulfate and concentrated to afford a brown solid. Purification by flash chromatography (silica gel; 5% ethyl acetate-hexanes eluant) afforded a pale yellow solid, which was triturated with hexanes to afford the title compound as a white solid. MS 265.1 (M+1-tBu).

Step B: 2-Amino-4-iodopyridine

To an ice-cold solution of the product from Step A above (3.84 g, 12.0 mmol) in 25 mL of dichloromethane was added trifluoroacetic acid (12 mL) dropwise. The resultant solution was allowed to warm to room temperature and, after 1 h, the volatiles were removed under reduced pressure. The residue was dissolved in water (120 mL), and the solution was neutralized by portionwise addition of sodium bicarbonate. The mixture was extracted with ethyl acetate, and the extract was washed with saturated aqueous brine, dried over magnesium sulfate and concentrated to afford an off-white solid, which was triturated with hexanes to afford the title compound as a white powder. MS 221.1 (M+1).

Step C: 7-Iodo[1,2,4]triazolo[1,5-α]pyridine

To a stirred solution of the product from Step B above (220 mg, 1.00 mmol) in N,N-dimethylformamide (0.5 mL) was added N,N-dimethylformamide dimethyl acetal (0.37 mL, 2.60 mmol). The reaction mixture was heated to 130° C. overnight. After cooling to room temperature, the volatiles were removed under reduced pressure to afford a red oil, which was dissolved in 2.0 mL of methanol and 0.162 mL of pyridine. The solution was cooled in an ice bath and hydroxylamine-O-sulfonic acid (147 mg, 1.30 mmol) was added in one portion. The reaction mixture was allowed to warm to room temperature and was stirred overnight. The volatiles were removed under reduced pressure, and the residue was partitioned between saturated aqueous brine solution and ethyl acetate. The aqueous layer was further extracted with ethyl acetate, and the combined organic layers were washed with saturated aqueous brine solution (100 mL), dried over magnesium sulfate and concentrated under reduced pressure to afford the title compound as an orange solid. MS 246.1 (M+1).

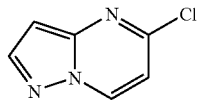

INTERMEDIATE 20

5-Chloropyrazolo[1,5-a]pyrimidine

Step A: 5-Hydroxypyrazolo[1,5-a]pyrimidine

To a stirred solution of 3-aminopyrazole (11.5 g, 0.138 mol) in 65 mL of 1,4-dioxane was added ethyl propiolate (14.7 g, 15.2 mL, 0.150 mol) dropwise, and the resultant light yellow solution was warmed to reflux. After 4 h, the blood-red solution was cooled to room temperature and 100 mL of toluene was added with stirring. The resultant precipitate was collected with toluene and air-dried to afford the title compound as a tan solid. MS 136.0 (M+1)

Step B: 5-Chloropyrazolo[1,5-a]pyrimidine

A mixture of the product (1.35 g, 10.0 mmol) from Step A above and 7.5 mL of phosphorus oxychloride was warmed at reflux for 4 h. The mixture was cooled, and the volatiles were removed under reduced pressure. The dark residue was partitioned between ice water and dichloromethane, and the aqueous layer was extracted with additional dichloromethane. The combined organic extracts were dried over sodium sulfate and concentrated under reduced pressure to provide a light brown solid, which was purified by flash chromatography (silica gel; 0.5% methanol in dichloromethane eluant) to afford the title compound as a white solid. MS 153.8 and 155.8 (M+1).

Essentially following the procedures outlined for Examples 1–17, the Examples listed in Table 1–3 were prepared.

TABLE 1

| Ex. | R⁴ | R² | X | MS (M + 1) |
|---|---|---|---|---|
| 18 | 4-(SO₂Me)-phenyl | Me | (S)—CHF | 405.1 |
| 19 | 3-(SO₂Me)-phenyl | Me | (S)—CHF | 405.1 |
| 20 | pyrazin-5-yl | Me | (S)—CHF | 329.2 |
| 21 | 3-chloropyridin-4-yl | Me | (S)—CHF | 362.1 |
| 22 | 2,4-difluorophenyl | Me | (S)—CHF | 363.0 |
| 23 | 3,4-difluorophenyl | Me | (S)—CHF | 363.1 |
| 24 | 2,5-difluorophenyl | Me | (S)—CHF | 363.0 |
| 25 | 3,5-difluorophenyl | Me | (S)—CHF | 363.0 |
| 26 | 3-(ethoxycarbonyl)phenyl | Me | (S)—CHF | 399.2 |
| 27 | 4-(ethoxycarbonyl)phenyl | Me | (S)—CHF | 399.1 |
| 28 | 3-(NHSO₂Me)-phenyl | Me | (S)—CHF | 420.1 |
| 29 | 4-(NHSO₂Me)-phenyl | Me | (S)—CHF | 420.1 |
| 30 | 4-CO₂H-phenyl | Me | (S)—CHF | 371.0 |
| 31 | pyridin-3-yl | Me | (S)—CHF | 328.1 |
| 32 | 6-OMe-pyridin-3-yl | Me | (S)—CHF | 358.1 |
| 33 | 2-Cl-phenyl | Me | (S)—CHF | 361.1 |
| 34 | 2-F-phenyl | Me | (S)—CHF | 345.1 |
| 35 | 3-CN-phenyl | Me | (S)—CHF | 352.1 |
| 36 | pyridin-4-yl | Me | (S)—CHF | 328.1 |
| 37 | pyridin-2-yl | Me | (S)—CHF | 328.1 |
| 38 | 2,4-difluorophenyl | Cyclopropylmethyl | (S)—CHF | 403.1 |
| 39 | 3-(MeSO₂)phenyl | Cyclopropylmethyl | (S)—CHF | 444.9 |
| 40 | 4-fluoro-(3-tetrazol-5-yl)phenyl | Me | (S)—CHF | 413.1 |
| 41 | 3-(aminosulfonyl)phenyl | Me | (S)—CHF | 406.1 |
| 42 | 2-fluoro-(5-tetrazol-5-yl)phenyl | Me | (S)—CHF | 413.3 |
| 43 | 3-hydroxyphenyl | Me | (S)—CHF | 343.1 |
| 44 | 6-fluoropyridin-3-yl | Me | (S)—CHF | 346.2 |
| 45 | 3-(aminocarbonyl)phenyl | Me | (S)—CHF | 370.2 |
| 46 | 3-(phenylaminocarbonyl)phenyl | Me | (S)—CHF | 446.3 |
| 47 | 4-fluoro-3-(5-oxo-4,5-dihydro-1,2,4-oxadiazol-3-yl)phenyl | Me | (S)—CHF | 429.2 |
| 48 | 3-[(thiazol-2-yl)aminocarbonyl]phenyl | Me | (S)—CHF | 453.2 |
| 49 | 3-[(tetrazol-5-yl)aminocarbonyl]phenyl | Me | (S)—CHF | 438.2 |
| 50 | imidazo[1,2-a]pyridin-6-yl | Me | (S)—CHF | 367.2 |
| 51 | 2-methoxyphenyl | Me | (S)—CHF | 357.2 |
| 52 | 3-(5-oxo-4,5-dihydro-1,3,4-oxadiazol-2-yl)phenyl | Me | (S)—CHF | 411.1 |
| 53 | 3-(5-ethoxy-1H-1,2,4-triazol-3-yl)phenyl | Me | (S)—CHF | 438.3 |
| 54 | 1-ethyl-6-oxo-1,6-dihydropyridin-3-yl | Me | (S)—CHF | 372.2 |
| 55 | quinolin-6-yl | Me | (S)—CHF | 378.2 |
| 56 | 3-(2-oxo-2,3-dihydro-1H-imidazol-4-yl)phenyl | Me | (S)—CHF | 409.3 |
| 57 | 2-methylphenyl | Me | (S)—CHF | 341.2 |
| 58 | 2-(trifluoromethyl)phenyl | Me | (S)—CHF | 395.1 |
| 59 | 3-[5-(trifluoromethyl)-4H-1,2,4-triazol-3-yl]phenyl | Me | (S)—CHF | 462.1 |
| 60 | 4-oxo-3,4-dihydroquinazolin-6-yl | Me | (S)—CHF | 395.1 |
| 61 | 4-fluorophenyl | CONHEt | (S)—CHF | 402.2 |
| 62 | 1-methyl-6-oxo-1,6-dihydropyridin-3-yl | Et | (S)—CHF | 372.1 |
| 63 | 6-oxo-1,6-dihydropyridin-3-yl | Et | (S)—CHF | 358.1 |
| 64 | 3-(trifluoromethyl)[1,2,4]triazolo[4,3-a]pyridin-6-yl | Me | (S)—CHF | 436.2 |
| 65 | 4-fluorophenyl | CONH₂ | (S)—CHF | 374.2 |
| 66 | 3-oxo-2,3-dihydro[1,2,4]triazolo[4,3-a]pyridin-6-yl | Me | (S)—CHF | 384.1 |
| 67 | 1-methyl-6-oxo-1,6-dihydropyridin-3-yl | Me | CF₂ | 376.0 |
| 68 | 6-oxo-1,6-dihydropyridin-3-yl | Me | CF₂ | 362.0 |
| 69 | 4-aminoquinazolin-6-yl | Me | (S)—CHF | 394.1 |
| 70 | 5-bromo-1-methyl-6-oxo-1,6-dihydropyridin-3-yl | Me | (S)—CHF | 423.9 |
| 71 | 4-fluorophenyl | (pyrrolidin-1-yl)carbonyl | (S)—CHF | 428.3 |
| 72 | 4-fluorophenyl | (azetidin-1-yl)carbonyl | (S)—CHF | 414.3 |
| 73 | 2-(acetylamino)imidazo[1,2-a]pyridin-6-yl | Me | (S)—CHF | 424.2 |
| 74 | 2-methyl-3-oxo-2,3-dihydro[1,2,4]triazolo[4,3-a]pyridin-6-yl | Me | (S)—CHF | 398.1 |
| 75 | 3-aminoimidazo[1,2-α]pyridin-6-yl | Me | (S)—CHF | 382.1 |
| 76 | 4-fluorophenyl | [(tetrazol-5-yl)amino]carbonyl | (S)—CHF | 442.3 |
| 77 | 4-fluorophenyl | CONHMe | (S)—CHF | 388.2 |
| 78 | 4-fluorophenyl | CONEt₂ | (S)—CHF | 430.3 |
| 79 | 4-fluorophenyl | COOMe | (S)—CHF | 389.2 |
| 80 | [1,2,4]triazolo[1,5-a]pyridin-6-yl | Me | (S)—CHF | 368.1 |
| 81 | 4-fluorophenyl | COOH | CH₂ | 357.1 |
| 82 | 4-fluorophenyl | COOH | CF₂ | 393.0 |
| 83 | 4-fluorophenyl | CONMe₂ | CH₂ | 384.1 |
| 84 | 3-carboxypyrazolo[1,5-a]pyridin-5-yl | Me | (S)—CHF | 411.1 |
| 85 | 6-oxo-1,6-dihydropyridin-3-yl | Me | CH₂ | 326.1 |
| 86 | [1,2,4]triazolo[1,5-a]pyridin-6-yl | CONMe₂ | (S)—CHF | 425.3 |
| 87 | [1,2,4]triazolo[1,5-a]pyridin-7-yl | CONMe₂ | (S)—CHF | 425.3 |
| 88 | pyrazolo[1,5-α]pyrimidin-5-yl | CONMe₂ | (S)—CHF | 425.2 |
| 89 | phenyl | Me | (S)—CHF | 327.0 |
| 90 | [1,2,4]triazolo[1,5-a]pyridin-6-yl | CONMe₂ | CH₂ | 407.4 |
| 91 | [1,2,4]triazolo[1,5-a]pyridin-6-yl | (3-fluoro-azetindin-1-yl)carbonyl | CH₂ | 441.2 |
| 92 | [1,2,4]triazolo[1,5-a]pyridin-6-yl | (pyrrolidine-1-yl)carbonyl | CF₂ | 469.4 |
| 93 | [1,2,4]triazolo[1,5-a]pyridin-6-yl | CONMeCH₂Ph | CF₂ | 519.1 |
| 94 | [1,2,4]triazolo[1,5-a]pyridin-6-yl | (morpholin-4-yl)carbonyl | CF₂ | 485.2 |

TABLE 2

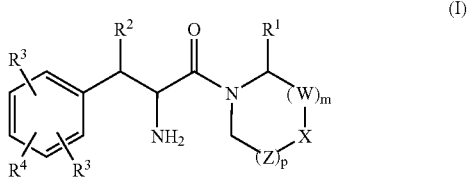

| Example | R⁴ | R² | X | MS (M + 1) |
|---|---|---|---|---|
| 95 | 4-fluorophenyl | Me | CHF | 331.2 |
| 96 | 1-methyl-6-oxo-1,6-dihydro-pyridin-3-yl | Me | CHF | 344.0 |
| 97 | [1,2,4]triazolo[4,3-a]pyridin-6-yl | Me | CHF | 354.2 |
| 98 | imidazo[1,2-a]pyridin-6-yl | Me | CHF | 353.1 |
| 99 | 4-fluorophenyl | COOH | CHF | 361.1 |
| 100 | 4-fluorophenyl | CONMe₂ | CHF | 388.1 |
| 101 | [1,2,4]triazolo[1,5-a]pyridin-6-yl | CONMe₂ | CHF | 443.2 |

TABLE 3

| Example | R⁴ | R² | X | MS (M + 1) |
|---|---|---|---|---|
| 102 | 4-fluorophenyl | Me | CHF | 359.2 |
| 103 | 1-methyl-6-oxo-1,6-dihydropyridin-3-yl | Me | CHF | 372.1 |
| 104 | [1,2,4]triazolo[4,3-a]pyridin-6-yl | Me | CHF | 382.1 |
| 105 | imidazo[1,2-a]pyridin-6-yl | Me | CHF | 381.1 |

Example of a Pharmaceutical Formulation

As a specific embodiment of an oral pharmaceutical composition, a 100 mg potency tablet is composed of 100 mg of any of the compounds of the present invention, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:

1. A compound of structural formula I:

(I)

or a pharmaceutically acceptable salt thereof; wherein
each n is independently 0, 1, or 2;
m and p are each independently 0 or 1, with the proviso that the sum of m and p is 1;
X is $CH_2$, S, CHF, or $CF_2$;
W and Z are each independently $CH_2$, CHF, or $CF_2$;
$R^1$ is hydrogen or cyano;
each $R^3$ is independently selected from the group consisting of hydrogen, halogen, $C_{1-4}$ alkyl, $C_{1-4}$ alkoxy, cyano, trifluoromethyl, trifluoromethoxy, and hydroxy;
$R^4$ is aryl, heteroaryl, or heterocyclyl, wherein aryl, heteroaryl, and heterocyclyl are unsubstituted or substituted with one to five $R^5$ substituents;
$R^2$ is selected from the group consisting of
  $C_{1-10}$ alkyl, wherein alkyl is unsubstituted or substituted with one to five substituents independently selected from halogen or hydroxy,
  $C_{2-10}$ alkenyl, wherein alkenyl is unsubstituted or substituted with one to five substituents independently selected from halogen or hydroxy,
  $(CH_2)_n$-aryl, wherein aryl is unsubstituted or substituted with one to five substituents independently selected hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$-heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$-heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$—$C_{3-6}$ cycloalkyl, wherein cycloalkyl is unsubstituted or substituted with one to three substituents independently selected from halogen, hydroxy, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
  $(CH_2)_n$COOH,
  $(CH_2)_n$COO$C_{1-6}$ alkyl,
  $(CH_2)_n$CON$R^6R^7$, wherein $R^6$ and $R^7$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;

or wherein $R^6$ and $R^7$ together with the nitrogen atom to which they are attached form a heterocyclic ring selected from azetidine, pyrrolidine, piperidine, piperazine, and morpholine wherein said heterocyclic ring is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens; and wherein any methylene ($CH_2$) carbon atom in $R^2$ is unsubstituted or substituted with one to two groups independently selected from halogen, hydroxy, and $C_{1-4}$ alkyl unsubstituted or substituted with one to five halogens;

each $R^5$ is independently selected from the group consisting of
halogen,
cyano,
oxo,
hydroxy,
$C_{1-6}$ alkyl, wherein alkyl is unsubstituted or substituted with one to five halogens,
$C_{1-6}$ alkoxy, wherein alkoxy is unsubstituted or substituted with one to five halogens,
$(CH_2)_n$—$NR^6R^7$,
$(CH_2)_n$—$CONR^6R^7$,
$(CH_2)_n$—$OCONR^6R^7$,
$(CH_2)_n$—$SO_2NR^6R^7$,
$(CH_2)_n$—$SO_2R^9$,
$(CH_2)_n$—$NR^8SO_2R^9$,
$(CH_2)_n$—$NR^8CONR^6R^7$,
$(CH_2)_n$—$NR^8COR^8$,
$(CH_2)_n$—$NR^8CO_2R^9$,
$(CH_2)_n$—$COOH$,
$(CH_2)_n$—$COOC_{1-6}$ alkyl,
$(CH_2)_n$-aryl, wherein aryl is unsubstituted or substituted with one to five substituents independently selected from halogen, hydroxy, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
$(CH_2)_n$-heteroaryl, wherein heteroaryl is unsubstituted or substituted with one to three substituents independently selected from hydroxy, halogen, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
$(CH_2)_n$-heterocyclyl, wherein heterocyclyl is unsubstituted or substituted with one to three substituents independently selected from oxo, hydroxy, halogen, $CO_2H$, $C_{1-6}$ alkyloxycarbonyl, $C_{1-6}$ alkyl, $C_{3-6}$ cycloalkyl, and $C_{1-6}$ alkoxy, wherein alkyl and alkoxy are unsubstituted or substituted with one to five halogens,
$(CH_2)_n$—$C_{3-6}$ cycloalkyl, wherein cycloalkyl is unsubstituted or substituted with one to three substituents independently selected from halogen, hydroxy, $C_{1-6}$ alkyl, and $C_{1-6}$ alkoxy, wherein alkyl and alkoxy are unsubstituted or substituted with one to five halogens, wherein any methylene ($CH_2$) carbon atom in $R^5$ is unsubstituted or substituted with one to two groups independently selected from halogen, hydroxy, and $C_{1-4}$ alkyl unsubstituted or substituted with one to five halogens;

each $R^9$ is independently selected from the group consisting of tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five halogens and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens, and wherein any methylene ($CH_2$) carbon atom in $R^8$ is unsubstituted or substituted with one to two groups independently selected from halogen, hydroxy, and $C_{1-4}$ alkyl unsubstituted or substituted with one to five halogens; and each $R^8$ is hydrogen or $R^9$.

2. The compound of claim 1 wherein the carbon atom marked with an * has the stereochemical configuration as depicted in formula Ia:

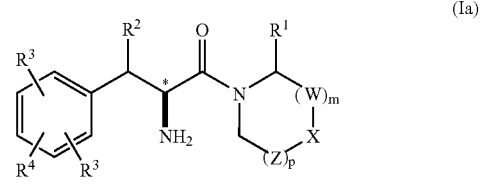

and $R^3$ is hydrogen or fluorine.

3. The compound of claim 2 wherein the carbon atom attached to $R^1$ marked with an ** has the stereochemical configuration as depicted in formula Ib:

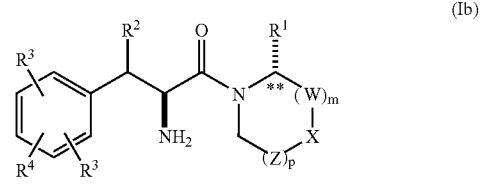

4. The compound of claim 1 of the structural formula Ic:

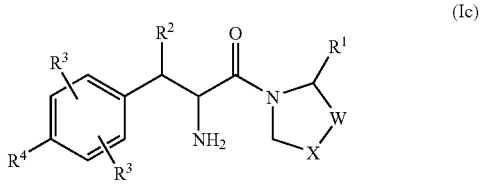

wherein $R^3$ is hydrogen or fluorine.

5. The compound of claim 4 wherein the carbon atoms marked with an * have the stereochemical configuration as depicted in structural formula Id:

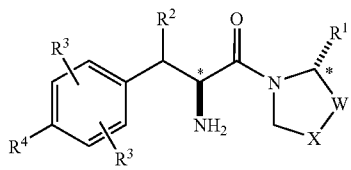

(Id)

6. The compound of claim 5 wherein $R^1$ is hydrogen, W is $CH_2$, and X is $CH_2$, CHF or $CF_2$.

7. The compound of claim 1 wherein $R^2$ is selected from the group consisting of
$C_{1-6}$ alkyl, wherein alkyl is unsubstituted or substituted with one to five substituents independently selected from halogen or hydroxy,
$C_{2-6}$ alkenyl, wherein alkenyl is unsubstituted or substituted with one to five substituents independently selected from halogen or hydroxy,
$(CH_2)_n$—$C_{3-6}$ cycloalkyl, wherein cycloalkyl is unsubstituted or substituted with one to three substituents independently selected from halogen, hydroxy, $CO_2H$, $C_{1-6}$ alkyloxycarbonyl, $C_{1-6}$ alkyl, and $C_{1-6}$ alkoxy, wherein alkyl and alkoxy are unsubstituted or substituted with one to five halogens,
$(CH_2)_n COOH$,
$(CH_2)_n COOC_{1-6}$ alkyl,
$(CH_2)_n CONR^6R^7$, wherein $R^6$ and $R^7$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or wherein $R^6$ and $R^7$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens; and
wherein any methylene ($CH_2$) carbon atom in $R^2$ is unsubstituted or substituted with one to two groups independently selected from halogen, hydroxy, and $C_{1-4}$ alkyl unsubstituted or substituted with one to five halogens.

8. The compound of claim 7 wherein $R^2$ is selected from the group consisting of
$C_{1-3}$ alkyl, wherein alkyl is unsubstituted or substituted with one to five substituents independently selected from halogen or hydroxy,
$CH_2$—$C_{3-6}$ cycloalkyl,
COOH,
$COOC_{1-6}$ alkyl,
$CONR^6R^7$, wherein $R^6$ and $R^7$ are independently selected from the group consisting of hydrogen, tetrazolyl, thiazolyl, $(CH_2)_n$-phenyl, $(CH_2)_n$—$C_{3-6}$ cycloalkyl, and $C_{1-6}$ alkyl, wherein alkyl is unsubstituted or substituted with one to five substituents independently selected from halogen and hydroxy and wherein phenyl and cycloalkyl are unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens;
or wherein $R^6$ and $R^7$ together with the nitrogen atom to which they are attached form a heterocyclic ring selected from azetidine, pyrrolidine, piperidine, piperazine, and morpholine wherein said heterocyclic ring is unsubstituted or substituted with one to five substituents independently selected from halogen, hydroxy, $C_{1-6}$ alkyl, and $C_{1-6}$ alkoxy, wherein alkyl and alkoxy are unsubstituted or substituted with one to five halogens.

9. The compound of claim 1 of the structural formula Ii:

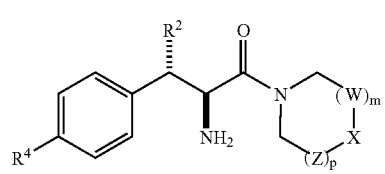

(Ii)

wherein X is $CH_2$, S, CHF, or $CF_2$;
W and Z are each independently $CH_2$, CHF, or $CF_2$;
$R^4$ is phenyl, heteroaryl, or heterocyclyl, wherein phenyl, heteroaryl, and heterocyclyl are unsubstituted or substituted with one to three $R^5$ substituents;
$R^2$ is selected from the group consisting of:
methyl,
ethyl,
$CH_2$-cyclopropyl,
COOH,
COOMe,
COOEt,
CONHMe,
$CONMe_2$,
$CONH_2$,
CONHEt,
$CONMeCH_2Ph$,
pyrrolidin-1-ylcarbonyl,
azetidin-1-ylcarbonyl,
3-fluoroazetidin-1-ylcarbonyl,
morpholin-4-ylcarbonyl, and
[(tetrazol-5-yl)amino]carbonyl; and
each $R^5$ is independently selected from the group consisting of:
halogen,
cyano,
oxo,
hydroxy,
$C_{1-6}$ alkyl, wherein alkyl is unsubstituted or substituted with one to five halogens,
$C_{1-6}$ alkoxy, wherein alkoxy is unsubstituted or substituted with one to five halogens,
$NR^6R^7$,
$CONR^6R^7$,
$OCONR^6R^7$,
$SO_2NR^6R^7$,
$SO_2R^9$,
$NR^8SO_2R^9$,
$NR^8CONR^6R^7$,
$NR^8COR^8$, NR⁸CO₂R⁹,
COOH,
COOC$_{1-6}$ alkyl,
aryl, wherein aryl is unsubstituted or substituted with one to five substituents independently selected from halogen, hydroxy, CO₂H, C$_{1-6}$ alkyloxycarbonyl, C$_{1-6}$ alkyl, and C$_{1-6}$ alkoxy, wherein alkyl and alkoxy are unsubstituted or substituted with one to five halogens,
heteroaryl, wherein heteroaryl is unsubstituted or substituted with one to three substituents independently selected from hydroxy, halogen, CO₂H, C$_{1-6}$ alkyloxycarbonyl, C$_{1-6}$ alkyl, and C$_{1-6}$ alkoxy, wherein alkyl and alkoxy are unsubstituted or substituted with one to five halogens,
heterocyclyl, wherein heterocyclyl is unsubstituted or substituted with one to three substituents independently selected from oxo, hydroxy, halogen, CO₂H, C$_{1-6}$ alkyloxycarbonyl, C$_{1-6}$ alkyl, and C$_{1-6}$ alkoxy, wherein alkyl and alkoxy are unsubstituted or substituted with one to five halogens, and
(CH₂)$_n$—C$_{3-6}$ cycloalkyl, wherein cycloalkyl is unsubstituted or substituted with one to three substituents independently selected from halogen, hydroxy, C$_{1-6}$ alkyl, and C$_{1-6}$ alkoxy, wherein alkyl and alkoxy are unsubstituted or substituted with one to five halogens.

10. The compound of claim 9 wherein each R⁵ is independently selected from the group consisting of:
halogen,
cyano,
oxo,
C$_{1-6}$ alkyl, wherein alkyl is unsubstituted or substituted with one to five halogens,
C$_{1-6}$ alkoxy, wherein alkoxy is unsubstituted or substituted with one to five halogens,
CONR⁶R⁷,
NR⁸COR⁸,
SO₂R⁹,
NR⁸SO₂R⁹,
COOH,
COOC$_{1-6}$ alkyl,
heteroaryl, wherein heteroaryl is unsubstituted or substituted with one to three substituents independently selected from hydroxy, halogen, CO₂H, C$_{1-6}$ alkyloxycarbonyl, C$_{1-6}$ alkyl, and C$_{1-6}$ alkoxy, wherein alkyl and alkoxy are unsubstituted or substituted with one to five halogens, and
heterocyclyl, wherein heterocyclyl is unsubstituted or substituted with one to three substituents independently selected from oxo, hydroxy, halogen, CO₂H, C$_{1-6}$ alkyloxycarbonyl, C$_{1-6}$ alkyl, and C$_{1-6}$ alkoxy, wherein alkyl and alkoxy are unsubstituted or substituted with one to five halogens.

11. The compound of claim 9 wherein R⁴ is selected from the group consisting of:
4-fluorophenyl,
2,4-difluorophenyl,
3,4-difluorophenyl,
2-chlorophenyl,
2-fluorophenyl,
3-(methylsulfonyl)phenyl,
3-(ethoxycarbonyl)phenyl,
3-carboxyphenyl,
3-(aminocarbonyl)phenyl,
3-[(tert-butylamino)carbonyl]phenyl,
3-[(phenylamino)carbonyl]phenyl,
3-[(thiazol-2-ylamino)carbonyl]phenyl,
3-[(tetrazol-5-ylamino)carbonyl]phenyl,
3-[[(trifluoromethyl)sulfonyl]amino]phenyl,
3-(tetrazol-5-yl)phenyl,
4-fluoro-3-(tetrazol-5-yl)phenyl,
2-fluoro-5-(tetrazol-5-yl)phenyl,
3-(5-oxo-4,5-dihydro-1,2,4-oxadiazol-3-yl)phenyl,
4-fluoro-3-(5-oxo-4,5-dihydro-1,2,4-oxadiazol-3-yl)phenyl,
3-(5-oxo-4,5-dihydro-1,3,4-oxadiazol-2-yl)phenyl,
3-(5-oxo-4,5-dihydro-1H-1,2,4-triazol-3-yl)phenyl,
3-(1,3,4-oxadiazol-2-yl)phenyl,
3-(1,2,4-triazol-3-yl)phenyl,
3-[5-(trifluoromethyl)-1,2,4-triazol-3-yl]phenyl,
3-(5-ethoxy-1,2,4-triazol-3-yl)phenyl,
pyridin-3-yl,
6-fluoro-pyridin-3-yl,
6-methoxypyridin-3-yl,
6-oxo-1,6-dihydropyridin-3-yl,
1-methyl-6-oxo-1,6-dihydropyridin-3-yl,
1-ethyl-6-oxo-1,6-dihydropyridin-3-yl,
5-bromo-1-methyl-6-oxo-1,6-dihydropyridin-3-yl,
imidazo[1,2-α]pyridin-6-yl,
[1,2,4]triazolo[4,3-α]pyridin-6-yl,
3-(trifluoromethyl)[1,2,4]triazolo[4,3-α]pyridin-6-yl,
3-oxo-2,3-dihydro[1,2,4]triazolo[4,3-α]pyridin-6-yl,
2-methyl-3-oxo-2,3-dihydro[1,2,4]triazolo[4,3-α]pyridin-6-yl,
4-aminoquinazolin-6-yl,
2-(acetylamino)imidazo[1,2-α]pyridin-6-yl,
3-aminoimidazo[1,2-α]pyridin-6-yl,
3-carboxypyrazolo[1,5-α]pyridin-5-yl,
5-bromo-6-oxo-1,6-dihydropyridin-3-yl,
[1,2,4]triazolo[1,5-α]pyridin-6-yl,
[1,2,4]triazolo[1,5-α]pyridin-7-yl, and
pyrazolo[1,5-α]pyrimidin-5-yl.

12. The compound of claim 9 of the structural formula Ij:

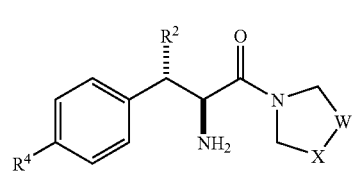

(Ij)

wherein R² is selected from the group consisting of:
methyl,
ethyl,
CH₂-cyclopropyl,
COOH,
COOMe,
COOEt,
CONHMe,
CONMe₂,
CONH₂,
CONHEt,
CONMeCH₂Ph,
pyrrolidin-1-ylcarbonyl,
azetidin-1-ylcarbonyl,
3-fluoroazetidin-1-ylcarbonyl,
morpholin-4-ylcarbonyl, and
[(tetrazol-5-yl)amino]carbonyl; and
R⁴ is selected from the group consisting of
4-fluorophenyl,
2,4-difluorophenyl, 3,4-difluorophenyl,
2-chlorophenyl,
2-fluorophenyl,
3-(methylsulfonyl)phenyl,
3-(ethoxycarbonyl)phenyl,
3-carboxyphenyl,
3-(aminocarbonyl)phenyl,
3-[(tert-butylamino)carbonyl]phenyl,
3-[(phenylamino)carbonyl]phenyl,
3-[(thiazol-2-ylamino)carbonyl]phenyl,
3-[(tetrazol-5-ylamino)carbonyl]phenyl,
3-[[(trifluoromethyl)sulfonyl]amino]phenyl,
3-(tetrazol-5-yl)phenyl,
4-fluoro-3-(tetrazol-5-yl)phenyl,
2-fluoro-5-(tetrazol-5-yl)phenyl,
3-(5-oxo-4,5-dihydro-1,2,4-oxadiazol-3-yl)phenyl,
4-fluoro-3-(5-oxo-4,5-dihydro-1,2,4-oxadiazol-3-yl)phenyl,
3-(5-oxo-4,5-dihydro-1,3,4-oxadiazol-2-yl)phenyl,
3-(5-oxo-4,5-dihydro-1H-1,2,4-triazol-3-yl)phenyl,
3-(1,3,4-oxadiazol-2-yl)phenyl,
3-(1,2,4-triazol-3-yl)phenyl,
3-[5-(trifluoromethyl)-1,2,4-triazol-3-yl]phenyl,
3-(5-ethoxy-1,2,4-triazol-3-yl)phenyl,
pyridin-3-yl,
6-fluoro-pyridin-3-yl,
6-methoxypyridin-3-yl,
6-oxo-1,6-dihydropyridin-3-yl,
1-methyl-6-oxo-1,6-dihydropyridin-3-yl,
1-ethyl-6-oxo-1,6-dihydropyridin-3-yl,
5-bromo-1-methyl-6-oxo-1,6-dihydropyridin-3-yl,
imidazo[1,2-α]pyridin-6-yl,
[1,2,4]triazolo[4,3-α]pyridin-6-yl,
3-(trifluoromethyl)[1,2,4]triazolo[4,3-α]pyridin-6-yl,
3-oxo-2,3-dihydro[1,2,4]triazolo[4,3-α]pyridin-6-yl,
2-methyl-3-oxo-2,3-dihydro[1,2,4]triazolo[4,3-α]pyridin-6-yl,
4-aminoquinazolin-6-yl,
2-(acetylamino)imidazo[1,2-α]pyridin-6-yl,
3-aminoimidazo[1,2-α]pyridin-6-yl,
3-carboxypyrazolo[1,5-α]pyridin-5-yl,
5-bromo-6-oxo-1,6-dihydropyridin-3-yl,
[1,2,4]triazolo[1,5-α]pyridin-6-yl,
[1,2,4]triazolo[1,5-α]pyridin-7-yl, and
pyrazolo[1,5-α]pyrimidin-5-yl.

13. The compound of claim 12 wherein W is $CH_2$ and X is CHF or $CF_2$.

14. The compound of claim 12 of the structural formula selected from the group consisting of:

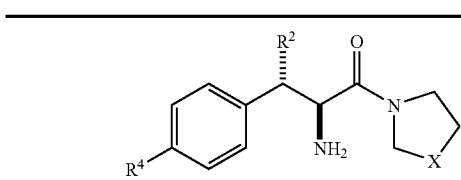

| $R^4$ | $R^2$ | X |
| --- | --- | --- |
| phenyl | Me | (S)—CHF |
| 4-($SO_2$Me)-phenyl | Me | (S)—CHF |
| 3-($SO_2$Me)-phenyl | Me | (S)—CHF |
| pyrazin-5-yl | Me | (S)—CHF |
| 3-chloropyridin-4-yl | Me | (S)—CHF |
| 2,4-difluorophenyl | Me | (S)—CHF |
| 2,4-difluorophenyl | Me | (S)—CHF |

-continued

| $R^4$ | $R^2$ | X |
| --- | --- | --- |
| 2,5-difluorophenyl | Me | (S)—CHF |
| 3,5-difluorophenyl | Me | (S)—CHF |
| 3-(ethoxycarbonyl)phenyl | Me | (S)—CHF |
| 4-(ethoxycarbonyl)phenyl | Me | (S)—CHF |
| 3-($NHSO_2$Me)-phenyl | Me | (S)—CHF |
| 4-($NHSO_2$Me)-phenyl | Me | (S)—CHF |
| 4-$CO_2$H-phenyl | Me | (S)—CHF |
| pyridin-3-yl | Me | (S)—CHF |
| 6-OMe-pyridin-3-yl | Me | (S)—CHF |
| 2-Cl-phenyl | Me | (S)—CHF |
| 2-F-phenyl | Me | (S)—CHF |
| 3-CN-phenyl | Me | (S)—CHF |
| pyridin-4-yl | Me | (S)—CHF |
| pyridin-2-yl | Me | (S)—CHF |
| 2,4-difluorophenyl | Cyclopropylmethyl | (S)—CHF |
| 3-($MeSO_2$)phenyl | Cyclopropylmethyl | (S)—CHF |
| 4-fluoro-(3-tetrazol-5-yl)phenyl | Me | (S)—CHF |
| 3-(aminosulfonyl)phenyl | Me | (S)—CHF |
| 2-fluoro-(5-tetrazol-5-yl)phenyl | Me | (S)—CHF |
| 3-hydroxyphenyl | Me | (S)—CHF |
| 6-fluoropyridin-3-yl | Me | (S)—CHF |
| 3-(aminocarbonyl)phenyl | Me | (S)—CHF |
| 3-(phenylaminocarbonyl)phenyl | Me | (S)—CHF |
| 4-fluoro-3-(5-oxo-4,5-dihydro-1,2,4-oxadiazol-3-yl)phenyl | Me | (S)—CHF |
| 3-[(thiazol-2-yl)aminocarbonyl]phenyl | Me | (S)—CHF |
| 3-[(tetrazol-5-yl)aminocarbonyl]phenyl | Me | (S)—CHF |
| imidazo[1,2-a]pyridin-6-yl | Me | (S)—CHF |
| 2-methoxyphenyl | Me | (S)—CHF |
| 3-(5-oxo-4,5-dihydro-1,3,4-oxadiazol-2-yl)phenyl | Me | (S)—CHF |
| 3-(5-ethoxy-1H-1,2,4-triazol-3-yl)phenyl | Me | (S)—CHF |
| 1-ethyl-6-oxo-1,6-dihydropyridin-3-yl | Me | (S)—CHF |
| quinolin-6-yl | Me | (S)—CHF |
| 3-(2-oxo-2,3-dihydro-1H-imidazol-4-yl)phenyl | Me | (S)—CHF |
| 2-methylphenyl | Me | (S)—CHF |
| 2-(trifluoromethyl)phenyl | Me | (S)—CHF |
| 3-[5-(trifluoromethyl)-4H-1,2,4-triazol-3-yl]phenyl | Me | (S)—CHF |
| 4-oxo-3,4-dihydroquinazolin-6-yl | Me | (S)—CHF |
| 4-fluorophenyl | CONHEt | (S)—CHF |
| 1-methyl-6-oxo-1,6-dihydropyridin-3-yl | Et | (S)—CHF |
| 6-oxo-1,6-dihydropyridin-3-yl | Et | (S)—CHF |
| 3-(trifluoromethyl)[1,2,4]triazolo[4,3-a]pyridin-6-yl | Me | (S)—CHF |
| 4-fluorophenyl | $CONH_2$ | (S)—CHF |
| 3-oxo-2,3-dihydro[1,2,4]triazolo[4,3-a]pyridin-6-yl | Me | (S)—CHF |
| 1-methyl-6-oxo-1,6-dihydropyridin-3-yl | Me | $CF_2$ |
| 6-oxo-1,6-dihydropyridin-3-yl | Me | $CF_2$ |
| 4-aminoquinazolin-6-yl | Me | (S)—CHF |
| 5-bromo-1-methyl-6-oxo-1,6-dihydropyridin-3-yl | Me | (S)—CHF |
| 4-fluorophenyl | (pyrrolidin-1-yl)carbonyl | (S)—CHF |
| 4-fluorophenyl | (azetidin-1-yl)carbonyl | (S)—CHF |
| 2-(acetylamino)imidazo[1,2-a]pyridin-6-yl | Me | (S)—CHF |
| 2-methyl-3-oxo-2,3-dihydro[1,2,4]triazolo[4,3-a]pyridin-6-yl | Me | (S)—CHF |
| 3-aminoimidazo[1,2-a]pyridin-6-yl | Me | (S)—CHF |
| 4-fluorophenyl | [(tetrazol-5-yl)amino]carbonyl | (S)—CHF |
| 4-fluorophenyl | CONHMe | (S)—CHF |
| 4-fluorophenyl | $CONEt_2$ | (S)—CHF |

-continued

| R⁴ | R² | X |
|---|---|---|
| 4-fluorophenyl | COOMe | (S)—CHF |
| [1,2,4]triazolo[1,5-a]pyridin-6-yl | Me | (S)—CHF |
| 4-fluorophenyl | COOH | CH₂ |
| 4-fluorophenyl | COOH | CF₂ |
| 4-fluorophenyl | CONMe₂ | CH₂ |
| 3-carboxypyrazolo[1,5-a]pyridin-5-yl | Me | (S)—CHF |
| 6-oxo-1,6-dihydropyridin-3-yl | Me | CH₂ |
| 4-fluorophenyl | Me | (S)—CHF |
| 3-carboxyphenyl | Me | (S)—CHF |
| 3-(tetrazol-5-yl)phenyl | Me | (S)—CHF |
| 3-(5-oxo-4,5-dihydro-1,2,4-oxa-diazol-3-yl)phenyl | Me | (S)—CHF |
| 6-oxo-1,6-dihydropyridin-3-yl | Me | (S)—CHF |
| 1-methyl-6-oxo-1,6-dihydropyridin-3-yl | Cyclo-propylmethyl | (S)—CHF |
| 5-bromo-6-oxo-1,6-dihydropyridin-3-yl | Me | (S)—CHF |
| 3-[(tert-butylamino)carbonyl]phenyl | Me | (S)—CHF |
| 3-[[(trifluoro-methyl)sulfonyl]amino]phenyl | Me | (S)—CHF |
| [1,2,4]triazolo[4,3-a]pyridin-6-yl | Me | (S)—CHF |
| 4-fluorophenyl | COOH | (S)—CHF |
| 4-fluorophenyl | CONMe₂ | (S)—CHF |
| [1,2,4]triazolo[1,5-a]pyridin-6-yl | CONMe₂ | (S)—CHF |
| [1,2,4]triazolo[1,5-a]pyridin-7-yl | CONMe₂ | (S)—CHF |
| pyrazolo[1,5-a]pyrimidin-5-yl | CONMe₂ | (S)—CHF |
| [1,2,4]triazolo[1,5-a]pyridin-6-yl | CONMe₂ | CF₂ |
| [1,2,4]triazolo[1,5-a]pyridin-7-yl | CONMe₂ | CF₂ |
| pyrazolo[1,5-a]pyrimidin-5-yl | CONMe₂ | CF₂ |
| [1,2,4]triazolo[1,5-a]pyridin-6-yl | CONMe₂ | CH₂ |
| [1,2,4]triazolo[1,5-a]pyridin-6-yl | (3-fluoroazetidin-1-yl)carbonyl | CH₂ |
| [1,2,4]triazolo[1,5-a]pyridin-6-yl | (pyrrolidine-1-yl)carbonyl | CF₂ |
| [1,2,4]triazolo[1,5-a]pyridin-6-yl | CONMeCH₂Ph | CF₂ |
| [1,2,4]triazolo[1,5-a]pyridin-6-yl | (morpholin-1-yl)carbonyl | CF₂ | or a pharmaceutically acceptable salt thereof.

15. The compound of claim 11 selected from the group consisting of

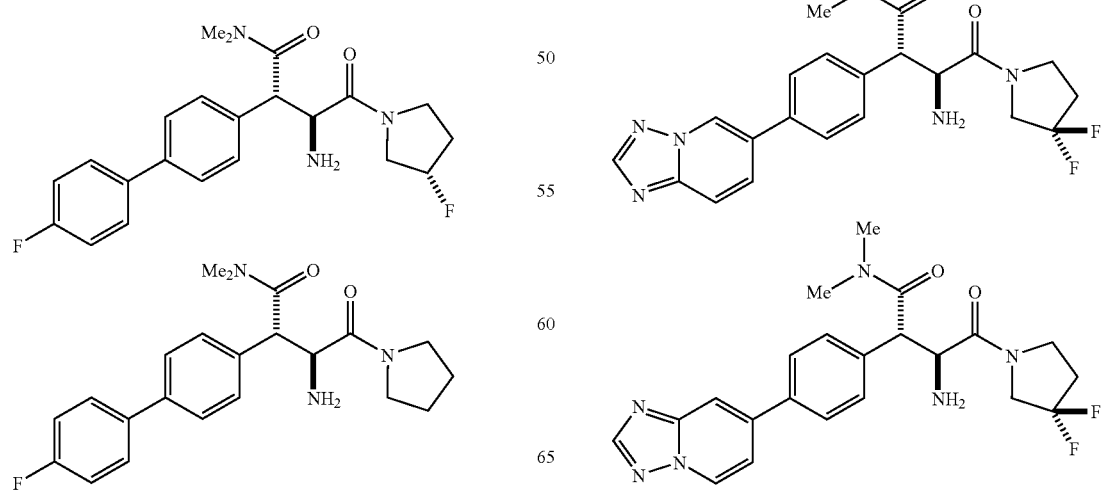

-continued

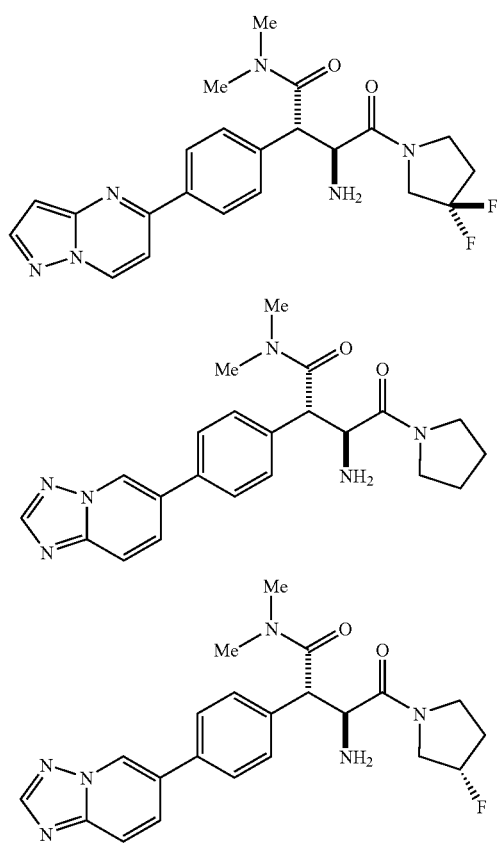

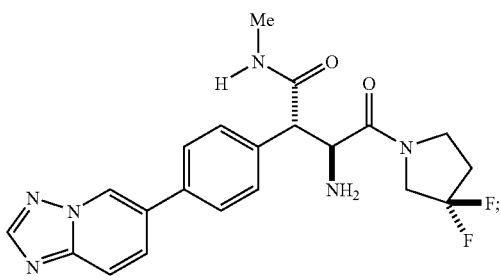

or a pharmaceutically acceptable salt thereof.

16. The compound of claim 15 which is

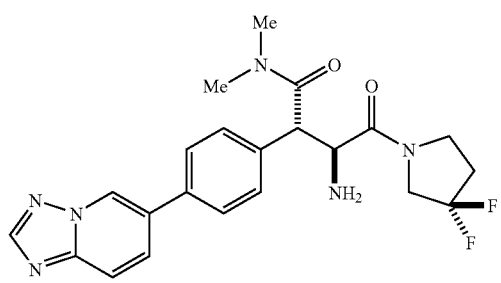

or a pharmaceutically acceptable salt thereof.

17. The compound of claim 15 which is

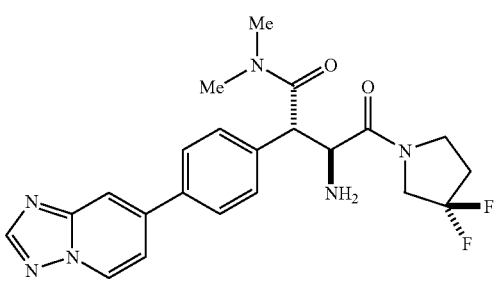

or a pharmaceutically acceptable salt thereof.

18. The compound of claim 15 which is

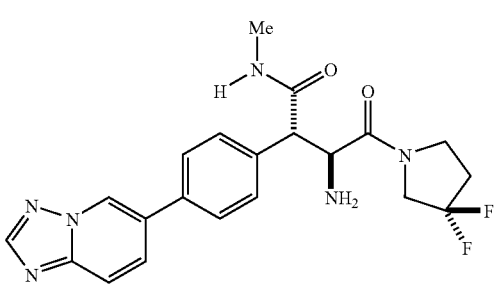

or a pharmaceutically acceptable salt thereof.

19. The compound of claim 15 which is

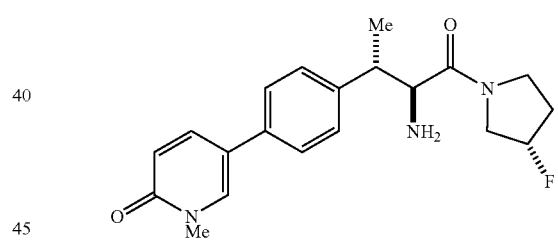

or a pharmaceutically acceptable salt thereof.

20. The compound of claim 15 which is

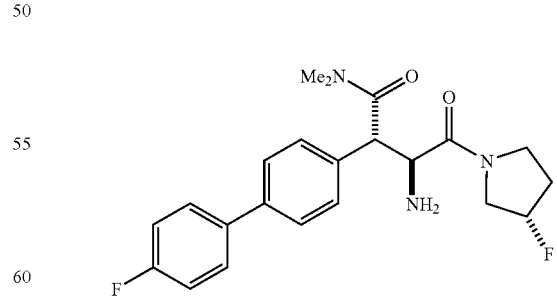

or a pharmaceutically acceptable salt thereof.

21. A pharmaceutical composition which comprises a compound of claim 1 and a pharmaceutically acceptable carrier.

22. A method for treating non-insulin dependent (Type 2) diabetes in a mammal in need thereof which comprises the administration to the mammal of a therapeutically effective amount of a compound of claim 1.

23. A method of treating Type 2 diabetes in a mammal in need thereof comprising administering to the mammal a therapeutically effective amount of a compound of claim 1 in combination with metformin.

* * * * *